US010690763B2

(12) United States Patent
Shouldice et al.

(10) Patent No.: US 10,690,763 B2
(45) Date of Patent: Jun. 23, 2020

(54) DETECTION AND IDENTIFICATION OF A HUMAN FROM CHARACTERISTIC SIGNALS

(71) Applicant: RESMED SENSOR TECHNOLOGIES LIMITED, Dublin (IE)

(72) Inventors: Redmond Shouldice, Dublin (IE); Emer Doheny, Dublin (IE); Alberto Zaffaroni, Dublin (IE)

(73) Assignee: ResMed Sensor Technologies Limited (IE)

( * ) Notice: Subject to any disclaimer, the term of this patent is extended or adjusted under 35 U.S.C. 154(b) by 0 days.

(21) Appl. No.: 15/562,751

(22) PCT Filed: Apr. 20, 2016

(86) PCT No.: PCT/EP2016/058789
§ 371 (c)(1),
(2) Date: Sep. 28, 2017

(87) PCT Pub. No.: WO2016/170005
PCT Pub. Date: Oct. 27, 2016

(65) Prior Publication Data
US 2018/0106897 A1 Apr. 19, 2018

Related U.S. Application Data

(60) Provisional application No. 62/207,687, filed on Aug. 20, 2015, provisional application No. 62/149,839, filed on Apr. 20, 2015.

(51) Int. Cl.
*G01S 13/56* (2006.01)
*G01S 7/41* (2006.01)
(Continued)

(52) U.S. Cl.
CPC ............ *G01S 13/56* (2013.01); *A61B 5/0205* (2013.01); *A61B 5/0507* (2013.01);
(Continued)

(58) Field of Classification Search
None
See application file for complete search history.

(56) References Cited

U.S. PATENT DOCUMENTS

| 4,197,537 A | 4/1980 | Follen et al. |
| 5,361,070 A | 11/1994 | McEwan |

(Continued)

FOREIGN PATENT DOCUMENTS

| EP | 1318307 A1 | 6/2003 |
| JP | 2010133692 A | 6/2010 |

(Continued)

OTHER PUBLICATIONS

Adib, et al., "Multi-Person Motion Tracking via RF Body Reflections", MIT CSAIL, Apr. 26, 2014.
(Continued)

*Primary Examiner* — Leon Viet Q Nguyen
(74) *Attorney, Agent, or Firm* — Botos Churchill IP Law LLP

(57) ABSTRACT

One or more sensors are configured for detection of characteristics of moving objects and living subjects for human identification or authentication. One or more processors, such as in a system of sensors or that control a sensor, may be configured to process signals from the one or more sensors to identify a person. The processing may include evaluating features from the signals such as breathing rate, respiration depth, degree of movement and heart rate etc. The sensors may be radio frequency non-contact sensors with automated detection control to change detection control
(Continued)

parameters based on the identification of living beings, such as to avoid sensor interference.

58 Claims, 31 Drawing Sheets

(51) Int. Cl.
| | |
|---|---|
| *G01S 13/88* | (2006.01) |
| *A61B 5/00* | (2006.01) |
| *A61B 5/05* | (2006.01) |
| *A61B 5/0205* | (2006.01) |
| *A61B 5/113* | (2006.01) |
| *A61B 5/11* | (2006.01) |
| *A61M 16/00* | (2006.01) |
| *G01S 13/87* | (2006.01) |
| *A61M 16/06* | (2006.01) |
| *A61M 16/16* | (2006.01) |
| *A61B 5/021* | (2006.01) |
| *A61B 5/024* | (2006.01) |
| *A61B 5/053* | (2006.01) |
| *A61B 5/08* | (2006.01) |
| *A61B 7/00* | (2006.01) |

(52) U.S. Cl.
CPC ............ *A61B 5/1102* (2013.01); *A61B 5/113* (2013.01); *A61B 5/4812* (2013.01); *A61B 5/4818* (2013.01); *A61B 5/7264* (2013.01); *A61M 16/0051* (2013.01); *A61M 16/026* (2017.08); *G01S 7/415* (2013.01); *G01S 13/88* (2013.01); *A61B 5/0077* (2013.01); *A61B 5/021* (2013.01); *A61B 5/024* (2013.01); *A61B 5/0533* (2013.01); *A61B 5/0816* (2013.01); *A61B 5/1123* (2013.01); *A61B 5/4836* (2013.01); *A61B 5/7267* (2013.01); *A61B 7/003* (2013.01); *A61M 16/0069* (2014.02); *A61M 16/0072* (2013.01); *A61M 16/0683* (2013.01); *A61M 16/16* (2013.01); *A61M 2016/0027* (2013.01); *A61M 2016/0033* (2013.01); *A61M 2202/0208* (2013.01); *A61M 2205/21* (2013.01); *A61M 2205/3553* (2013.01); *A61M 2205/502* (2013.01); *A61M 2205/6009* (2013.01); *A61M 2205/609* (2013.01); *A61M 2205/6018* (2013.01); *G01S 13/87* (2013.01)

(56) References Cited

U.S. PATENT DOCUMENTS

| | | | |
|---|---|---|---|
| 5,682,164 A | 10/1997 | McEwan | |
| 5,966,090 A | 10/1999 | McEwan | |
| 6,426,716 B1 | 7/2002 | McEwan | |
| 6,515,586 B1* | 2/2003 | Wymore | G08B 13/10 |
| | | | 307/116 |
| 6,993,378 B2 | 1/2006 | Wiederhold et al. | |
| 7,952,515 B2 | 5/2011 | McEwan | |
| 7,994,968 B2 | 8/2011 | McEwan | |
| 8,232,866 B2 | 7/2012 | McGrath et al. | |
| 8,321,006 B1 | 11/2012 | Synder et al. | |
| 8,762,733 B2 | 6/2014 | Derchak et al. | |
| 2003/0135097 A1* | 7/2003 | Wiederhold | A61B 5/02055 |
| | | | 600/301 |
| 2003/0236450 A1* | 12/2003 | Kocinski | G16H 40/63 |
| | | | 600/300 |
| 2006/0155386 A1* | 7/2006 | Wells | A61B 5/0006 |
| | | | 623/25 |
| 2008/0165046 A1 | 7/2008 | Fullerton et al. | |
| 2009/0203972 A1* | 8/2009 | Heneghan | A61B 5/0507 |
| | | | 600/301 |
| 2009/0275807 A1* | 11/2009 | Sitzman | A61B 5/0205 |
| | | | 600/301 |
| 2010/0090862 A1* | 4/2010 | Dubrow | H04Q 9/00 |
| | | | 340/870.01 |
| 2010/0152600 A1* | 6/2010 | Droitcour | A61B 5/05 |
| | | | 600/534 |
| 2010/0191076 A1 | 7/2010 | Lewicke et al. | |
| 2011/0003550 A1* | 1/2011 | Klinghult | G06F 1/1684 |
| | | | 455/41.3 |
| 2011/0040574 A1 | 2/2011 | Fung et al. | |
| 2012/0016798 A1* | 1/2012 | Carper | G06Q 20/1085 |
| | | | 705/43 |
| 2012/0068819 A1 | 3/2012 | McGrath et al. | |
| 2012/0245479 A1 | 9/2012 | Ganesh et al. | |
| 2013/0298039 A1* | 11/2013 | Mestre | G06F 3/0484 |
| | | | 715/753 |
| 2013/0321123 A1* | 12/2013 | Wan | G05B 15/02 |
| | | | 340/5.2 |
| 2013/0340758 A1 | 12/2013 | Schindhelm | |
| 2014/0024917 A1 | 1/2014 | McMahon et al. | |
| 2014/0288435 A1* | 9/2014 | Richards | A61B 5/02427 |
| | | | 600/479 |
| 2015/0190086 A1* | 7/2015 | Chan | A61B 5/4812 |
| | | | 600/301 |
| 2015/0258431 A1* | 9/2015 | Stafford | A63F 13/213 |
| | | | 463/31 |
| 2016/0030967 A1* | 2/2016 | Ayer | B05B 17/08 |
| | | | 239/1 |
| 2016/0073950 A1* | 3/2016 | Franceschetti | G16H 40/67 |
| | | | 340/575 |

FOREIGN PATENT DOCUMENTS

| | | |
|---|---|---|
| JP | 2012017744 A | 1/2012 |
| WO | 2003000015 | 1/2003 |
| WO | 2004096045 A1 | 11/2004 |
| WO | 2007143535 A2 | 12/2007 |
| WO | 2008057883 A2 | 5/2008 |
| WO | 2008102291 A2 | 8/2008 |
| WO | 2010036700 A1 | 4/2010 |
| WO | 2010091168 A1 | 8/2010 |
| WO | 2011006199 A1 | 1/2011 |
| WO | 2015006364 A2 | 1/2015 |
| WO | 2016019292 A1 | 2/2016 |
| WO | 2014047310 A1 | 3/2017 |

OTHER PUBLICATIONS

Boric-Lubecke, et al., "Doppler Radar Sensing of Multiple Subjects in Single and Multiple Antenna Systems", IEEE, Sep. 30, 2005.
De Chazal, Philip, et al., "Sleep/wake measurement using a non-contact biomotion sensor", J. Sleep Res., pp. 356-366 (2011) V.20, Issue 2., (Aug. 12, 2010).
Sriram, Janani, et al., "Activity-aware ECG-based Patient Authentication for Remote Health Monitoring", Proceedings of the 2009 International Conference on Multimodal Interfaces, ICMI-MLMI '09, pp. 297-304, Jan. 1, 2009.
Zhou, et al., "Detection of Multiple Heartbeats Using Doppler Radar", IEEE, May 20, 2016.
JP Office Action dated Apr. 3, 2020, JP Application No. 2017-554455.

* cited by examiner

DETECTION AND IDENTIFICATION OF A HUMAN FROM CHARACTERISTIC SIGNALS

CROSS-REFERENCE TO RELATED APPLICATIONS

The present application is a national phase entry under 35 U.S.C. § 371 of International Application No. PCT/EP2016/058789 filed Apr. 20, 2016, published in English, which claims priority from U.S. Provisional Patent Application No. 62/207,687 filed Aug. 20, 2015 and U.S. Provisional Patent Application 62/149,839 filed Apr. 20, 2015, all of which are incorporated herein by reference.

FIELD OF THE TECHNOLOGY

The present technology relates to circuits and sensors for detection of characteristics of moving objects and living subjects. More particularly, it relates to such sensors, for example in health monitors, such as range gated radio frequency motion sensing, with particular emphasis on signal characteristics for human identification or authentication.

BACKGROUND OF THE TECHNOLOGY

Continuous wave (CW) Doppler radar motion sensors emit a continuous wave radio frequency (RF) carrier and mix the transmitted RF with the return echoes to produce a difference frequency equal to the Doppler shift produced by a moving target. These sensors do not have a definite range limit (i.e., they can receive signals for both near and far objects, with the received signal being a function of radar cross section). This can lead to false triggers i.e., motion artefact interference. They may also have an undesirably high sensitivity at close range that leads to false triggering.

A pulse Doppler motion sensor is described in U.S. Pat. No. 4,197,537 to Follen et al. A short pulse is transmitted and its echo is self-mixed with the transmitted pulse. The pulse width defines the range-gated region. When the transmit pulse ends, mixing ends and target returns arriving after the end of the transmit pulse are not mixed and are thereby gated out.

A Differential pulse Doppler motion sensor disclosed in U.S. Pat. No. 5,966,090, "Differential Pulse Radar Motion Sensor," to McEwan, alternately transmits at two different pulse widths. It then subtracts the Doppler responses from each width to produce a range gated "Doppler" sensing region having a fairly constant response versus range.

Impulse radar, such as that described in U.S. Pat. No. 5,361,070, "Ultra-Wideband Radar Motion Sensor," to McEwan produces a very narrow sensing region that is related to the transmitted pulse width. A two-pulse Doppler radar motion sensor, as described in U.S. Pat. No. 5,682,164, "Pulse Homodyne Field Disturbance Sensor," to McEwan, transmits a first pulse and after a delay generates a second pulse that mixes with echoes from the first pulse. Thus a range gated sensing band is formed with defined minimum and maximum ranges. UWB radar motion sensors have the disadvantage of not having global RF regulatory acceptance as an intentional radiator. They also have difficulty sensing objects at medium ranges and in some embodiments can be prone to RF interference.

A modulated pulse Doppler sensor is described in U.S. Pat. No. 6,426,716 to McEwan. The range gated microwave motion sensor includes adjustable minimum and maximum detection ranges. The apparatus includes an RF oscillator with associated pulse generating and delay elements to produce the transmit and mixer pulses, a single transmit (TX)/receive (RX) antenna or a pair of separate TX and RX antennas, and an RF receiver, including a detector/mixer with associated filtering, amplifying and demodulating elements to produce a range gated Doppler signal from the mixer and echo pulses.

In U.S. Pat. No. 7,952,515, McEwan discloses a particular holographic radar. It adds a range gate to holographic radar to limit response to a specific downrange region. McEwan states that cleaner, more clutter-free radar holograms of an imaged surface can be obtained, particularly when penetrating materials to image interior image planes, or slices. The range-gating enables stacked hologram technology, where multiple imaged surfaces can be stacked in the downrange direction.

In U.S. Pat. No. 7,994,968, McEwan discloses an RF magnitude sampler for holographic radar. McEwan describes that the RF magnitude sampler can finely resolve interferometric patterns produced by narrowband holographic pulse radar.

In U.S. Patent Application Publication No. 2014/0024917, McMahon et al, describe a sensor for physiology sensing that may be configured to generate oscillation signals for emitting radio frequency pulses for range gated sensing. The sensor may include a radio frequency transmitter configured to emit the pulses and a receiver configured to receive reflected ones of the emitted radio frequency pulses. The received pulses may be processed to detect physiology characteristics such as motion, sleep, respiration and/or heartbeat.

Wearable wristbands such as the Nymi introduce another parameter that can be used in authentication systems—the ECG shape (morphology) that is specific for each user. (https://www.nymi.com/)

US 20100191076 A1 (Aaron Lewicke, Yi Zhang, John D. Hatlestad) describes daytime/nighttime respiration rate monitoring.

U.S. Pat. No. 8,232,866 (William R. McGrath, Ashit Talukder) describes remote long standoff biometric identification using microwave cardiac signals.

U.S. Pat. No. 832,100 (Seth Snyder, Jasper Speicher) describes a Biometric data display system and method.

WO 2003000015 (Mark D Wiederhold, Rodney P Meyer, Steven A Israel, John M Irvine) describes identification by analysis of physiometric variation.

U.S. Pat. No. 8,762,733 (P. Alexander Derchak, Lance Myers) describes System and method for identity confirmation using physiologic biometrics to determine a physiologic fingerprint US 20110040574 (Ho Chung Nicholas Fung, Chu Yong Sang) describes Health Monitoring System with Biometric Identification.

U.S. Pat. No. 6,993,378 (Mark D. Wiederhold, Steven A. Israel, Rodney P. Meyer, John M. Irvine) describes identification by analysis of physiometric variation.

There may be a need to improve sensors and/or their signal processing for sensing such characteristics for identification or authentication.

For authentication and other purposes, it is desirable to be able to identify a person.

The advent of wearable and non-contact physiological and behavioral data capture has led to a need to detect and identify a specific person from their personal biometric "fingerprint", both to reject data from a another person (impersonation), and to assure compliance or use of those sensors (and potentially attached or associated services or therapies). Such characteristics can be drawn from physiological and behavioral signals.

In addition to detecting that sensor data have been collected from a specific user and their micro and macro environment, it is desirable that a system be able to detect deviations from normal (healthy) signals, and be robust to such changes (e.g., worsening condition or improving condition due to treatment/therapy).

SUMMARY OF THE TECHNOLOGY

One aspect of some embodiments of the present technology relates to a sensor for detecting physiology characteristics such as with radio frequency signals.

Another aspect of some embodiments of the present technology relates to a sensor for authenticating a person from detected signal characteristics, such as with radio frequency signals.

Some versions of the present technology may include a method or system to identify a person for monitoring physiological parameters of one or more persons, such as for health monitoring. The system may include one or more sensors for monitoring the one or more persons' physiological parameters. The system may include one or more processors, the one or more processors configured to process signals from the one or more sensors to identify a person, the processing comprising an evaluation of features comprising respiratory features, cardiac features, or movement features, such as, for example, any one or more of detected breathing rate, detected respiration depth, detected degree of movement and detected heart rate, the evaluation involving analysis of any one or more of these detected features.

In some versions, the one or more sensors comprises a radio frequency non-contact sensor. The detection may include detection of physiological characteristics during sleep of the person. The processing may include detection of sleep stages. The processing may include detection of deep sleep. The processing may include detection of REM sleep. The detection may include detection of physiological characteristics during awake time of the person. The one or more sensors may include any one or more of the sensors described throughout the detailed specification. The evaluation of the one or more processors may include detection and analysis of any one or more characteristics of the sensor signal described in the detailed specification.

In some versions, the one or more sensors may be configured to minimize interference, such as Radio Frequency (RF) interference, between at least two of the one or more sensors. The one or more sensors may be configured to minimize interference, such as RF interference, by modifying control parameters for range gating pulse timing, emitted power levels of pulses such as RF pulses, detection frequency of pulses such as RF pulses, and/or adjusting positioning of a steerable antenna. The one or more sensors may communicate via a wired or wireless link.

In some versions, biometric parameters may be applied to dynamically adjust the performance of one or more sensors in order to optimize physiological recognition of independent human sources, and to reject other sources. The system may include a control processor in communication with the one or more sensors, the control processor communicating with the one or more sensors to adjust a detection control parameter of the one or more sensors based on an identification of a person or animal by the one or more sensors. The detection control parameters of the one or more sensors may include one or more of range gating, RF centre frequency, and RF power level.

In some versions, the system may include a control processor in communication with the one or more sensors. The control processor may be configured to activate a further sensor system based on an identification of a person or animal by the one or more sensors. The further sensor system may include a camera. Optionally, in the system a processor logs, or may log (e.g., record data, such as in a database in association with a person's identity), detected biometric characteristics based on the identification of a person to be a previously monitored person. In some versions of the system, a processor refrains, or may be configured to refrain, from logging detected biometric characteristics based on the identification of a person to be a not previously monitored person. In some versions, a processor may be configured to initialize biometric characteristic detection for a particular person. Optionally, a processor may compare newly detected biometric characteristics to initialized biometric characteristics to identify the person. The evaluation may include a comparison between newly detected biometric characteristics and initialized biometric characteristics.

Optionally, the evaluation may include classification of features determined from the signals. The features may include one or more of: a spectral peak ratio; a set up Optimiser flag vector; a peak trough ratio; a filtered respiration rate; a breathing variability measure; an in-band power of a sensor signal; a range of a sensor signal; a final respiration rate; a ratio of maximum to minimum amplitude of a breathing cycle; a high band power for a sensor signal; a mean respiration rate; a periodic leg movement activity detection; detection of turnover or turnover detection; and a post-processed movement.

Optionally, the evaluation may include classification of features determined from the signals where the features include one or more of a cardiac parameter, a galvanic skin response parameter, an exercise intensity parameter, a respiration parameter, a blood pressure parameter, a coughing parameter, a snoring parameter, a sleep parameter.

The evaluation may include a comparison of the determined features with historic features. In some versions, the evaluation may further include calculating mean and/or standard deviation values for a period of time from the determined features.

In some versions, one or more processors of the monitoring system evaluate(s) received data detected by one or more sensors from another monitoring system. The evaluation of the received data may include a determination of sensing equivalence between a plurality of health monitoring devices. Each monitoring device may include a setup classifier and a subject classifier, each configured to evaluate features from the signals to identify a person. The subject classifier may be further configured to evaluate historic features to identify a person. The health monitoring device or system may further include a camera sensitive to infra-red and an infra-red emitter. In some versions, one or more processors of the monitoring system, such as of the health monitoring devices, may be configured to detect an event from the signals and associate the event with a particular portion of a video taken with the camera including the event. The monitoring device or system may further include a battery and a coil for wireless charging of the battery.

In some versions, the one or more processors may be configured to control the one or more sensors to change sensor detection power, sensor frequency, sensor range gating or other control parameters for sensing, upon detection of biometric characteristics indicative of an animal. The one or more processors may be configured to access setting parameters for any one or more of light, sound and/or environmental appliances based on based upon identification of a person associated with the setting parameters. The one or more processors may be configured to trigger setting of any one or more of light, sound and/or environmental appliances with setting parameters associated with detected biometrics of the person identified.

In some versions, the system may include a central controller in communication with a collection of said sensors. The central controller may be configured to provide confirmation of location of identified persons within a structure. In some versions, the one or more sensors may include a night light. The one or more sensors may include an pass through outlet. The one or more sensors may include an AC plug for powering the sensor and an AC power pass through outlet. The one or more sensors may include a USB plug for powering the sensor and a USB pass through connection adapter. The one or more sensors may include a network interface for wireless or wired network communications.

In some versions, the one or more processors may be configured to set operation of a respiratory treatment apparatus based on the person identified. The set operation may permit therapy with the respiratory treatment apparatus. The set operation may change or changes therapy of the respiratory treatment apparatus.

Optionally, the one or more processors may be configured to re-train for identification of the person if biometric characteristics evaluated in the identification are treated by a respiratory treatment apparatus. The one or more processors may be configured to adjust operation of the one or more sensors upon determination of sensor signal quality. The one or more processors may be configured to rely on different biometric characteristics to identify the person depending on a quality assessment of detected biometric characteristics. The one or more processors may be configured to operate an enrolment process for initialization of a baseline of biometric characteristics for identifying the person. The enrolment process may include a guided breathing session or spontaneous breathing session. In some versions, the one or more processors is configured to reject a biometric characteristic involved in identifying the person when radio frequency interference is detected.

In some versions of the technology, one or more processors of the system may be configured to set operation of an alarm based on the person identified. The one or more processors may be configured to identify a main user from one or more other users. The system may be configured to track parameters of one or more users over time to build up classification features based on at least one of the one or more respiratory features, cardiac features, or movement features. In some such cases, at least one of the one or more respiratory features, cardiac features, or movement features includes at least one of the following respiration parameters: range, breath to breath variation, shape and inspiration verses expiration ratio.

Optionally, the one or more processors may be configured to classify a user's identity from features determined in the classification process. The classification process may include any one or more of a neural network, a hidden layer Markov model, logistic regression processing, linear kernel support vector machine, and radial kernel support vector machine. The classification process may include using Principal Component Analysis on the features, or feature set, prior to classification. The classification process may include real time features and offline features. The classification process may include multiple classifiers and late integration of the output, or the output of the classifiers, to produce an output posterior probability, such as a probability concerning the identity of a user or primary user.

In some cases, the system or method may include multiple sensors arranged for detecting the same or different persons, the system may automatically adjust parameters, such as sensing control parameters, of the multiple sensors, the parameters including at least one of: range, power, frequency, detection direction and radiation pattern.

Other aspects, features, and advantages of this technology will be apparent from the following detailed description when taken in conjunction with the accompanying drawings, which are a part of this disclosure and which illustrate, by way of example, principles of the technology. Yet further aspects of the technology will be apparent from the appended claims.

BRIEF DESCRIPTION OF THE DRAWINGS

Further example embodiments of the technology will now be described with reference to the accompanying drawings, in which:

In FIG. 9D, arrows with solid lines indicate an actual flow of information, for example via an electronic signal.

DETAILED DESCRIPTION

1. Background

Figure 1:
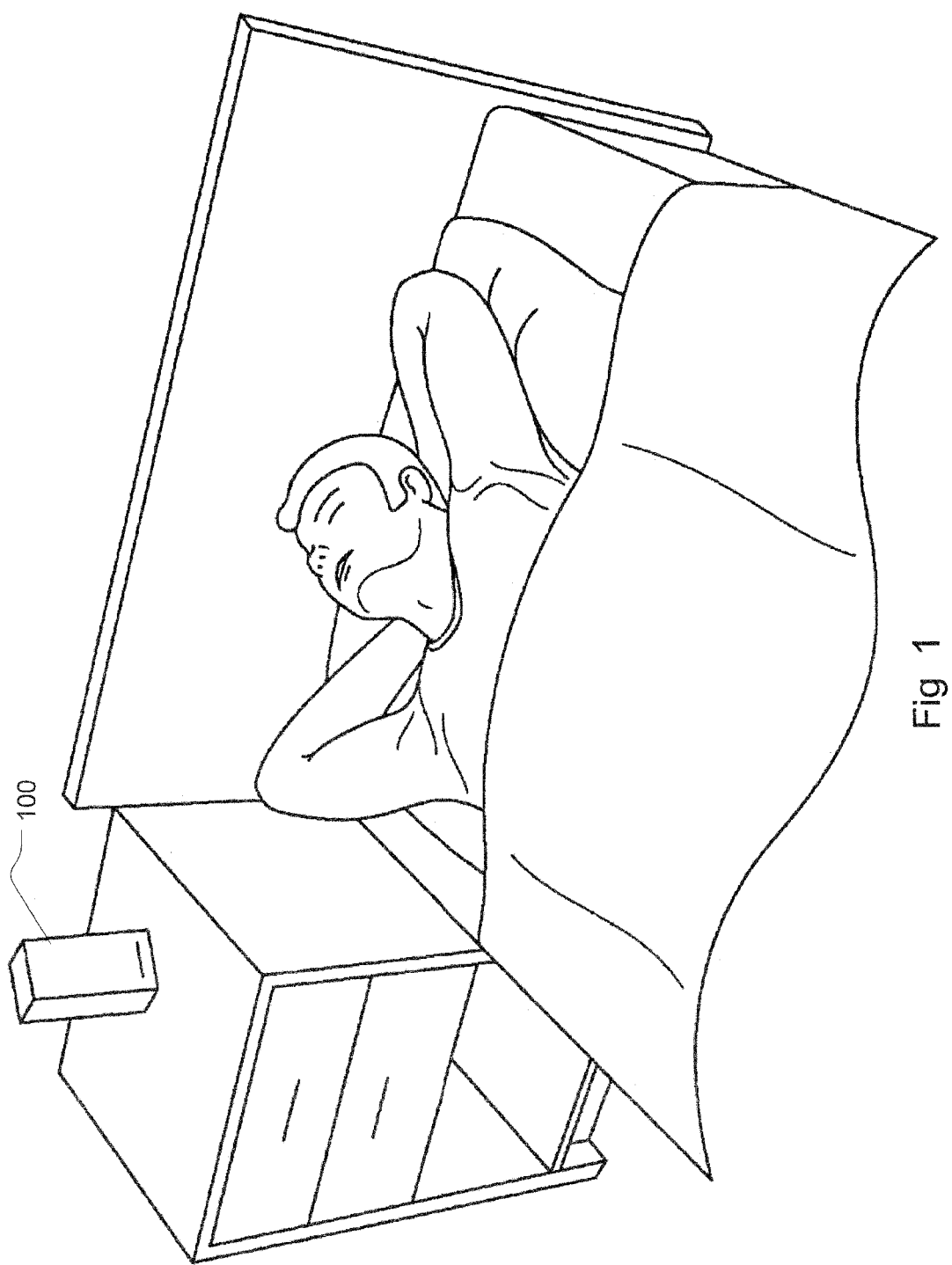
FIG. 1 is an illustration of an example detection apparatus suitable for implementation with a radio frequency sensor in some versions of the present technology.

Looking to the future of healthcare and personal health at the moment, three interlinking categories are evident: (i) the trend of collecting and monitoring data from our bodies, (ii) health budgets being under pressure, and (iii) the automation of medicine.

As people are becoming more health educated (from early adopters in the 'Quantified Self' movement), they are also living longer, and are demanding more of their physicians, and there is some evidence that the 'power curve' is shifting towards the consumer. For products in this space to be successful, they must attach themselves to a person's life and become indispensable. Prevention is much cheaper than cure, and health systems must move to outcomes based measures—closer to the ancient Chinese system where the doctor got paid for keeping somebody well, but not getting paid if the person got ill (i.e., in contrast to the typical way that medicine is paid for in the Western world).

The blurring of consumer and medical devices and services is leading to the automation of medicine, and the emergence of expert systems. Such changes are facilitating the ability to monitor chronic diseases in the home, as payers (e.g., insurers) may seek to bridge the funding gap, and to proactively manage hospital admission in a planned manner.

2. User Identity

Therefore, there is a need for systems that can identify user specific patterns (i.e., identifying the user, referred to here as a generic biometric "fingerprint") to avoid impersonation, and also to detect abnormal changes in the biometric and behavioral data of an identified user.

It should be noted that unlike a real human fingerprint or perhaps an iris scan, the "biometric fingerprint" referred to in this work is necessarily a fuzzier (less precise) estimate of a user's identity and includes both biometric and behavioral aspects. It is expected that such physiological and behavioral parameters will evolve over time for a user (e.g., as they get sicker, healthier, and go through other life changes).

The system outlined is intended to be capable of detecting user specific patterns. Examples of use include to authenticate a user, to potentially confirm compliance with a prescribed treatment and/or to authorize a payment or other incentive to improve or manage the user's health and fitness level or to encourage compliance with a therapy (e.g., to reduce an insurance premium or qualify for a payment or reduce a loading). In some cases, the detection of a specific user may be used to ensure that a current user, for whom biometric health parameters are being detected, is the same as a prior user, for whom health parameters were previously detected (e.g., between different sessions with a sensor). In such a case, an analysis of historically detected health parameters from multiple sessions may be confirmed to be for a single user without mixing detected health parameters from different users. Thus, sensor logging of detected parameters may be based on the biometric confirmation/authentication of a previously identified user.

The present technology concerns processes, such as with software algorithm(s), and systems for reading data from one or more sensors and services, processing the data, and adapting system parameters based on the newly collected data and on previously collected datasets. Some or all of these sensors gather physiological data readings from the end user of the system.

An example of such a software algorithm and system may include a smartphone with inbuilt sensors such as accelerometer(s) for step counting, compass(es), Global Positioning Systems (GPS) (positioning/location awareness), and heart rate spot measure monitors. Other example systems may include a smartwatch containing sensors such as accelerometers(s) (for measuring movement), heart rate monitors (e.g., using optical or other methods), galvanic skin response (GSR) measurement devices, blood pressure monitors (e.g., derived from a photoplethysmographic signal), and/or breathing sensors, e.g. based on the wireless RF biomotion sensors discussed above or herein).

Extra data can be gathered from the user by a 'Lab on chip' adhesive module via a radio link, or directly from the medication dispenser, e.g., via an identification chip such as RFID (radio frequency ID), or from a measuring device such as a spirometer (peak flow meter).

3. Detection of Physiological and Behavioral Information

In one embodiment a device can be placed beside the bedside (or within or under or over the bed, or worn by the user) that collects physiological parameters such as heart rate, respiration rate, respiration depth (e.g., shallow/panting or deep), degree of movement and other associated parameters while the user is in bed.

The system may operate continuously without the need for user input. For example, the device may have non-triggered operation such that the sensors are intended to be sensing (e.g., 24 hours 7 days a week) whether a user is near or not (e.g., all of the time). In this regard, a device, such as a range gated RF sensor, may continuously monitor a space (e.g., a bedroom), in order to distinguish between a main user and another user(s). The system may track parameters of the user(s) over time in order to build up a classification of features based on movement patterns and respiration (e.g., range, breath to breath variation, shape, inspiration vs. expiration ratio). Thus, the system may be configured for building classification features.

The system may lock onto a main (dominant) or primary user of the system over time, and build differential features. Additionally, the system may track user habits such as the side of a bed a user is sleeping in, and the time the user goes to bed each day of the week. The system may use a classifier, such as a neural network (e.g., a hidden layer Markov model), or for simpler implementation logistic regression to determine the classification features. Both offline and real-time subject classification features may enable the system to determine a probability of who is detected, the user or another user, such as the user's partner. The offline processing may also allow for re-training of the system based on real-time parameters that may be calculated/determined during sensing/monitoring sessions. In this regard, the real time classification may take place while a user is being sensed in the sensing range of the sensor. Offline processing, such as with offline parameters that may be calculated/determined after sensing/monitoring sessions, may take place when a user is no longer within the range of the sensor using previously sensed data. An offline feature (or multiple offline features) or offline parameters is/are the product of offline processing. For example, instead of having to calculate and/or classify based on very recent data ("real time"), an offline processing step allows a post hoc analysis of the entire monitoring/sensing session (e.g., night) or multiple sessions (e.g., nights). Such processing can occur, for example, after bed partners wake up and leave the bedroom/sensor area. This can give a broad view of all of the data for the night/sleep session(s). Real time features or real time parameters may be calculated and/or applied to classification with very recent data, such as during a particular sensing/monitoring session.

Other techniques such as linear kernel or radial kernel support vector machines (SVM), may be implemented for classification. Calculation of the features may be optimized by using Principal Component Analysis (PCA) "whiten" (i.e., reduce any redundant data, such as dimensionality data, prior to further processing) the feature set prior to classification where a large number of very similar features are used. Multiple classifiers may be used, with "late integration" of the output to form an output posterior probability.

When applied to multiple sensors, by detecting the same or different persons from multiple sensors (e.g., placed at either side of a bed), and sharing data over a network, the sensor parameters such as range, power, frequency, detection direction, and/or emitted radiation pattern can be adjusted automatically to support areas where a large number persons may be present, such as patients within a hospital ward. In this regard, emitted radiation pattern concerns the detection pattern or detection region (i.e., the three dimensional (3D) sensing space—including any rear lobes that may exist behind a sensor). Detection pattern can concern range and direction. Sensors can be adjusted to adjust their range (e.g., with near and far range gating), their emitted power level (which also has an impact on the range, as the SNR (signal to noise) even within the far range gate could be lower such that the effective further detection is much closer than before). Power can also relate to energy saving when there is no person in the sensing environment for low power/battery use. A radio frequency dielectric resonant oscillator (DRO), if used in a sensor, can consume significant power. Frequency can change for co-existence (e.g., avoiding interference) or different country's regulatory requirements. Automated detection direction allows for poor setup of the device (e.g., if not optimally pointed at first user, the system can auto-adapt to the actual proper setup without prompting the user to move it). For example, a sensor may have a reconfigurable antenna capable of modifying dynamically its frequency and radiation properties in a controlled and reversible manner.

Thus, the system may be configured to both detect and authenticate a user by detecting parameters of, for example, motion, respiration and/or heart rate, from a non-contact sensor such as RF.

For example, as illustrated in FIG. 1, some embodiments of the present technology may implement a sensing or detection apparatus 100 useful for detecting physiological characteristics of a user or patient in the vicinity of the apparatus. The sensor may be a standalone sensor or may be coupled with other apparatus, such as a respiratory treatment apparatus, so as to provide an automated treatment response based on an analysis of the physiological characteristics detected by the sensor of the apparatus. For example, a respiratory treatment apparatus with a controller and a flow generator may be configured with such a sensor and may be configured to adjust a pressure treatment generated at a patient interface (e.g., mask) in response to physiological characteristics detected by the sensor. An example respiratory treatment apparatus is described in International Patent Application No. PCT/US2015/043204, filed on Jul. 31, 2015, the entire disclosure of which is incorporated herein by reference.

A typical sensor of such an apparatus may employ a transmitter to emit radio frequency waves, such as radio frequency pulses for range gated sensing. A receiver, which may optionally be included in a combined device with the transmitter, may be configured to receive and process reflected versions of the waves. Signal processing may be employed, such as with a processor of the apparatus that activates the sensor, to derive physiological characteristics based on the received reflected signals.

Figure 2A:
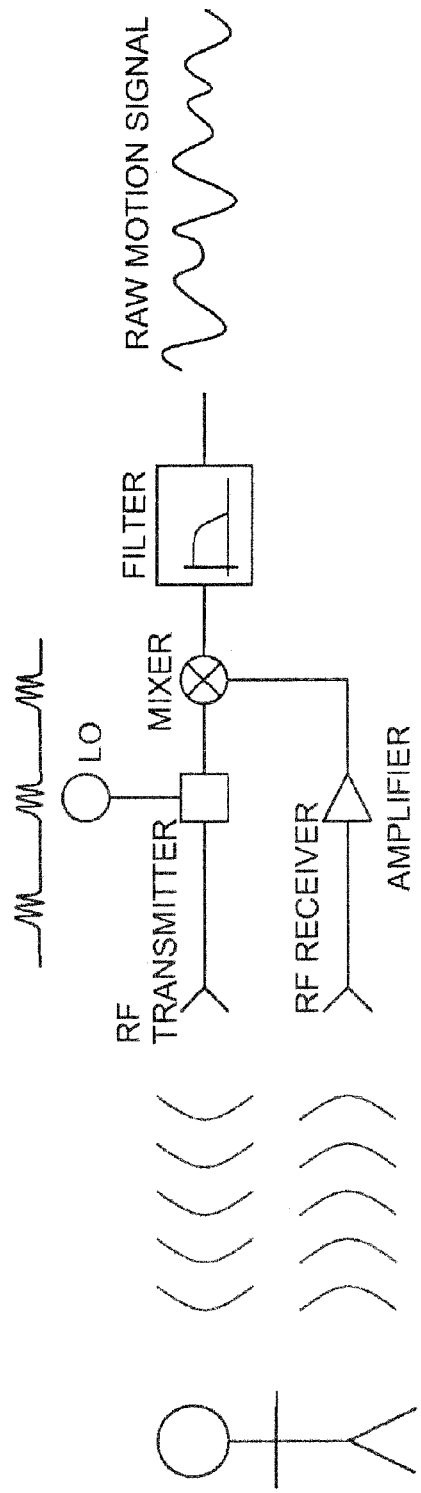
FIG. 2A is a diagram illustrating a conceptual structure and process flow for evaluation of sensor signals suitable for some versions of the present technology.

For example, as illustrated in FIG. 2A, the transmitter transmits a radio-frequency signal towards a subject, e.g., a human. Generally, the source of the RF signal is a local oscillator (LO). The reflected signal is then received, amplified and mixed with a portion of the original signal, and the output of this mixer may then be filtered. The resulting signal may contain information about the movement, respiration and cardiac activity of the person, and is referred to as the raw motion sensor signal.

Figure 2B:
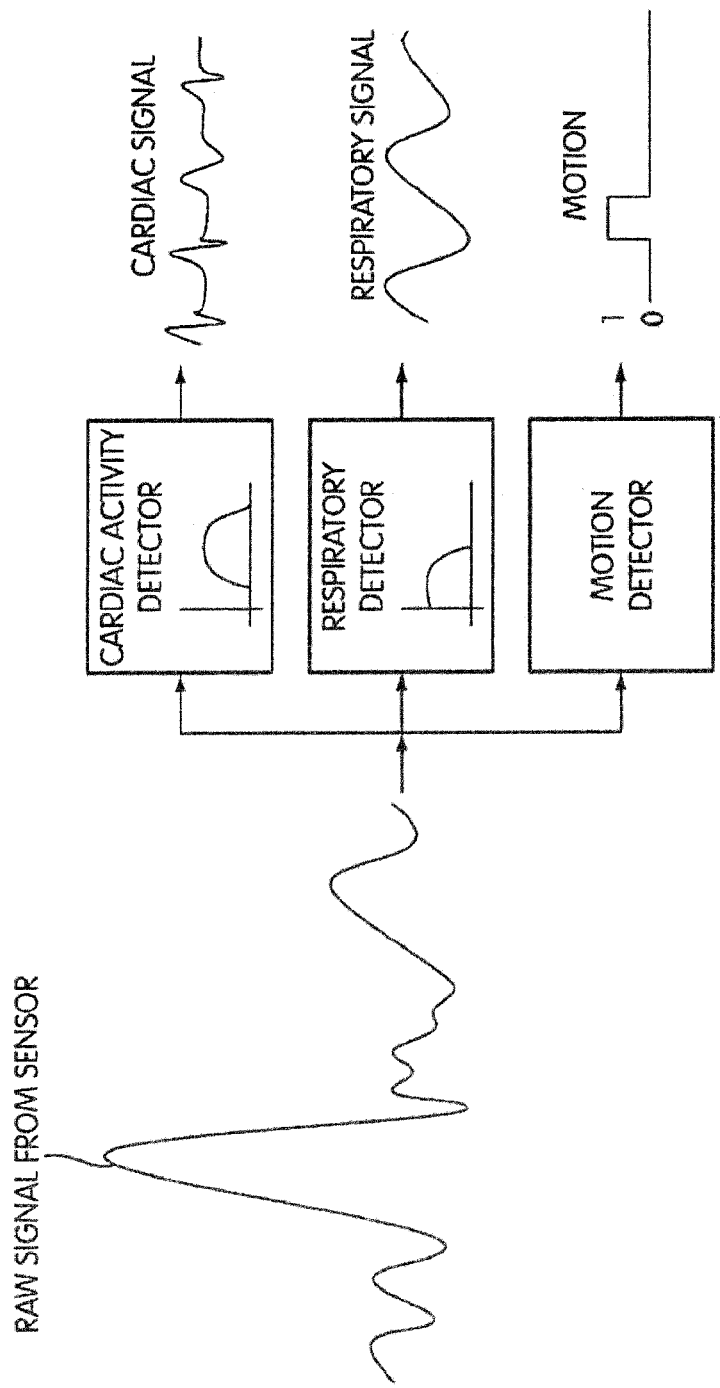
FIG. 2B is a depiction of further processing of sensor signals for the detection of example physiology indicators.

FIG. 2B is a diagram illustrating some potential processing of the raw sensor signal to produce indicators of the physiological characteristics. The raw signal will generally contain components reflecting a combination of bodily movement, respiration, and cardiac activity. Bodily movement can be identified, for example, by using zero-crossing or energy envelope detection algorithms (or more complex algorithms), which may be used to form a "motion on" or "motion off" indicator. For example, such movement detection algorithms may be implemented in accordance with the methodologies disclosed in U.S. Patent Application Publ. No. 2009/0203972, the entire disclosure of which is incorporated herein by reference. The respiratory activity is typically in the range 0.1 to 0.8 Hz, and can be derived by filtering the original signal with a bandpass filter with a passband in that region. The cardiac activity is reflected in signals at higher frequencies, and this activity can be accessed by filtering with a bandpass filter with a pass band of a range from 1 to 10 Hz.

Such a respiration and movement sensor may be a range gated RF motion detector. The sensor may be configured to accept a DC power supply input and provide four analog motion channel outputs with both in-phase and quadrature components of the respiration and movement signals of a person within the detection range. In the case of a pulsed RF motion sensor, range gating can help to limit movement detection to only a preferred zone or range. Thus, detections made with the sensor may be within a defined distance from the sensor.

By way of further example, the types of sensors used could be radio frequency RF based, e.g., ResMed's SleepMinder non-contact sensor family using at least some of the technology described in the above mentioned McEwan and McMahon patent documents. The measurement and data processing technology described in the international publications WO2010/036700, WO2010/091168, WO2008/057883, WO2007/143535 and WO2015/006364, which are incorporated herein by reference, could also be used. Furthermore, alternative technologies using an accelerometer, piezoelectric or UWB (RF Ultra Wide Band) mattresses, passive infra-red, or other optical means such as a camera with skin colour and movement detection, could also be used. For example, the device may implement movement detection algorithms or sensor technologies in accordance with any of the methodologies and sensors disclosed in any of U.S. Patent Application Publ. No. 2009/0203972, International Patent Application No., PCT/US14/045814; U.S. Provisional Patent Application No. 62/149,839, filed Apr. 20, 2015, and U.S. Provisional Patent Application No. 62/207,670, filed on the same date herewith, the entire disclosures of which are each incorporated herein by reference. Moreover, any of the radio frequency sensors described in U.S. Provisional Patent Application No. 62/205,129, filed on Aug. 14, 2015 may be implemented in any versions of the present technology, the entire disclosure of which is incorporated herein by reference.

A microphone may also be used to monitor and classify sound patterns consistent with breathing rate, chronic cough or snore, and separate these from background noises such as fans, road noise and similar. This is referred to as "Nighttime sleeping" monitoring, although could also be performed during daytime naps for instance; it is targeted at the user in their sleeping environment. Further, breathing rate and heart rate, and other such physiological signals, may also be detected using alternate sensors, such as those based on non-contact or contactrelated technologies.

When the user is out of bed, their physiological parameters can optionally be monitored by a body worn sensor. For example, this could be a clip based device, stick on patch (dermal or lab-on-chip) or wristwatch style device; the sensor parameters collected include some or all of movement and steps (via an accelerometer), location, galvanic skin response (GSR), heart and breathing rate (by optical, electric or movement means) and other associated parameters. This is referred to as "daytime/waking monitoring", and it is targeted at the user in their waking activities. Such devices could be in an earclip, watch or wristband form factor, such as a FitBit, Basis, Apple, Withings or other product.

Biometric data from one or more sensors may also be fused with video/camera image data in order to further increase confidence in the detection of "liveness", i.e., a live human or to identify a particular user, using techniques such as facial recognition, skin colour detection, and/or microblush detection. Such fusion of data may add another factor to the analysis. For example, skin color detection may be used as a first step in facial recognition, gesture recognition, and other applications, and is quite robust to scaling, rotation and occlusion.

In some embodiments breathing rate during the day and/or night may be captured by a wearable breathing sensor, such as an accelerometer clipped to the belt or bra, a chest-band (e.g., the spire.io device), a nasal cannula, or extraction of the waveform from a PPG (photoplethysmography) signal. Such data may also be involved in the biometric identifications described herein.

It is noted that it may be possible to combine pressure and other data from implantable devices (i.e., implanted within the person being monitored) with values collected by the system. Furthermore, it is possible to correlate baseline data collected outside the bedroom. Thus, data from one or more sensors may be evaluated in a biometric confirmation/identification of a person/user such as by establishing a baseline of detected biometric data attributable to a particular user and/or comparing newly detected data to previously collected data to confirm that the newly detected data is attributable to the particular user. Thus, the system may compare current parameters to historical parameters.

The system may aggregate and/or combine the data from the contact sensor recordings (e.g., recordings from body worn sensors,) and non-contact sensors (e.g., Doppler, RF sensors) as well as the video/camera image data from video detection systems. Therefore, the system may be capable of a collective 24/7 operation, or parts thereof to suit the lifestyle of the user.

The algorithms and methodologies described herein may be implemented in one or more processors such as on a computing device (e.g., a PC, server, cloud service, smart device app or variant) with access to a database storage device. The algorithm may be based on a classification system analyzing one or a multitude of data sources, and can draw on historical data stored in the database. The rule thresholds, templates and/or stored models can be varied based on adaptive probabilistic weightings based on both user specific and population based demographic data.

3.1 Sensor Feedback

The system may provide a feedback loop to the user or to a third party (e.g., via a PC or smart device such as smartphone or tablet), and optionally to a monitoring centre for review, authentication and optional intervention. The system may also provide feedback to therapeutic effect of therapy devices, such as continuous positive airway pressure (CPAP), adaptive servo ventilation (ASV) and/or bilevel positive airway pressure (bilevel) machines used to assist a user with various respiratory issues. Such devices are described in more detailed herein.

In some embodiments a sensor maybe integrated with or into a respiratory treatment apparatus such as a CPAP device such as a flow generator or similar (e.g., a Respiratory Pressure Therapy Device (RPT) or may be configured to communicate together. For example, upon detecting the biometric of a person undergoing therapy, the system may cross check that the expected user of the system was receiving the correct therapy. Accordingly, the system may optionally be enabled to reconfigure the therapy of the PAP device to expected machine parameters (pressure or flow protocols etc.) in, for example, a CPAP, ASV, or bilevel machine based on the identification. The system may also flag an alert to a monitoring centre and/or to a user if the expected person (e.g., a previously detected and identified user) cannot be identified. An example of such a treatment apparatus is described in more detail previously and in the trailing sections of this specification.

Similarly, when an expected biometric is detected, the respiration rate and heart rate of the subject may be utilised by the system to better adapt therapy to the specified user. For example, upon detecting an elevated heart rate, the system may enter a specific breathing curve to a device providing a respiratory assistance, in order to reduce the heart rate to within an expected range.

In some embodiments, when heart rate feedback for CPAP, bilevel, ASV or other therapy is received, it may be possible to track an increase in heart rate, track an increase in irregular variation in heart rate (which may be indicative of arrhythmia), and/or to track long term trends in heart rate dynamics and breathing rate dynamics, both when therapy is in use and not in use.

In this way, it is possible to provide feedback to a monitoring server.

In an occupational health setting, such biometric data may reduce and/or prevent abuse of a monitoring system. For example, miners or truckers might have sleep disordered breathing screening, diagnostics, monitoring, and sleep quality analysis equipment installed in their living quarters or bunk (e.g., in vehicle cab/berth). Some types of sensor may be placed on the bed rather than beside, above or under the bed. By assuring the particular subject/user is in fact being monitored with the biometric identification described, the monitoring information could be fed to a central system such as a rostering system (i.e., assuring all users are sleeping in their assigned bunk,) and may, for example, be implemented to ensure sufficient sleep is being obtained by the intended/identified person. In this regard, the system may detect who is sleeping in a bunk and track their sleep quality, with reference to a fatigue management system. In one example, a user might have sleep apnea, but not be compliant with their treatment (e.g., not wearing CPAP mask). As such, the system may issue an alert that the user is at increased risk (especially if they are required to use therapy for occupational health and safety reasons). In some embodiments the system may require permission from a user or operator of the system prior to tracking and/or identifying a user.

Generally, in some versions, once sensed biometric data has been identified (e.g., by a classified "fingerprint") as belonging to a particular person, it may be stored, such as in a database, in association with the identity of the person.

During the daytime, professional drivers and/or operators of heavy machinery or others in safety critical applications (e.g., air traffic controllers) could be monitored using physiological sensors such as the Plessey EPIC capacitive sensor, radar or wearable devices.

Example collection of "waking" and "sleeping" data is described below. The signal collection methods from "waking" may be applicable to "sleeping" and vice versa.

4. "Waking" Time Data Collection

An example of how information can be utilized by the system is as follows:

4.1 Heart Rate a. Heart rate (HR) data is gathered from the user on a continuous or semi-continuous basis. This may be via a chest band (e.g., a sports monitoring band such as provided by Polar), or a wrist watch implementing heart rate monitoring (e.g., the Basis watch, ambulatory ECG, photoplethysmogram, ballistocardiogram or similar). Ideally, a low user impact device is used, such that it is suitable for daily monitoring over a long period of time (e.g., days, months or years).

b. The HR data is analyzed to product heart rate variability (HRV) estimates.

c. Recorded HRV parameters (such as short term and long term fluctuations in rate) are compared to historical parameters and demographic (expected) parameters for normal and chronically ill subjects, and features are provided to the classifier. In addition, a smoother version of the HRV may be utilized, based on low pass filtering of the signal; this is primarily used for analysis of longer term fluctuations, and comparison to detrended versions.

4.2 Galvanic Skin Response a. Galvanic skin response (GSR, also known as electrodermal response) can be recorded by a wearable device (e.g., the Basis watch, or other commercially available GSR measurement devices).

b. The GSR signal is used as a surrogate measure of sympathetic "fight or flight" activation.

c. Combining the extracted GSR and HRV signals yields an estimate of the ratio between sympathetic and parasympathetic activation. This balance of sympathetic to parasympathetic activity is used as an estimator of normal vs. disease progression state (e.g., increased sympathetic activity with decrease in parasympathetic activity) by the system.

4.3 Exercise Intensity a. The variation in exercise intensity and duration is captured from the 'daytime' sensors, recorded to the database and analyzed for specific trends and variations.

b. Am overlaid model of circadian rhythm/sleepiness may show distinct patterns of periods of activity and stillness throughout the day (e.g., an increase in activity for an office worker during such times as after getting out of bed, then commuting, then in the early morning, for coffee breaks, walking to meetings, a lunchtime stroll, followed by sleepiness in the afternoon lull [strongest sleep drive typically occurring between 1 pm and 3 pm], the activity during breaks, commuting home, a reduction in activity in the evening during reading/watching TV, and further significant reduction during sleeping time [strongest sleep drive typically occurring between 2 am and 4 am]).

c. Energy expenditure may be estimated by combing heart rate and GSR data in conjunction with a step counter. Alternatively, a standalone step counter (pedometer)

can be used as a surrogate of exercise intensity (e.g., using a Nike Fuel band, FitBit, Jawbone Up or similar wearable device).

4.4 Respiration Parameters a. Respiration rate, depth and activity (described below in "sleeping" section)

4.5 Blood Pressure Parameters a. Derived from a wearable photoplethysmography based sensor 5. "Sleeping" Time Data Collection An example of how 'sleeping monitoring' information is utilized by the system is as follows:

5.1 Respiration Rate, Depth and Activity (Movement) Levels

An algorithm is implemented to detect patterns in the breathing (respiration) rate and dynamics of a user. The algorithm can adaptively track the baseline respiration rate, movement characteristics and breathing waveform shape of a person over days, weeks, months and/or years to build up a profile of their respiration dynamics.

The algorithm module creates an adaptive baseline for a user, and looks at breathing rate parameters such as median, mean, interquartile range, skewness, kurtosis, min and max breathings rates over a period of time (e.g., 24 hours), and is primarily (but not exclusively) targeted at the times when a person is asleep. In addition, the inspiration/expiration waveform shape, and short, medium and long term breathing fluctuations are tracked. The baseline fitness of the user may also impact these readings.

There is some overlap with the activity detection performed in the 'waking' monitoring, as a group of algorithm processing steps and associated digital signal processing for determining physiological repetitive and varying motion, including that caused by the movement of chest due to respiration, sway detection, and cancellation, roll over in bed, and gross and fine movement detection due a multitude of actions including scratching (e.g., due to physical irritation or discomfort) are processed.

5.2 Heart Rate

Heart rate can also be estimated in the 'nighttime' bedroom setting from a contact (e.g., wearable device such as the Basis watch using optical methods or ECG electrodes and device) or from non-contact sensors such as the SleepMinder, using techniques such as wavelet based time-frequency transforms (derived from the Ballistocardiogram signal—the mechanical movement of the heart detected noninvasively from the skin surface).

5.3 Coughing and Snoring

Utilising the digital sampling of an audio signal recorded via a microphone, the algorithm is capable of detecting the characteristic patterns of snoring, snuffling, coughing or breathing difficulties. This is implemented using a digital filter bank, frequency decomposition, and search for 'bursty' noise, i.e., a 'cough signature' using spectral analysis, or using morphologic processing These events are optionally cross correlated to the movement and respiration patterns.

6. Signal Processing

For one exemplar realization of in-bed monitoring, the invention analyses two channel (in phase I and quadrature Q) signals recorded by a radio frequency RADAR that have been digitised using a suitable ADC module. These RF signals can be continuous wave or pulsed (e.g., applied to ResMed's SleepMinder 5.8 GHz and 10.525 GHz sensor, devices utilizing FMCW methods, or others). In some cases, the sensor may be a sensor described in U.S. Patent Application Publication No. 2014/0024917, the entire disclosure of which is incorporated herein by reference. The signals are fed into a filter bank, whereby a series of digital filters including band-pass filtering are applied to detect and remove low frequency sway information. The phase information in the two channels is compared to produce a clockwise/anti-clockwise pattern. Hysteresis and glitch detection is applied to suppress signal foldover, and the resulting signal represents the relative direction of the movement source to the sensor frame of reference. Peak/trough detection and signal following is additionally used to aid this processing. Therefore, the system can determine if a movement is moving towards or away from the sensor, and if changing direction.

Calculation of spectral content of signal is performed using a Fast Fourier transform and find peak (frequency domain) or via time-frequency processing such as using the discretized continuous wavelet transform, appropriate basis selection, and peak find. The residual low frequency components may also be processed to determine longer timescale trends.

Patterns of sleep disordered breathing, including cyclical or periodic patterns such as Cheyne-Stokes Respiration can provide aspects of user recognition, in addition to triggering a worsening of condition. It should be noted that if such SDB episodes are detected, a system aware of the subsequent application of a therapy such as CPAP could automatically retrain to be aware of the changing biometric (i.e., identify verification pre and post CPAP therapy intervention). Thus, the system may recalibrates/retrains the identification process if a disease condition affecting breathing/cardiac/movement activity is treated.

Cardiac patterns such as atrial fibrillation and flutter (including paroxysmal), ventricular tachycardia and others can also provide aspects of the recognition of identity. In such cases, inputs to the system relating to therapies can reduce identify detection failures if the user seeks treatment for their arrhythmia.

7. Creating the "Fingerprint"

A critical aspect of processing the possible multitude of input signals is a robust estimator of signal quality for each. Just as it is desirable to estimate a biometric "fingerprint" of a user, and to track and capture the evolution of this biometric marker from healthy to sick, it is recognized that signals may be of poor quality, corrupt, or manipulated in an undesirable manner (i.e., tampered with). The poor signal quality is not necessarily caused by interference between sensors. For example, a wearable heart monitor may have inadequate contact with the body, resulting in an unusable or misleading signal. Correlation and comparison to data from other simultaneously worn movement sensors can aid the distinguishing of intermittent poor signal due to body movement (e.g., potentially expected signal corruption due to the movement confounding the other sensor(s)) versus longer periods of suspect signal quality due to poor positioning of a sensor.

A user might decide to try to deceive a step counter into giving an artificially high reading by placing the counter on some other artificial or natural movement source, other than the user themselves. The time varying statistics of the detected movement and/or other parameters can be used to distinguish from the predicted biometric "fingerprint" of the user and flag invalid or tampered values.

The system for managing the pattern recognition process can accept multiple input parameters, and assumes that quality estimator has been executed to discard or flag any poor quality data. It is recognized that the input data may be dimensionally redundant, and that a process such as randomized PCA (principal component analysis) can be applied to reduce any such redundancy prior to further processing.

Figure 3:
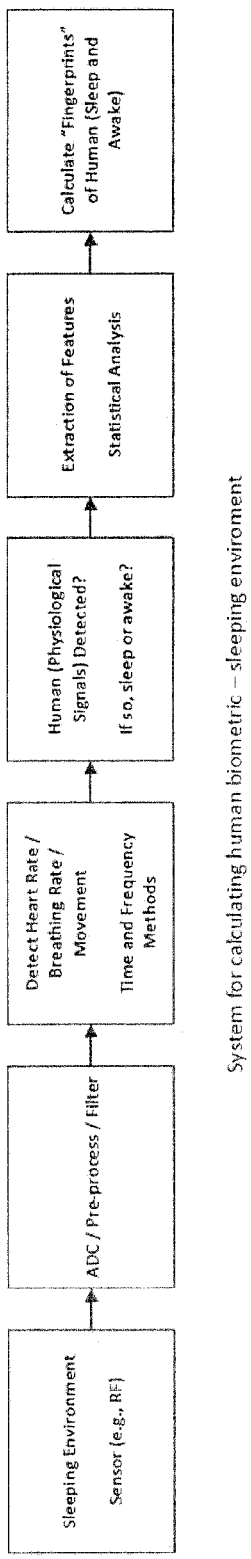
FIGS. 3 and 4 shows a diagram illustrating a processing system and flow for calculating human biometric(s) for sleeping and daytime respectively.

FIG. 3 outlines a system for calculating a human biometric (or multiple biometrics) in the sleeping environment. For analogue sensors, the data are digitised by an ADC; for digital sensors, signals may be used directly. Pre-processing such as filtering of noise sources (e.g., mains 50/60 Hz) using band pass filtering is performed. Heart rate, breathing rate, and movement/activity is extracted using time frequency methods (such as by using short time Fourier analysis or wavelet analysis). Thus, the presence of a motion and breathing signal (physiological signal) in the sleeping environment is detected by a field sensor such as a range gated motion sensor module (or other types of sensor such as piezo based mattress sensors or wrist-worn sensors etc.). Sleep staging is then performed on the decomposed motion signal containing the physiological signals. The biometric features are extracted, and the "fingerprint"/biometric is estimated, and classified as human or not, whether the human is previously known to the system. Behavioural data can include long term trends in sleep duration (e.g., typical long term trends in weekday/weekend variation), go to bed times (weekday/weekend), sleep efficiency, number of awakenings, time to sleep (sleep onset latency), percentage of REM and deep sleep, and so forth—where these are impacted by the behaviour of the user, such as by voluntary sleep restriction, socializing at the weekend.

Figure 4:
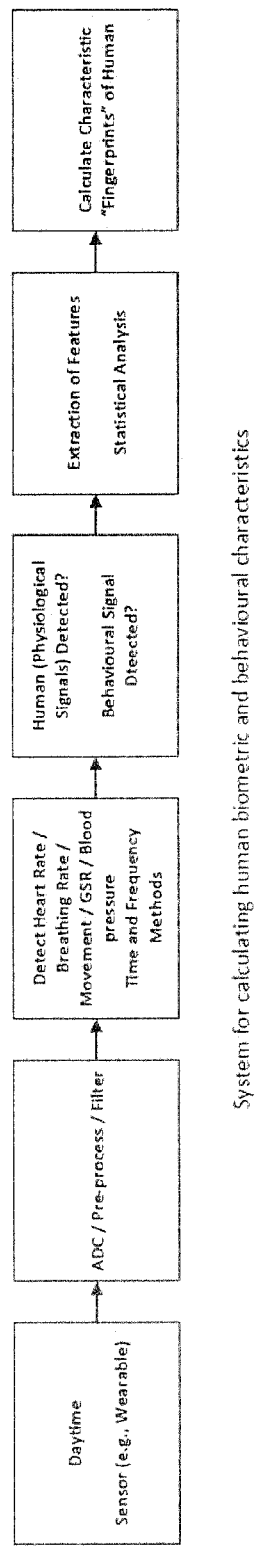

FIG. 4 outlines a system for calculating human biometric characteristics from physiological parameters and optionally by combining behavioural characteristics (e.g., patterns of daytime activity, location, spikes or changes in heart rate/respiration rate at particular times of the day). A daytime signal may contain both physiological signals as well as behavioral data. It can be seen that sleep time and daytime detection can be combined or considered separately, depending on the available sensors and desired use case.

Figure 8:
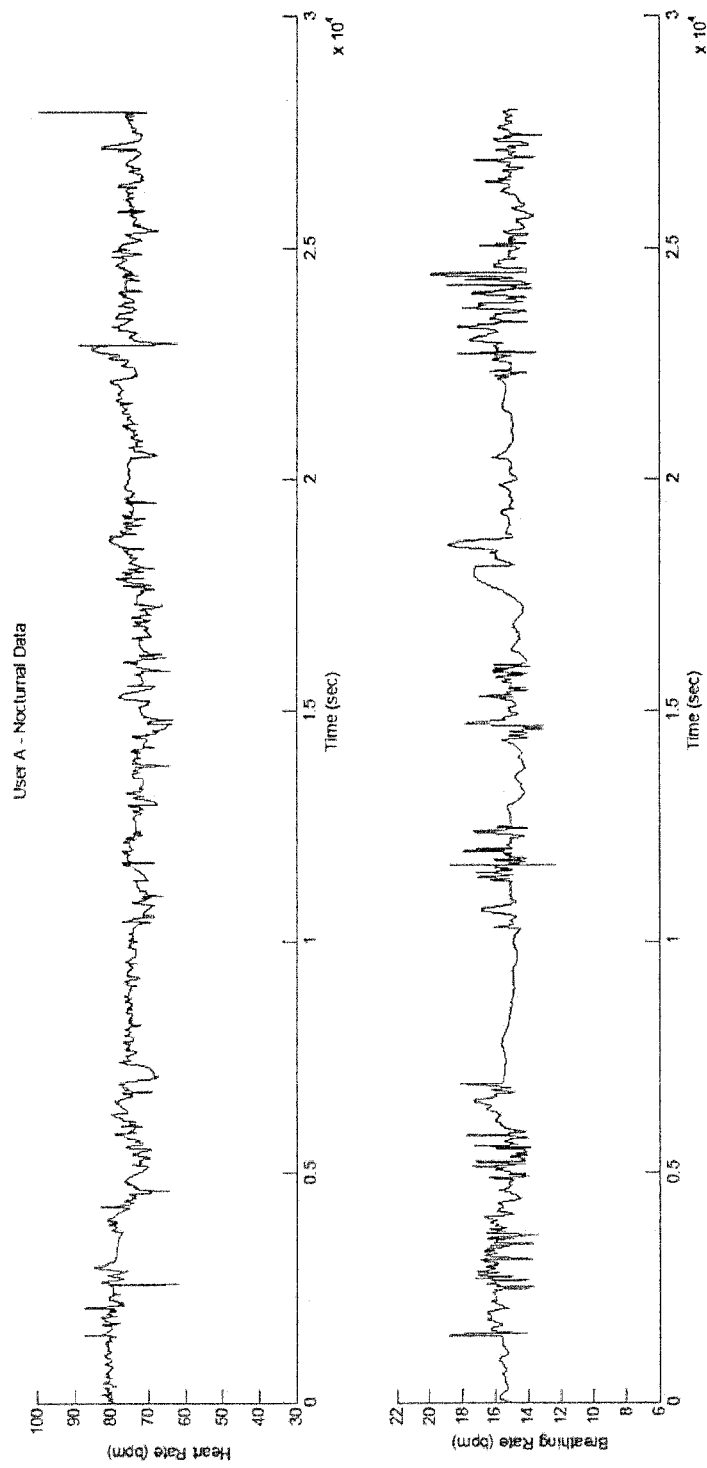
FIG. 8 illustrates signals of heart rate and breathing rate for a subject "User A" during a sleep session (approx. 8.3 hours), recorded using a non-contact pulsed continuous wave RF sensor at <0.8 m distance.
Figure 9:
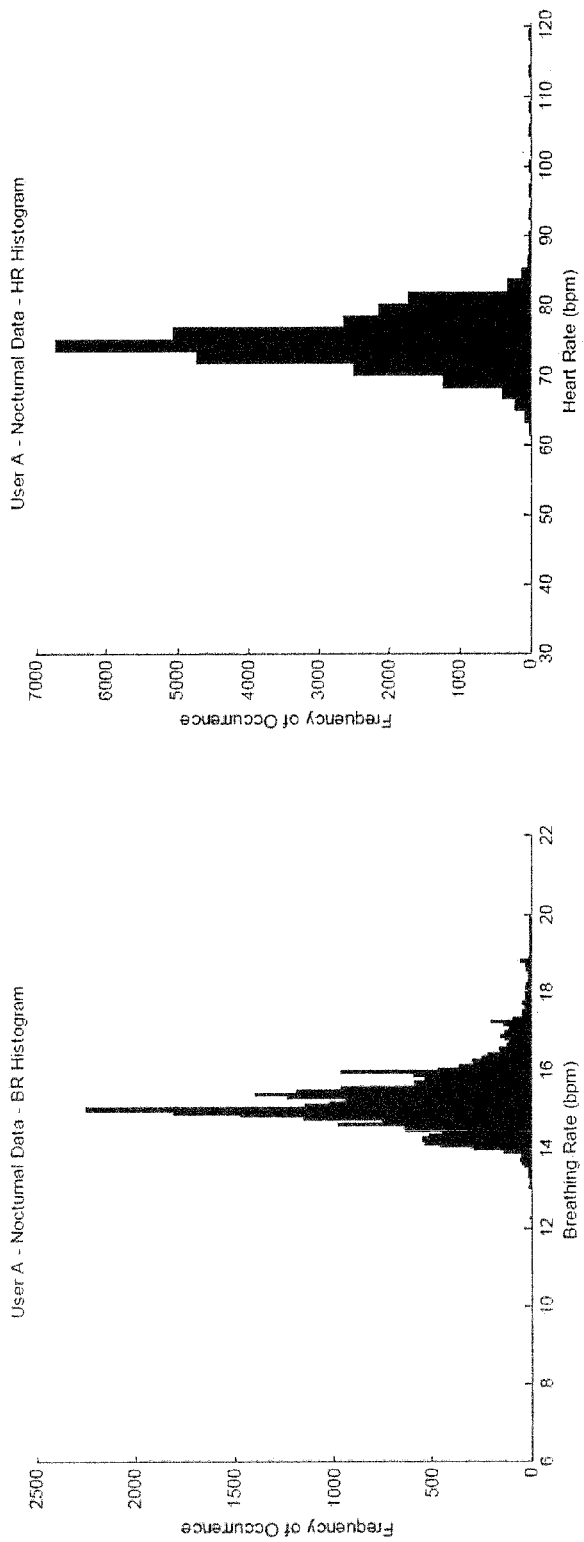
FIG. 9 illustrates heart rate and breathing rate histograms for a subject "User A" of FIG. 8 during a sleep session (approx. 8.3 hours), recorded using a non-contact pulsed continuous wave RF sensor at <1.8 m distance.
Figure 10:
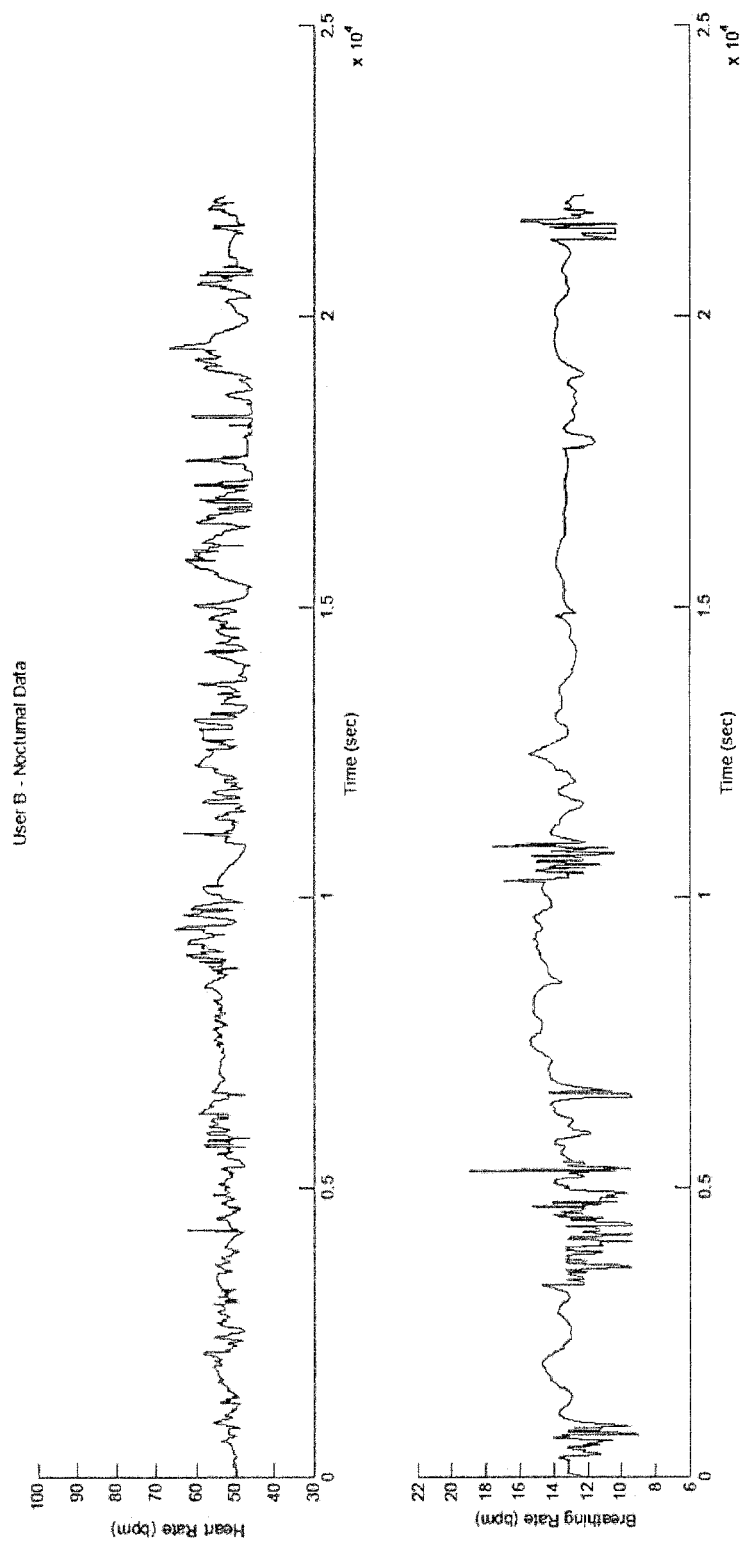
FIG. 10 illustrates signals with heart rate and breathing rate for a subject "User B" during a sleep session (just over 6 hours), recorded using a non-contact pulsed continuous wave RF sensor at <1.8 m distance.
Figure 11:
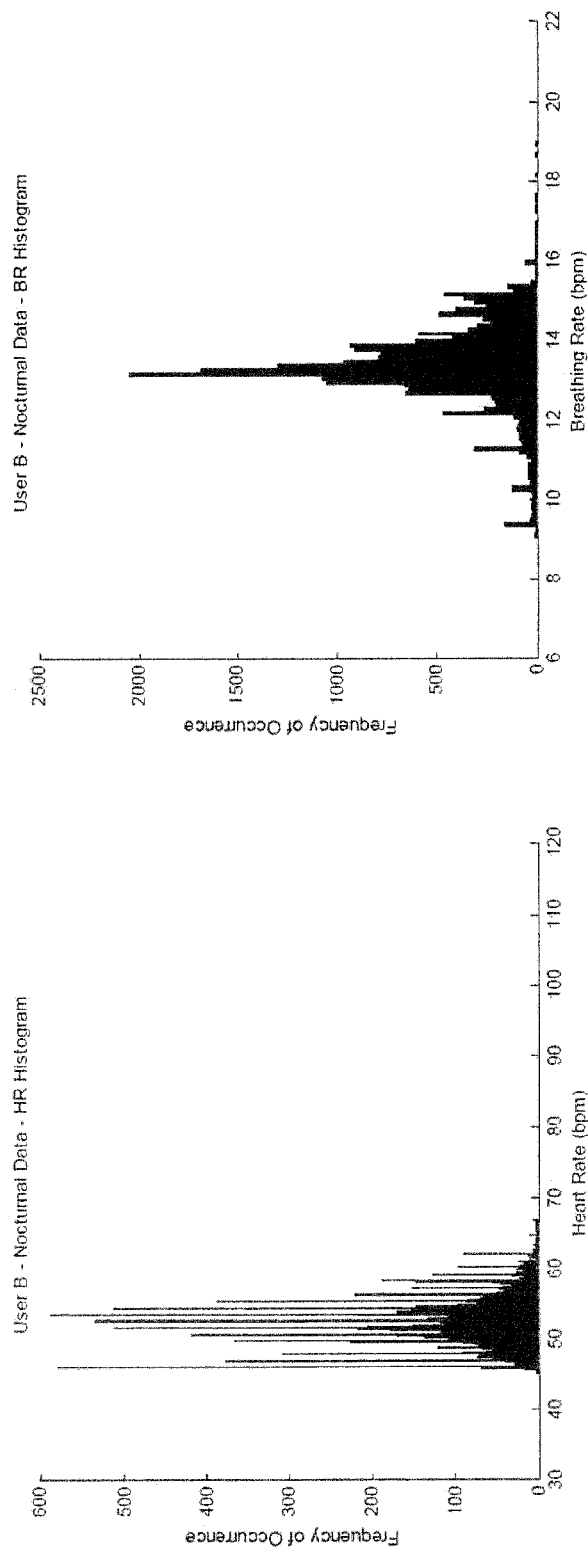
FIG. 11 illustrates heart rate and breathing rate histograms for a subject "User B" of FIG. 10 during a sleep session (approx. 8.3 hours), recorded using a non-contact pulsed continuous wave RF sensor at <1.8 m distance.

FIG. 8 illustrates signals of heart rate (upper panel) and breathing rate (lower panel) for a subject "User A" during a sleep session (approx. 8.3 hours), recorded using a non-contact pulsed continuous wave RF sensor at <1.8 m distance. FIG. 9 presents the associated heart rate and breathing rate histograms for "User A". FIG. 10 illustrates signals with heart rate and breathing rate for a different subject "User B" during a sleep session (just over 6 hours), and associated heart rate and breathing rate histograms in FIG. 11. Such signals may be evaluated by the processing of the present technology.

Figure 5:
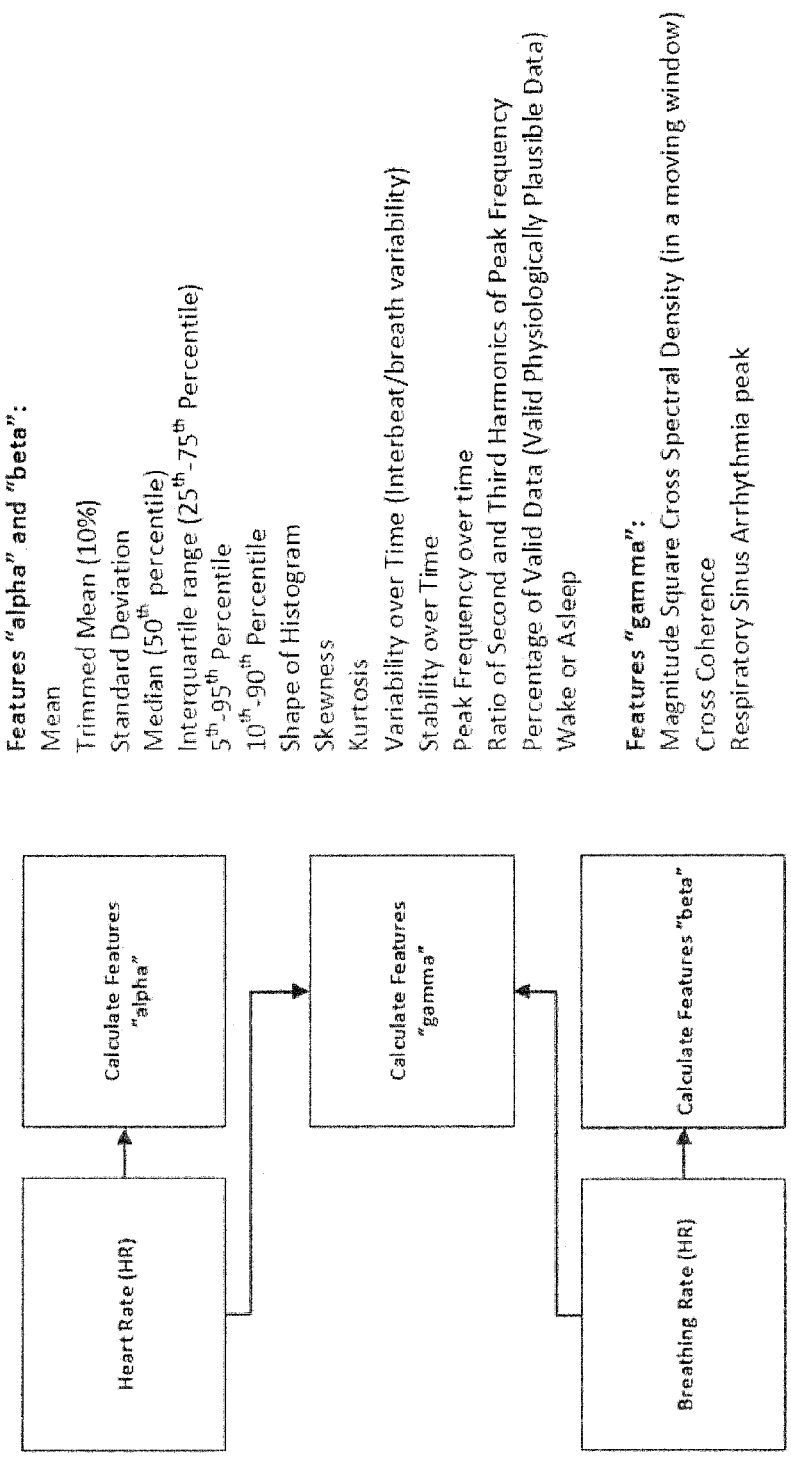
FIG. 5 illustrates processing for calculation of characteristic features in order to generate a biometric fingerprint.

For example, FIG. 5 illustrates processing for calculation of characteristic features in order to generate a biometric fingerprint. User recognition may be made by distinguishing biometric parameters that are input to a user classifier (see e.g., FIG. 5 which can calculate and combine features from cardiac and respiratory signals for such a purpose). Optionally, if a good quality HR (heart rate) is not available/detected, the system can fallback to BR (breathing rate) for some or all of the processing period under consideration; Thus, a system may rely on different biometric characteristics to identify a person depending on quality of detected biometric characteristics. Any of the features (e.g., two or more) illustrated in FIG. 5 or identified below may be evaluated as part of a biometric fingerprint:

Breathing/Respiration Signal Related Parameters
  Variability of breathing rate throughout the day and/or night (the variability being characteristic of the user)
  This can be interbreath or over longer timescales—e.g., 30, 60, 90 sec or much longer periods)
  The stability over time (related to the variability)
  The standard deviation of breathing rate
  The depth of respiration (shallow, deep etc.), and relative amplitude of adjacent breaths
  The mean or average value of the breathing rate
  The trimmed mean (e.g., at 10%) to reject outliers
  Wake or Asleep (i.e., the sleep state of the user as detected)
  Surges (sudden accelerations or decelerations) in breathing rate seen during quiet periods and during REM sleep
  Median (50th percentile)
  Interquartile range (25th-75th Percentile)
  5th-95th Percentile
  10th-90th Percentile
  Shape of Histogram
  Skewness
  Kurtosis
  Peak Frequency over time
  Ratio of Second and Third Harmonics of Peak Frequency
  Percentage of Valid Data (Valid Physiologically Plausible Data)
  Autocorrelation of the individual signals
  Characteristic patterns in the spectrogram
  Wake or Asleep
  Relative percentage of REM and deep sleep
Cardiac/Heart Signals
  Heart rate variability (inter beat (e.g., as derived from the Ballistocardiogram) and over longer defined moving windows—e.g., 30, 60, 90 sec) i.e.,
  Variability over Time (Interbeat/breath variability))
  Mean
  Trimmed Mean (10%)
  Standard Deviation
  Median (50th percentile)
  Interquartile range (25th-75th Percentile)
  5th-95th Percentile
  10th-90th Percentile
  Shape of Histogram
  Skewness
  Kurtosis
  Stability over Time
  Peak Frequency over time
  Ratio of Second and Third Harmonics of Peak Frequency
  Percentage of Valid Data (Valid Physiologically Plausible Data)
  Wake or Asleep
  Autocorrelation of the individual signals
  Characteristic patterns in the spectrogram
Cardiorespiratory Signals
  Magnitude Square Cross Spectral Density (in a moving window)
  Cross Coherence
  Respiratory Sinus Arrhythmia peak
  LF/HF ratio to indicate autonomic nervous system parasympathetic/sympathetic balance
  The cross correlation, cross coherence (or cross spectral density) of the heart and breathing signal estimates
  The characteristic movement patterns over longer time scales, i.e., the statistical behavior observed in the signals.
  Patterns of movement during detection of and comparison of these heart and breathing signals (e.g., during sleep, some users may have more restful and some more restless sleep)

For example, a reference distribution of movement and/or other features may be compared to a calculated distribution, and a test such as a non-parametric Kolmogorov-Smirnov goodness of fit may be performed as a comparator for a defined enrolled histogram of variability. Extraction of the parameters can be achieved using time frequency analysis techniques (such as STFT or wavelets).

While no single parameter may allow distinguishing of users (e.g., mean heart rate or mean respiration rate at rest or in a specific sleep stage such as deep sleep), a more advanced system may combine multiple features and thus an early integration approach is favored whereby the group of features are fed into a classifier. If training data (labelled data) are available, a supervised classification system can be employed, whereby a large training dataset is provided to the system to produce model parameters. Data from the first use (day or night signals) can be fed back to update a user specific classifier in order that the biometric "fingerprint" be increased in user specific accuracy. This could be achieved via an enrollment step, whereby a sample acquired template is stored in a database. Subsequently, a matching step is performed to verify an identity. Where there is a paucity of such detailed training data, a semi-supervised or unsupervised learning feature hierarchy (e.g., deep learning) approach with techniques such as sparse coding (e.g., LCC local coordinate coding, drawn from the image processing field) or other are employed.

A decision based neural network may be employed after a template matching step is performed, so that the decision may be validated.

The physiological fingerprint of the user may be referenced to check that the "correct" (i.e., expected) user is detected. This reduces/removes the ambiguity that may occur when a non-contact sensor that is placed for example on a nightstand is monitoring User A. User A may get out of bed (e.g., to go to the bathroom or to work etc.), and a different User B (e.g., bed partner(s), baby or pet) may then move into range of the sensor. A basic sensor data processor may detect the parameters of User B, and then confuse these with User A. A more advanced processor will detect the "fingerprint"/patterns of User B and distinguish these from A. For a static sensor with a known set of Users, the system may have access to supervised training data as part of a learning processed. For unknown users (i.e., unknown to the system), a semi-supervised (i.e., with knowledge of User A, but not of B, C etc.) pattern recognition can be performed, or an unsupervised system if no distinguishing labelling is available to the system. A semi-supervised or unsupervised system may require multiple days/nights of data to generate a "fingerprint" of the characteristic combination of physiological and behavioral parameters of a User.

1 During enrollment of a system using a non-contact or minimal contact sensor in the bedroom, a subject could be asked to perform a specific breathing exercise in front of the sensor—e.g., a guided deep breathing signal. The system can enrol a user when guided with a specific deep or shallow breathing pattern of a defined inspiration/expiration period and depth. The level of coherence with the detected heart rate signal and other HR features could be used as a baseline input. A more complex enrolment would require recording a longer period of spontaneous breathing (e.g., an overnight signal) in order to train the system and/or monitor daytime sensor data.

Figure 6:
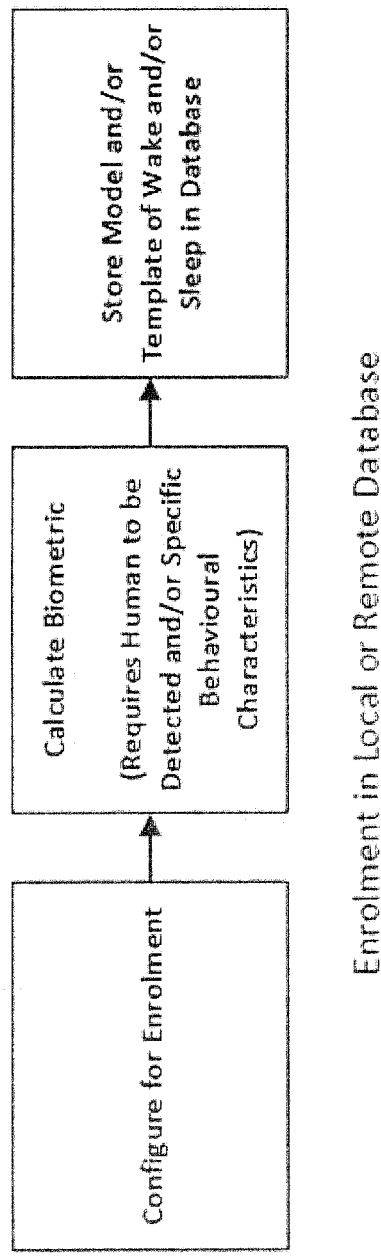
FIGS. 6 and 7 illustrates system processing for enrolment (training) and subsequent verification or rejection of identity.
Figure 7:
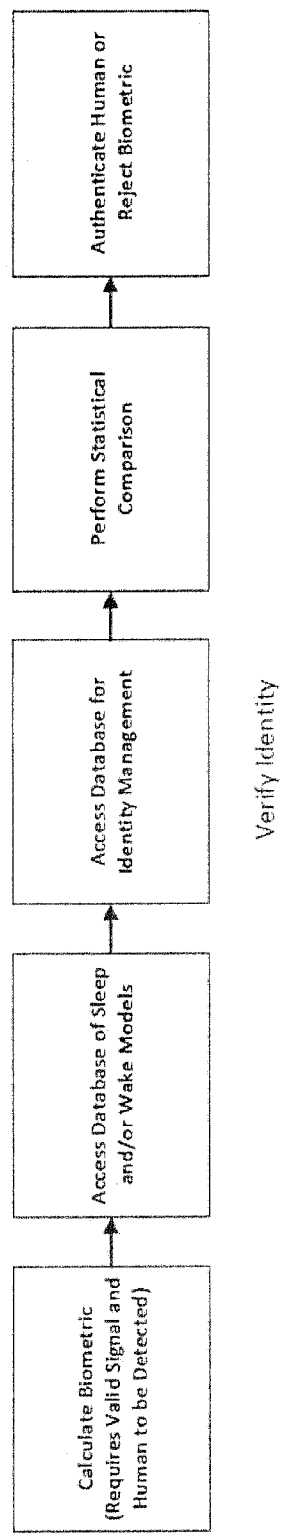

Algorithmic processing steps of an enrolment process and subsequent verification of identity is provided in FIGS. 6 and 7. In FIG. 6, the system is initially configured for enrollment. This can be automatic or manual in nature; for example, to enroll a sleep session, this might be manually initiated, but then the system may automatically scan a data from a night period to identify the fiducial points and calculate features in order to generate a biometric signature ("fingerprint") for the user (e.g., model weights for a classifier). This is then stored in a database for later biometric lookup and comparison. A daytime enrollment aggregates data from one or more monitoring devices, and may also process user behavioral data in order to generate a signature. Behavioral data may be allocated a lower weighting than physiological data, as aspects of these behaviors may be easier for a malicious user to mimic versus breathing and heart signals.

In FIG. 7, the initial step is that valid signals are detected (e.g., "presence" detected in the field of an RF sensor, above sensor baseline activity on an accelerometer etc.), and that a human is detected (implies respiratory and cardiac signals detected), the features are calculated, and the machine learning algorithm outputs a biometric estimate. The system then accesses the database to check for an appropriate (to the detected signals) sleep and/or wake models. Based on the probability that a specific user is detected, the system accesses an identity and access management (IAM) system in order to check for a likely candidate. A statistical comparison is performed, and a decision is made to either authenticate the human's biometric as valid (and grant or check an associated authorisation level—or refer to a separate database for same) or to reject the biometric (not authenticate the user).

Sample graphs of heart rate and breathing rate are shown for User A and User B (as detected by an RF sensor) in FIGS. 8 and 10. Associated histograms of these signals are presented in FIGS. 9 and 11.

Figure 12:
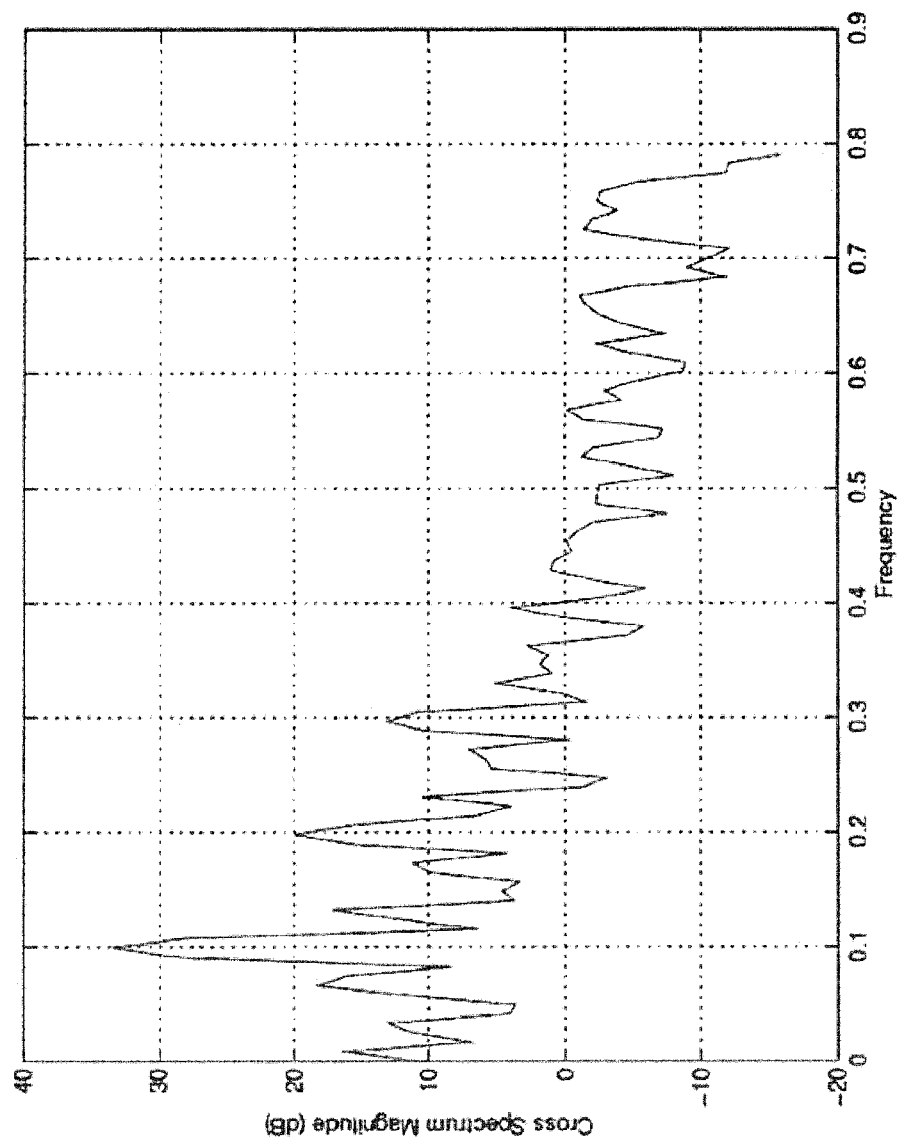
FIG. 12 illustrates cross spectral density between HR and BR for a paced breathing frequency of 0.1 Hz. Enrolment could include a period of paced breathing as well as spontaneous breathing.

FIG. 12 shows the cross spectral density between segments of heart rate and simultaneous breathing rate for a subject carrying out paced breathing at 0.1 Hz (6 breaths per minute deep breathing). The peak in the cross spectrum (such methods may be used to characterise relationships between systems) at 0.1 Hz shows the joint impact on heart rate and breathing rate.

Detection and rejection of data from animals sleeping in the bed is made possible by this system—e.g., dogs and cats. Detection and rejection of BR and HR components of a second person in the bed is also possible, e.g., for the case of a longer range sensor detecting the second person for part of the night recording, or all night if the first person is away.

More generally, for the case of an employer or insurer providing an incentive to a User to use a particular monitoring technology (e.g., to indicate activity/exercise over a period of time), then the estimated biometric parameter(s) can be used to check that the authorized user is in fact utilizing the technology and not another party (either accidental or deliberate impersonation).

The relationship of specific sleep stages to breathing and/or heart rate parameters can provide extra insight into a user specific biometric identifier since during sleep the breathing and heart rate statistical parameters are not specifically under the voluntary control of the subject. For example, the system may be configured to detect that a user is in REM (dreaming) or deep sleep. For example, the system may implement methods for determining sleep states or staging, such as the methods disclosed in International Patent Application No. PCT/US2013/060652, filed on Sep. 19, 2013 and International Patent Application No. PCT/US2014/045814, filed on Jul. 8, 2014, the entire disclosures of which are incorporated herein by reference. Preferentially, deep sleep may be chosen such that the impact of daytime stressors is least evident. REM sleep may show greater respiratory change in some cases, but may also be impacted to a greater degree by SDB episodes, PTSD (post-traumatic stress disorder) or other issues. Light sleep (stage 2) may also be analyzed or stage 1 light sleep parameters.

Critically if a person is asleep, they are not consciously modulating their breathing in as specific pattern, reducing the likelihood of tampering with the signal. Therefore, a separate waking and sleeping model may be created for a user. In fact, a separate model could be created for deep, REM or other sleep stages. Thus, in the identity authentication process, in some cases, a fingerprint for a person for any or each of these stages may be used. These sleep stage specific fingerprint(s) may then be evaluated in the identification process with suitable features determined in the particular sleep stages so that an identification of a person may be made in relation to particular sleep stage(s).

In this regard, the system can provide an analysis of the data under analysis, and trend over multiple nights.

Additionally, the breath patterns detected by a PAP device or RPT may form part of the "fingerprint" of the user. A patient interface or patient circuit, such as a conduit and/or mask, or other such device as described in more detail herein, may include extra sensing such as accelerometers, or the movement of the conduit (e.g., CPAP hose)) may be detected, adding characterizable movement information to the extracted breath parameters. In such a manner, the PAP device can check the biometric "fingerprint" of the user for compliance purposes.

It is noted that a simple increase in breathing rate can be related to non-chronic conditions, such as the common cold.

A multi-parameter holistic analysis of the health on an individual person implies that the system is aware of context, and is able to relate relevant data to the correct user. For example, an insurance company might provide a discount to a user of the system based on the user meeting certain health improvement targets. Such targets could be to achieve a decrease in average heart rate, decrease in breathing rate, increase an exercise intensity etc.

A simple actigraphy sensor or a change in galvanic skin response and/or skin temperature recorded by a wearable sensor can be used to augment this biometric classification. For specific heart rate and GSR changes, these can be cross referenced to exercise intensity to indicate whether a stress event or activity is mediating a particular change. For each person, they may exhibit specific sequences of heart rate, breathing rate, and GSR changes in response to exercise or a stress event. Thus the user's inherent stress levels and ability to cope with stress can serve as biometric markers when combined with other available parameters.

Longer term patterns in exercise intensity and steps taken can be correlated with user specific behaviors.

The system may be configured to detect the theft of the monitoring equipment (e.g., of a device with an RF sensor), i.e., that the biometric of an un-authorized or unknown user has been detected. Such a decision may make reference to location data (e.g., GPS coordinates) if available from attached equipment, such if location data is included as part of the "fingerprint."

The system may be used in a hospital setting in order to automatically separate readings from different patients as they move to different monitored beds in a hospital or are discharged, and the bed is reused. The system could automatically correlate hospital/clinic data collection from a monitoring device to a second device that is given to the patient to take home for long term monitoring.

It is noted that this could be quite robust to replay attacks, whereby an attacker/nuisance tries to mimic or replay a RADAR signal—e.g., from a second RF sensor under the attacker's/nuisance control. The first RF sensor could be configured to detect emissions and interference from the second RF sensor, and flag a warning signal to the system. In fact, the system can provide continuous authentication, as the physiological signals can provide a fresh biometric every few seconds.

The system by identifying the biometric of a first person and a second person in a bed may feedback a control signal to an RF sensor in order to adjust the range and/or power level of the sensor to detect the desired person (e.g., the first person).

Thus, in some cases, the system may aggregate multiple sources of information, and by smart processing of these data, and/or with the feedback to the user and devices of specific information may identify the user—for example, from nocturnal/during sleep recordings. Other versions of such a system may target only certain parameters, or not adapt to user specific parameters.

Potential benefits of some versions of the technology may include:

1. The system can detect physiological patterns and identify a human based on heart and/or breathing signals.

2. The signals may be captured via a pulsed radio frequency (RF) sensor or group of sensors.

3. The system can identify the biometric parameters of a user, i.e., verify that signals recorded are from a given user based on heart rate and/or breathing rate and/or amplitude recorded by a non-contact sensor.

4. The system can update the biometric during sleep and wake phases.

5. The sleep state reduces/removes conscious variability imposed on the signals (i.e., reduces risk of misclassification or user "faking" a breathing pattern which may also impact heart rate)(e.g., as noted in the OH&S use case).

6. It can update the biometric preferentially during deep (best) or REM (second best) sleep.

7. The system can communicate with a server to check existing identity templates/models and determine an identity.

8. The system can enroll a user using wake or sleep phases.

9. The system can enroll a user when guided with a specific deep or shallow breathing pattern of a defined inspiration/expiration period and depth.

10. A system using a pulsed radio frequency (RF) sensor can detect and notify if a second unauthorized second RF sensor is introduced in order to mitigate "replay" attacks against the system.

11. The system can detect health condition of a person, and receive inputs if treatment/therapy etc. is made such that it can retrain to the new health condition, including lock and key for flow generator, and smart adaption of an adaptive servo ventilator (ASV) to heart rate. It may ensure that proper person is using the therapy device with previous settings intended for the person, otherwise it may reset to settings more appropriate for a new/unknown user.

12. The system can update the biometric data, such as in a database or library, during the day, and at night, from wearable sensors, including breathing rate, heart rate, motion patterns, galvanic skin response, blood pressure (also accelerometer for daytime breathing rate, and using "liveness" data from other sensors such as video).

13. The system can detect when a second biometric is detected for some or all of a recording period, in order that a second or third person's data not be processed in error by a system focused on the first person.

14. The system can detect an animal such as a dog or cat sleeping or awake in the field of the sensor.

15. The system by detecting two people (two biometrics) in a bed can send a control signal to the sensor/processor to adjust the sensor behavior (power/range gating/directivity) to better detect the first person (Additional details and examples here of adjusting sensors based on biometrics, and selecting lowest sensor power for a given situation).

16. The system can be cloud-based, so that it can track a person's biometric across multiple fixed or mobile sensors in different places such that a sensor(s) does not need to be moved with the person. For example, the system may track a person from a first sensor in a first room to a second sensor in a second room, and automatically collate their physiological data from the first and second sensors.

8.0 Multi-Sensor Cooperation with Biometric Feedback

For the case of a plurality of sensors cooperating, such as communicating over a wired or wireless link (either continuously or as part of a pairing process) such in a system with a control processor either remotely located or co-located with a sensor, characteristic biometric parameters can be used to dynamically adjust the performance of one or more sensors in order to optimise the physiological recognition of independent human sources, and to reject other sources.

For the case of two or more sensors in proximity to each other exchanging information in order to minimise RF interference, or other types of interference, the biometric identity and/or associated biometric quality of a human or humans detected by each sensor can serve as a basis for adjusting the control parameters of one or more sensors. For example, adjustable parameters may include the range gating pulse timing and emitted power levels (within allowable regulatory limits) or RF detection frequency (e.g., center frequency) of the sensors. Such changes are most easily achieved on a digitised sensor design, although control signals could be provided to an analog sensor device that is configured to allow this.

Sensors may be configured to use the lowest possible amount of power in order to achieve a good signal quality biometric. This may be beneficial for environmental reasons, and for the added ability for the sensor to be battery powered. Additionally, the possibility of interference with other sensors or devices may be minimized.

8.1 Biometric Control of Multi-Sensor Array

Figure 13:
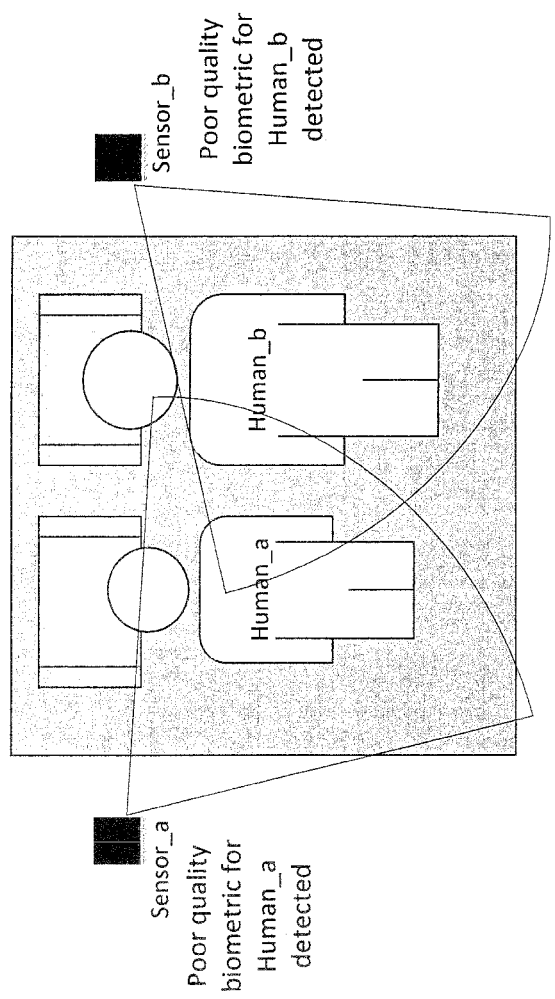
FIG. 13 is a diagram illustrating two sensors monitoring two humans in a default configuration. Biometric quality is degraded as the sensors are receiving overlaid breathings and heart rate signals from each person, and movements of both persons are being detected.

Sensors may be configured to operate in close proximity with each other, while maintaining minimum RF interference. In this regard, two sensors may be placed on opposite sides of a bed and programmed to monitor separate individuals sleeping in a common arrangement. For example, the biometric characteristics of a particular user may be detected by each sensor and each sensor may be initialized with such user data such that the sensor includes a baseline of data attributable to the user. However, during further operations, as shown in FIG. 13, quality of the sensors may be degraded as the sensors may receive overlaid signals from each person. For example, Sensor_a, programmed to detect signals from Human_a, may receive overlaid breathing, heart rate, and/or movement signals from Human_b, thereby degrading the received signal for Human_a. Similarly, Sensor_b, programmed to detect signals from Human_b, may receive overlaid breathing, heart rate, and/or movement signals from Human_a, thereby degrading the received signal for Human_b.

Figure 14:
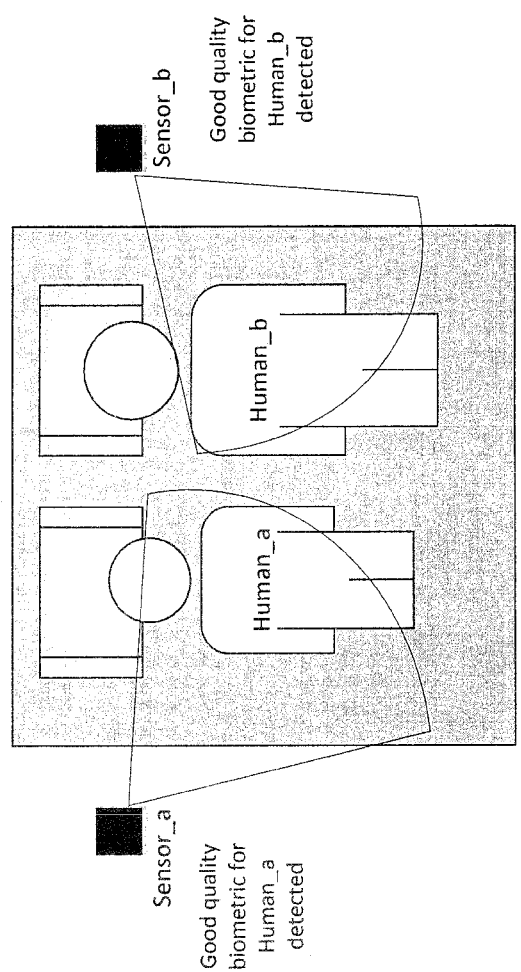
FIG. 14 is a diagram illustrating two sensors monitoring two humans. Biometric quality is excellent as the sensors have been configured to minimise range and power in order to maximise clear, separated biometrics.

To avoid such degradation, the sensors may be adjusted to minimize interference. For example, as shown in FIG. 14, two sensors placed on opposite sides of a bed and programmed to monitor separate individuals sleeping in a common arrangement may be programmed to minimize interference by adjusting the range and power of each sensor. In this regard, Sensor_a and Sensor_b, programmed to receive biometrics from Human_a and Human_b, respectively, may be configured to minimise range and power in order to maximise clear, separated biometrics. For example, upon detection of biometrics that are unexpected or not particularly identified with a given user's "fingerprint", the sensor may reduce its detection range. In the example of FIG. 14, Sensor_b upon detection of biometrics recognized to be associated with its initialized user and biometrics not recognized to be associated with its initialized user, the sensor_b may reduce (e.g., incrementally) its detection range (e.g. via power or range gating adjustments) until it detects only biometrics recognized to be associated with its initialized user. Sensor_a may be similarly programmed. Accordingly, the biometric quality received by both Sensor_a and Sensor_b may be excellent, as the sensors detect only biometric signals from a single human.

Figure 15:
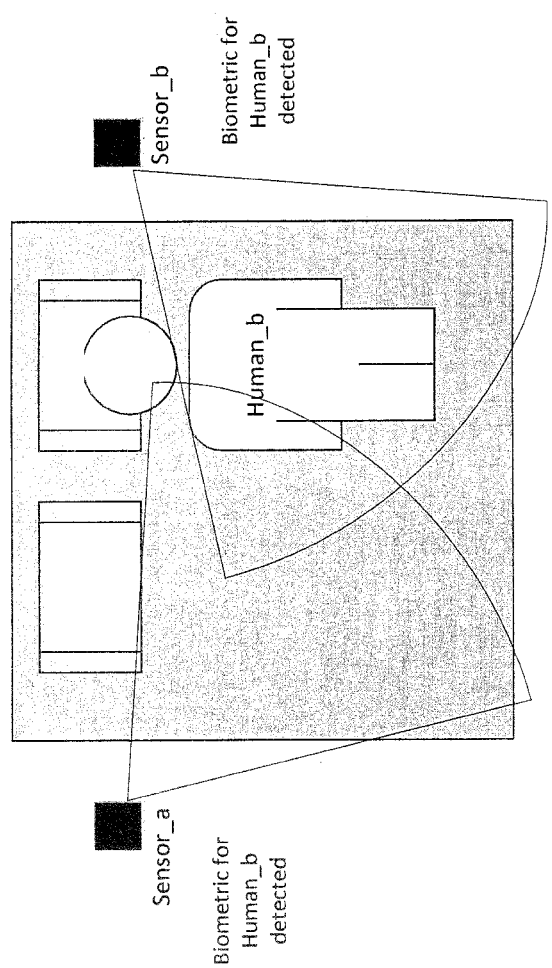
FIG. 15 is a diagram illustrating two sensors monitoring one human in a default configuration. Biometric quality is degraded as Sensor_a "sees" Human_b and duplicate biometrics are detected in at least one of the sensors.

In some embodiments, two sensors placed on opposite sides of a bed and programmed to monitor separate individuals sleeping, may only be monitoring a single individual. For example, as shown in FIG. 15, Sensor_b, programmed to detect signals from Human_b, may receive breathing, heart rate, and/or movement signals from Human_b, as intended. That is, for example, the sensor may recognize its initialized user from the detected biometric data. However, Sensor_a, programmed to detect signals from Human_a (not currently present), may receive breathing, heart rate, and/or movement signals from Human_b. That is, for example, the sensor may recognize that the detected biometric data is not from its initialized user. Accordingly, biometric quality is degraded as Sensor_a may duplicate biometrics detected by Sensor_b or the signals may otherwise interfere.

Figure 16:
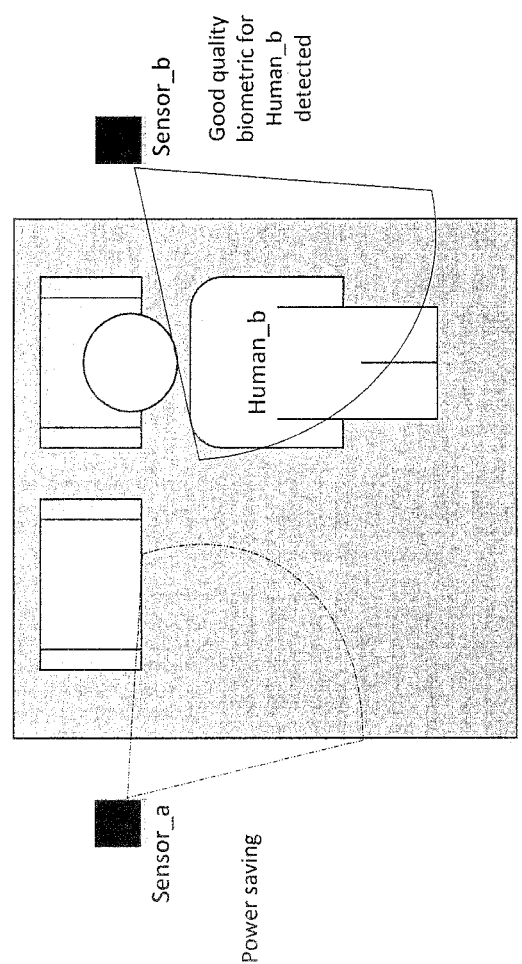
FIG. 16 is a diagram illustrating two sensors monitoring one human in a configuration to minimise range and power in order to maximise clear, separated biometrics. Sensor_a enters a power saving/search mode. Sensor_b detects a clear biometric of Human_b.

To avoid duplicate biometrics or other interference, a sensor programmed to receive biometrics of a certain individual, such as upon detection of only unrecognized biometrics, may enter into a power saving mode and/or search mode, wherein the sensor reduces or terminates, for example, sensing or sensing range. Thus, as illustrated in FIG. 16 one sensor may sleep while the active sensor may work with minimized interference. In this regard, Sensor_b, may be programmed to detect breathing, heart rate, and/or movement signals from Human_b, and Sensor_a may be programmed to detect signals from Human_a (not currently present). Sensor_a may avoid duplicating the biometrics detected by Sensor_b by, upon determining that Human_a is not present, going into a power saving/search mode. Power saving and/or a search mode may limit the range and power of a sensor, while it awaits for a certain individual to return. As such, duplicate biometrics are no longer received.

Figure 18:
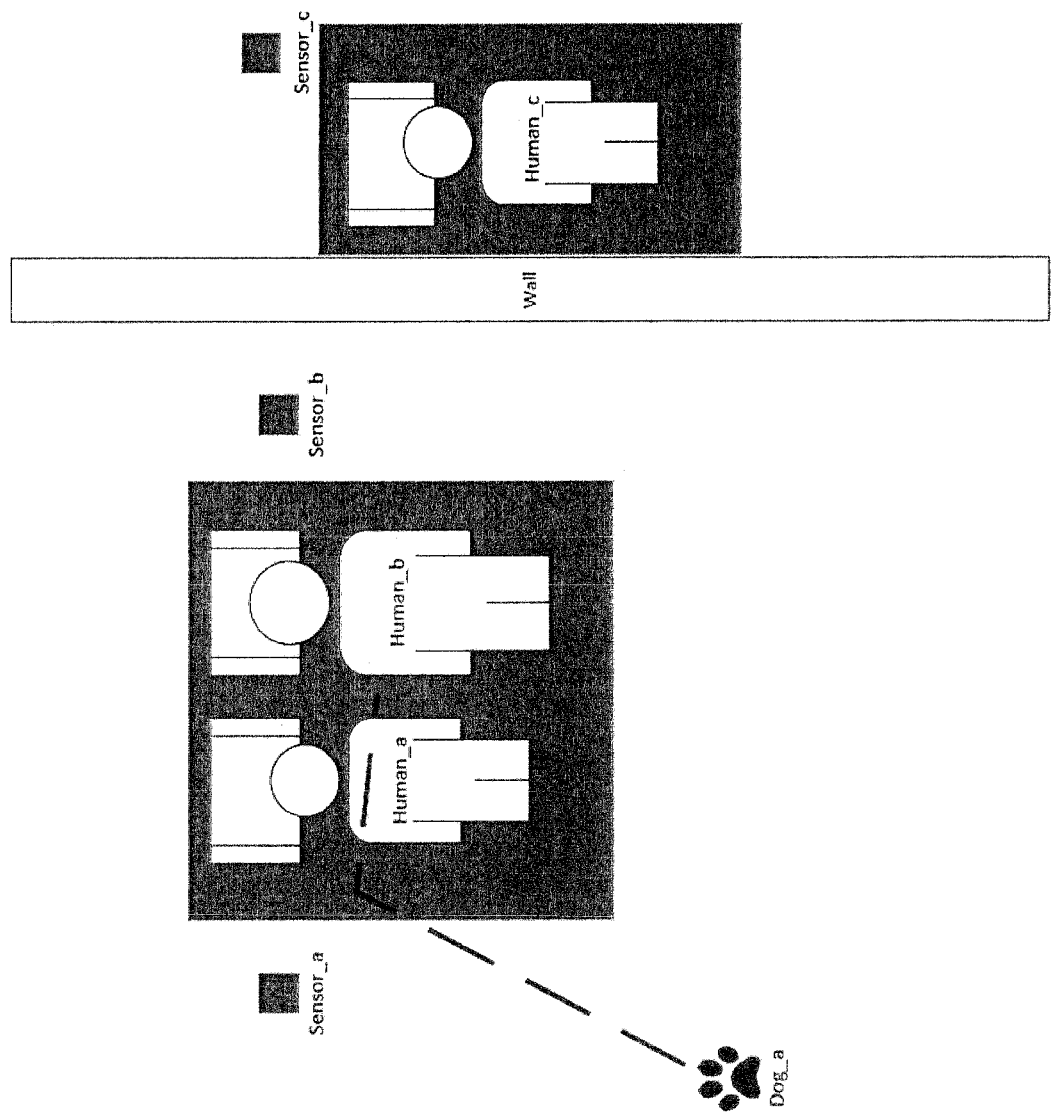
FIG. 18 is a diagram illustrating three sensors monitoring three humans with interference of another living being (e.g., a dog).

In certain embodiments, more than a couple of sensors may be used. For example, as shown in FIG. 18, three sensors in close proximity may be used. In this regard, a first sensor "alpha" (Sensor_a) may be located on a nightstand on a first side of a bed, and directed towards the first human (Human_a), who may be an initialized user of Sensor_a. Human_b, sharing a bed with Human_a, may be monitored by a second sensor "beta" (Sensor_b), located on a nightstand on a second, opposite side of the bed, and directed towards the Human_b, who may be an initialized user of Sensor_b. In one example, Human_b may be a large subject with a body mass index (BMI) greater than Human_a or Human_c. Additionally, Human_c may be sleeping in a bed located on the far side of a thin partition wall to Human_b and Human_a. Human_c, who may be an initialized user of Sensor_c, may be monitored by Sensor_c.

The system may configure Sensor_a to operate at an odd frequency, Sensor_b at an even frequency, and Sensor_c at an odd frequency. As such, RF interference between the group of sensors may be minimized.

Biometric signals may then be detected from each sensor device. Based on the detected biometric signals, Humans a, b, and c may be identified based on their "fingerprints". In this regard, Sensor_a may detect sections of biometric signals identified as Human_b (other side of the bed) when Human_a is not detected (e.g., Human_a has left the room). In other words, Human_b's biometric has been detected by both Sensor_a and Sensor_b. Accordingly, a system control processor may send or generate a control signal to Sensor_a to adjust the range gating to shorten the range, and continue to monitor the biometric detected. Further, the system control processor may optionally reduce the power level of Sensor_a.

When Sensor_a detects Human_a, the sensor may be adjusted or otherwise activated to go into a normal power state. When a configuration is achieved whereby Sensor_a correctly detects Human_a's biometric (when Human_a is actually in the room), and Human_b's is not detected, the control parameters for the detection configuration can be stored as an optimal set up.

Additionally, the sensor may be programmed for further control changes when individuals or animals, not intended for monitoring enter the range of a sensor. For example, as shown in FIG. 18, a dog, "Dog_a" may enter the bed, by way of climbing over Human_a into the centre of the bed. The sensors may detect the non-human biometric, and the sensors, upon such detection, may adjust their range gating and/or power parameters (e.g., both Sensor_a and Sensor_b) in order that biometric of Dog_a is minimised in favour of preferentially detecting Human_a and Human_b for Sensor_a and Sensor_b respectively.

In this manner, the behaviour of the sensors may be adjusted one or more times during a monitoring session, such as by a control processor of the sensor or other system control processor that includes any of the detection methodologies described herein.

For any case where optimisation of sensor parameters does not yield an improvement in the biometric quality, the user or users may be prompted to adjust the orientation of one or more sensors.

In an example of a multi sensor setup, such as that shown in FIG. 18 (including Sensor_a, Sensor_b and Sensor_c), the sensors may optionally include a processor programmed for a location check (e.g., GPS or other input data) and/or to set detection frequencies to minimize interference. In this regard, the processor may determine and utilize a RF detection frequency that is suitable for the location of the sensor. For example, if the sensor determines its location to be in the USA, the sensor may access data (e.g., a table associating frequencies and geographic location) and set the target detection center frequency and FCC spectral mask and other settings from the table in association with the USA. Similar parameters could be used in parts of the EU depending on the appropriate ETSI (European Telecommunications Standards Institute) spectral mask, and allowed centre frequencies in that region (or indeed in other countries based on local regulations). As such, Sensor_a's center frequency can automatically be adjusted to 10,527,125 kHz, and with a power level of 43.8%, and range gating (time of flight) adjusted to provide a detection roll-off at 92.5 cm. Sensor_b's center frequency can be automatically adjusted to 10,525,000 kHz, and with a power level of 93.2%, and range gating adjusted to provide a roll-off at 165.2 cm. Sensor_c's center frequency can be automatically adjusted to 10 522 375 kHz, and with a power level of 80.0%, and range gating adjusted to provide a roll-off at 150.0 cm.

In one example, Human_a was seen to have a median heart rate of 51.4 bpm with an interquartile range of 6.3 bpm during deep sleep, and median heart rate of 55.7 bpm during REM sleep with an interquartile range of 9.1 bpm. Human_a's personal biometric can be best described with median values, and the shape of the resulting histogram, and a medium to high coherence between respiration and heart signals. Human_a's breathing rate was 13.1 br/min (+−/3.2 br/min) during deep sleep, and 13.9 br/min (+/−1.1 br/min) during REM sleep.

Human_b, over the course of a full night, exhibited an average heart rate of 77.5 bpm with significant accelerations of nearly 30 bpm, with increased interbeat variability due to an underlying intermittent arrhythmia. Human_b's average breathing rate of 18.2 br/min, increased to over 20 br/min during periods of significant heart rate acceleration. Variation in br/rate during REM sleep was 4.5 br/min. Cessations of breathing (apneas and hypopneas) were detected in the breathing trace. Characteristics bradycardia/tachycardia sequences in HR are related to these apneic episodes. HR/BR coherence is generally low due to the noted variability in both HR and BR. Skewness and kurtosis figures indicate an uneven distribution.

Human_c was seen to have an average heart rate of 59.8 bpm, which is particularly stable during deep sleep. During REM sleep, variability increased dramatically to oscillations of 2 to 23 bpm. Human_c's breathing rate average was 17 br/min, with a minimum of 15.2 br/min.

On the entry of Dog_a in the space between Human_a and Human_b, Sensor_b may adapt to Human_a's slightly closer position as previously described. For example, upon detection of unrecognized/initialized biometrics, a processor controlling the sensor may control a change to the sensor such as its detection power, frequency or other control parameters for sensing. For example, the center frequency may be adjusted to 10,525,000 kHz, and with a power level of 84.9%, and range gating adjusted to provide a roll-off at 145.6 cm. This would help with distinguishing the dog from the humans by restricting Sensor_a parameters such that only Human_a is detected (e.g., by adjusting the range, power level or direction of detection), and Dog_a is rejected (i.e., not detected); similarly, Sensor_b parameters are adjusted automatically such that only Human_b is detected, and Dog_a is rejected. The system can also flag that an unknown biometric is detected, and furthermore that the respiratory rate, respiratory depth and heart rate parameters are consistent with an animal. While the average dog at rest takes 24 breaths per minute, such a high breathing rate in humans is more characteristic of chronic disease such as congestive heart failure or COPD (Chronic Obstructive Pulmonary Disease), and but accompanied by shallow breathing (relative to the population average or personal baseline) in humans, and with different heart rate variability. Where a dog or cat has been exercising heavily or exposed to hot temperatures, a faster respiratory rate with an open mouth (panting) is to be expected for a period of time. A canine common breathing range is around 20-30 br/min, and heart rate is typically 60-100 bpm for large breeds, 100-140 bpm for small breeds, and around 220 bpm in puppies. A typical feline breathing rate range is 20-40 br/min, with a heart rate of 140 and 220 bpm. Total lung capacity tends to increase in mammals with increasing body mass; the average cat or dog is lighter than an adult human, and also with different patterns vs. a baby or child. Thus, sensor control parameters may also be adjusted upon detection of one or more of such biometric characteristics that are recognized by the processor to be indicative of a non-human animal.

Similarly, by way of further example, if Human_a left the bed, Sensor_a may enter power saving/search mode with center frequency 10,527,125 kHz, and with a power level of 0 to 100%, and range gating (time of flight) adjusted to provide a roll-off of 50-300 cm. With prior knowledge of the existence of Sensor_b, Sensor_a's search mode may be able to limit the power percentage and roll-off distance to minimize possible interference pulses entering Sensor_b.

In some embodiments, steerable antennas (e.g., using classic phased arrays or digital beam forming) may be used to adjust coverage range of the sensors, and to minimize interference. For example, the sensing "cone" of Sensor_a and Sensor_b would be adjusted to fully exclude any biometric evidence of Dog_a.

Figure 17:
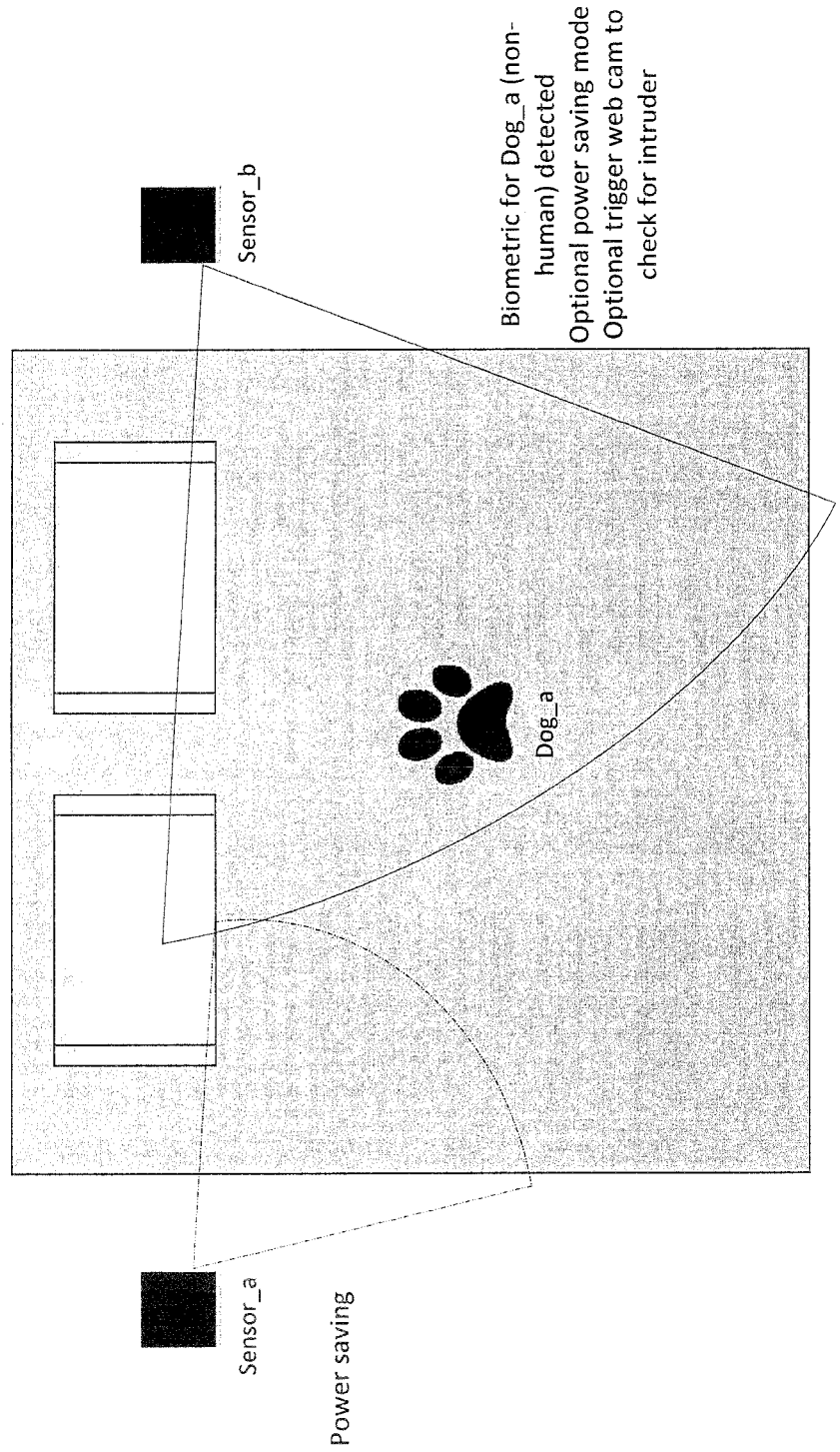
FIG. 17 is a diagram illustrating two sensors monitoring a bedroom in which an animal (dog) enters the room and lies in the bed. Sensor_a enters power saving/search mode, while sensor_b monitors the non-human heart rate and respiration rate signals.

Optionally, in some cases, further systems may be triggered based on the biometric identification of the sensor, such as where the sensor does not identify an initialized user. For example, as illustrated in FIG. 17, a processor of the system may trigger or send an alert (e.g., to Human_a and Human_b's smartdevice) to alert of the unexpected biometric (e.g., a dog biometric). By way of further example, the processor upon such a detection may activate a web cam or trigger a sound alert (e.g., through a speaker).

By detecting a particular biometric, a custom configuration of light and/or sound and/or environmental parameters can be set (i.e., controlled by a controller/processor that makes the identification). As an example, consider a system where two partners share a bedroom. When the first partner is detected, the system turns on a smart TV to a sports channel (or stream via an online service such as Netflix or similar), and turns off the main bedroom light. After a time period, the user is detected as asleep, and soft jazz music is turned on via a Hi-Fi system, and the TV is turned off. After the user enters deep sleep, the Hi-Fi is slowly reduced in volume and then turned off. If the second partner is detected in the bedroom, the Hi-Fi/radio is configured to play popular music/latest top 20 hits from a stored music collection or via a streaming music service (e.g., Spotify, Deezer, Apple); in addition, the room lights are dimmed, and bedside light configured to have an orange/red tint with low white/blue content. The TV is configured to display a sunset video sequence (with low backlight intensity) or to simulate a fireplace. As the second partner falls asleep, the music and TV are slowly reduced in amplitude/dimmed, until the user enters deep sleep whereby both are now turned off. Where the two partners are in the room at the same time, the sports TV/video stream is directed to wireless headphones for the first partner, and the pop music to the second partner's wireless headphones (or pillow speaker). Where available, the TV polariser is configured to direct the sports feed to the first user, and the fireplace video to the second user. Therefore, the biometric detection of one or more partners allows a customised bedroom (or indeed living room) experience. Similarly, for a wake up experience, an alarm may be customised based on the first partner and second partner. For example, the first partner may wish to wake later than the second partner. As such, a low amplitude alarm with focused light may be used on the second partner, to avoid waking the first partner. Such preferences may be programmed into the system and accessed based on the identification made by a processor of the system.

For example, the system may also alert a user if another animal and/or human (unrecognized) enters a sensor's sensing space. For example, as shown in FIG. 17, Dog_a (or indeed another animal or a human) enters a sensor sensing space, an alert can be triggered by the system. Optionally, an image or video of the event could be triggered and stored and/or transmitted to an authorized person for review. In this regard, a triggered camera (e.g., network attached, low light, infra-red with associated illuminator, thermal or other type) or webcam may send a video of the unrecognized individual to an authorized person. To underscore this point, such an alert could also trigger if an unknown human biometric such as a burglar/intruder was detected in the field of one or more sensors. Where video and/or audio sensors are accessible or under the control of the system, the recording or live transmission of video and/or audio may occur, e.g., for review by a monitoring centre prior to contacting the police. This biometric detection can also be used to reduce false activations of an intruder alarm system, when implemented in conjunction with other detection equipment in a property, such as PIR (passive infrared), other microwave intruder sensors, glass break detectors (vibration or acoustic), magnetic contact switches, shock sensors, video motion triggered or pressure activated (such as mats).

It can be seen that such biometric detection if implemented in an apartment block or office building could help firefighters check a human (biometric) count provided by a fire alert system (and optionally correlate with an access card system if in place). Such RF sensors may continue to function in smoky or high heat situations versus standard video feeds (and RF does not have the same privacy implications as full video processing, e.g., for possible use in bathrooms/bedrooms etc.). If user biometrics were registered with the system, such as a central controller or computer receiving identifications from a collection of sensors, such a fire alert computer could output a list of names and locations within the building/structure. Thus, the central computer may maintain data to identify the locations of each of the sensors and provide such a list in emergencies in conjunction with identification of persons who are within detection range of a sensor of the collection of sensors.

Such RF sensors can be powered in a number of ways. For example, an RF sensor could be placed within a pass through AC outlet (i.e., plug into a mains socket/AC outlet, and provide a piggy-back AC outlet in a very slim form factor; a USB socket could also be provided on the socket faceplate to provide a secondary use of the device). A night light feature could also be provided on the device, e.g., if placed in a hallway, and activated by detection of motion using the RF sensor. The RF sensor would sense within the field of the socket/AC outlet (e.g., to cover part or all of a room), and transmit data via Wi-Fi or other wireless communications means, or via the mains wiring (e.g., via Homeplug or similar standard). A different example is where a pass through USB adaptor or cable is provided. The RF sensor and communications (e.g., via Wi-Fi or over the USB link itself) is integrated into the adaptor or cable, and scavenges/draws power from the 5V provided in the USB specification. This allows RF sensors to be placed anywhere USB cables are provided, e.g., plugged into a phone/tablet charger at the wall, into a laptop etc. It can be seen that by plugging such a device into a laptop or tablet, a biometric could be checked for the user in front or near the device. Either of the AC outlet device or USB inline device options provides a very low cost, simple (just plug device in) ability to monitor a space for biometric characteristics.

9.0 Further Methodologies for Identification/Distinction

As previously discussed, identification methodologies may be employed by a sensor to distinguish beings proximate to the sensor. In the following further example, multiple beings may be distinguished so that a particular user may be identified).

9.1 Introduction

A large proportion of adults sleep with a partner, with potentially different sleeping patterns. The partner could go to bed before a main (or primary) user of a sleep sensor, or may stay in bed after the main user leaves the bed. To avoid mistaking the partner for the main user, processes may be employed by a system to distinguish between them. In some cases, this could allow the main user's sleep to be assessed in isolation—(i.e., separated from sensed data of the partner).

9.2 Methodologies

9.2.1 Experimental Design

A pilot study was conducted, for which five healthy subjects were recruited. Each subject sleeps with a partner. A 10.5 GHz non-contact sensor was set up next to the subject's (or User's) bed, on their bedside unit, facing towards their chest. See FIG. 1. The non-contact sensor was set up to record data 24 hours per day for the duration of the study. The primary user (hereinafter user) also provided a diary detailing when they went to bed, when their partner went to bed, when they got up in the morning and when their partner got up.

Sensor data was split into 24 hour recordings, with start and end time equivalent to the time the device was initially turned on. A set of annotations was manually created (based on the user supplied diary entries of to-bed, out-of bed) for each recording to identify, (a) user data, (b) partner data, (c) absence, and (d) 'not enough information'.

9.2.2 Sensor Signal and Pre-Processing

An example sensor system outputs two analogue voltage signals, which represent the I and Q signals of the sensor. The sensor operates by generating two short pulses of radio frequency energy at 10.5 GHz. The first pulse acts as the main transmit pulse, and the second pulse is the mixer pulse. The first pulse reflects off nearby objects to create an echo pulse that is received back in the sensor. The distance traveled by the echo pulse introduces time delay in the arrival of the echo signal back at the sensor. This time delay results in a phase shift between the echo signal and the reference mixer pulse. By multiplying ('mixing') the echo pulse with the mixer pulse inside the receiver, a signal proportional to any phase shift of the echo pulse is generated. Moving objects (such as a person breathing) generate a variable phase shift that can be detected by the electronics in the circuit (de Chazal, P., Fox, N., O'Hare, E. et al. Sleep/wake measurement using a non-contact biomotion sensor. J. Sleep Res., 2011, 20: 356-366).

Sensor data are filtered (low-pass and anti-alias filtered, and in parallel, high-pass and anti-alias filtered for movement analysis) prior to analysis. Data are analyzed in epochs (e.g., 30 second periods or other suitable time period).

Initial presence/absence detection was performed, followed by sleep/wake detection. Movement and activity levels may be quantified for every epoch. Respiration rate was calculated at 1 Hz. Full sleep staging analysis (light, deep and REM sleep identified) may also be performed.

9.2.3 Feature Extraction and Investigation

Features (e.g., 25 features (Table 1)) were then extracted (e.g., for every 30 second epoch of every recording). Thus, a processor may be configured to calculate or determine any one or more of the features of the table below in an identification process. For initial investigation, derived features may be compared for known periods of user and partner use, e.g., using one-way analysis of variance (ANOVA), to assess whether each individual feature could significantly discriminate user from partner. Each feature may also be compared with its mean value over a full recording and with the mean value from historical data for a specific subject. This will significantly increase the number of available features.

TABLE 1

(Example feature names and descriptions)

| Category | Description |
|---|---|
| Frequency domain analysis | Spectral peak ratio for I Channel. This may be determined using the ratio of the maximum peak of the power spectral density of the signal in the in-band range (0.125-0.5 Hz) to the maximum peak in the outside-band range (<0.125 Hz or >0.5 Hz). |
| Frequency domain analysis | Spectral peak ratio for Q Channel. This may be determined as with the I channel above but on the Q channel. |
| Signal quality | Set Up Optimiser flag vector which is determined based on signal quality and given a numerical value between 1 and 5. |
| Frequency domain analysis | Peak trough ratio for Q channel. This is the ratio of the amplitude of a spectral peak to the mean of the trough of either side during respiration using the Q channel. This is calculated over a pre-defined window length. |
| Frequency domain analysis | Peak trough ratio for I channel. This may be determined as with the Q channel above but using the I channel. |
| Respiration rate | This is the respiration rate (Hz) as calculated using an adaptive notch filter (ANF) on the Q channel signal. |
| Respiration rate | This is the respiration rate (Hz) as calculated using an adaptive notch filter (ANF) on the I channel signal. |
| Respiration rate | Breathing variability measure-local variation (SD) in breathing rate normalized to overall variation (SD). This calculation uses a retrospective window of pre-defined length. |
| Frequency domain analysis | In-band power (0.125-0.5 Hz) for I channel. This is the variance of the I channel signal in the frequency range 0.125-0.5 Hz. |
| Frequency domain analysis | In-band power (0.125-0.5 Hz) for Q channel. This is the variance of the I channel signal in the frequency range 0.125-0.5 Hz. |
| Time domain analysis | Range of signal for I channel. This is the difference between the maximum and minimum of the signal over a pre-defined window. |
| Time domain analysis | Range of signal for Q channel. This is the difference between the maximum and minimum of the signal over a pre-defined window. |
| Respiration rate | Final respiration rate output (Hz). This is only valid during periods of no movement. One value is provided for every 30 second epoch. |
| Respiration rate | Ratio of the maximum to minimum amplitude of a breathing cycle for Q channel estimated using a discrete cycle extractor (DCE) method. One value is provided for every 30 second epoch. |
| Respiration rate | Respiration rate output for Q channel (Hz) estimated using a discrete cycle extractor (DCE) method. One value is provided for every 30 second epoch. |
| Respiration rate | Ratio of the maximum to minimum amplitude of a breathing cycle for I channel estimated using a discrete cycle extractor method. |
| Frequency domain analysis | High band power (0.5-Fs/2 Hz) for I channel. This is the variance of the I channel signal at frequencies above 0.5 Hz. |
| Frequency domain analysis | High band power (0.5-Fs/2 Hz) for Q channel. This is the variance of the Q channel signal at frequencies above 0.5 Hz. |
| Respiration rate | Respiration rate output for I channel (Hz) estimated using a discrete cycle extractor (DCE) method. One value is provided for every 30 second epoch. |
| Respiration rate | Difference between final respiration rate and mean respiration rate over total signal. |

TABLE 1-continued (Example feature names and descriptions)

| Category | Description |
| --- | --- |
| Movement/ Activity | Activity removed by movement correction. Movements which are likely to have occurred during sleep are removed (PLM detector), and the activity signal during these sections is also removed. |
| Movement/ Activity | Movements removed by movement correction (movements attributable to periodic limb movements (PLM) detected by a PLM detector) |
| Movement/ Activity | Logistic regression output of turnover detector classifier. This is the probability that a change in torso position has occurred (such as a person rolling over in bed). |
| Movement/ Activity | Post-processed movement. This is the movement signal after the PLM detector has been applied. |
| Movement/ Activity | Activity count result. |

When implementing a classifier system for identifying/recognizing a particular person, the feature values may be determined or calculated for the User and Partner over the course of a period of time (e.g., nights, a night, one or more epochs, etc.). Any one of more of such calculated features may serve to provide statistically significant discrimination between a user and partner, either individually or by combining multiple features. The features in Table 1 were found to significantly discriminate User data from Partner data, with a p-value (where we consider statistically significant as $p<0.05$)) of less than or equal to 0.05, when individually assessed using one-way ANOVA. This indicates that these features are useful for inclusion in a classifier model to distinguish between user and partner data.

9.2.4 Example Classifier Training

Such a classifier may be employed using data from sensor recordings. For example, for each recording, all partner data may be used as part of the training set, and an equal number of user epochs may be randomly selected to complete the training set.

A feature selection routine (such as sequential forward feature selection) may be used within cross-validation (e.g. ten-fold cross-validation) to select the subset of these features which may be combined using a classification method, such as logistic regression, to best identify whether the user or only their partner was present. The selected features may then be employed as a classifier for implementation in a processing device to identify a person.

9.2.5 Classifier Performance Assessment

A trained classifier may be tested using data from sensor recordings. A testing set may include all partner data, and all user data.

Figure 19:
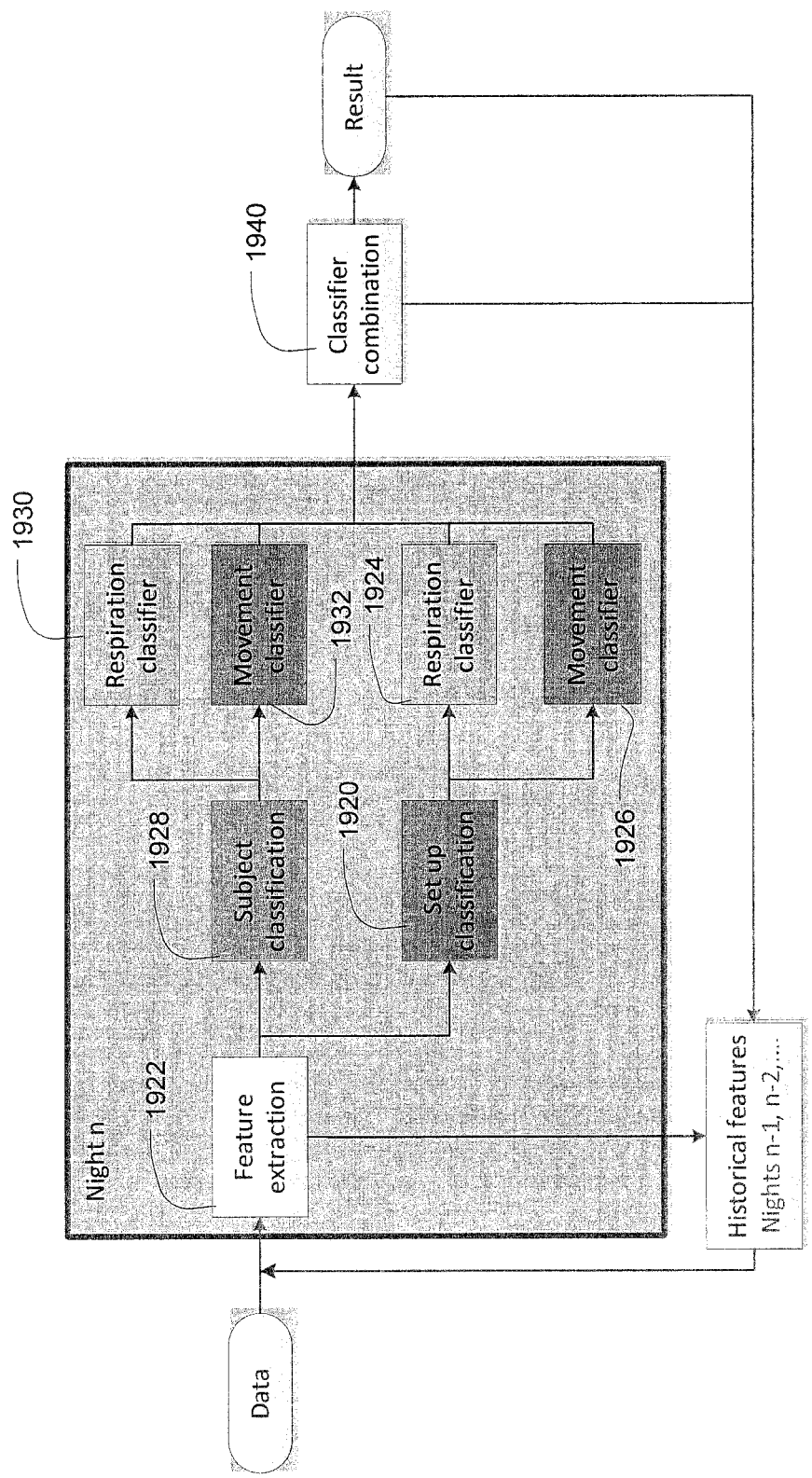
FIG. 19 illustrates processing of an example classification system for identification of a user.

9.3.0. Further Example Classifiers 9.3.1 Separate Classifiers for Movement and Non-Movement Many potential features provide non-meaningful (i.e. not-a-number/NaN or zero) outputs during movement or during non-movement (respiration) sections of data. For example, during sections of movement, set-up optimizer and respiration rate features may be equal to NaN. Similarly, movement features are equal to zero when no movement is detected, during sections of clear breathing. Thus, in some versions, detection features, such as those from Table 1, may be organized into discrete groups, such as a group with features that are meaningful during movement, and a group with features that are meaningful during clear breathing with no movement detected. These groups may have some overlapping features which are meaningful in both scenarios. A classifier model may then be employed for each group of features, and a movement flag set by analysis of sensor signals could be used as a trigger to select either a respiration or a movement classifier model for use at each epoch (see FIG. 19). Thus, depending on the movement flag different sets of features may be considered in the classification of whether the particular epoch concerns a particular user (e.g., user or partner).

9.3.2 Using Only Subject-Based Metrics to Develop Classifier

In some versions, features may also be categorized or grouped as subject-based or signal quality-based, and used to create two classifiers. Signal quality-based features are useful when training a model using real life data, i.e., annotated two-in-a-bed data in which the sensor was capturing data 24 hours per day, and both User and Partner were present individually for some period of time, and on a specific side of the bed (the user always within a certain range of distances from the sensor, and the partner within a different range of distances from the sensor). Using such a dataset, signal quality-based features together with subject-based features could be used to develop a 'Set up' classifier, FIG. 19. Alternatively, by excluding signal quality-based features, and only including subject-based features, such as respiration rate and movement, non-annotated data from two distinct subjects can be merged to develop a 'Subject classifier' (see FIG. 19). Typical recordings, in which a user starts recording when they are in bed and ready to go to sleep, and ends the recording when they wake up in the morning, do not typically include significant periods of partner data. Partner data would only be present when the main user is not in the bed but the partner is present—the signal would reflect off the main user while they are present and the partner would not be 'visible' at all). Since both User and Partner data in this scenario would likely have been captured using the same set up, all signal quality-based features would be excluded during classifier development for this 'subject classifier'. Each of these classification methods may be more suited to different scenarios, due to the nature of the training data used—i.e., a Set Up classifier may be more useful to identify partner data at the start or end of a sleep session, while a Subject classifier may be more useful in identifying who was taking a nap during the day.

9.3.3 Use of Historical Data

A generic classification model could be used for the initial period of use, one night or possibly longer. This will allow subject-specific historical data to be gathered, which may be used to improve model performance over time. This may be updated periodically, providing a gradually more tailored, and more accurate, classifier as the use period extends. Example processes for such a classification model is illustrated in reference to FIG. 19. For example, during an initial use or set-up period, a setup classification process at 1920 may evaluate a set of features from the feature extraction unit 1922 for identification of the user. The setup classification may employ processes for respiration classification and/or movement classification at 1924 and 1926 respectively. A subject specific classification process 1928 may also be included. The more particular subject classification process 1928 may also employ processes for respiration classification and/or movement classification at 1930 and 1932 respectively. The process 1928 may evaluate a different set of features taken from the feature extraction unit 1922 than the set of features evaluated by the setup classification process at 1920, however, there may be an overlap of such sets of features.

A classifier combiner process 1940 may choose a classification, such as from the subject classification and the setup classification processes either alone or together at 1940. The output is the probability (a percentage) that the user is present, from which a binary decision is made. If the probability is less than a certain threshold, the output is that the partner was present, and if it is above that threshold, the output is that the user was present. The threshold may change over time, based on variables including (but not limited to) sleep duration or time of day. The classifier combiner may operate to selectively choose the output of the different classifier processes as a function of time (e.g., number of sessions or use data gathered). For example, initially it may choose only the setup classification and later (e.g., after a period of time or number of sessions) it may instead choose only the subject classification. Optionally, the combiner may selectively modify weightings given to both of the identifications output from the different classification processes over time. For example, it may provide greater weight to the identification made by the setup classification process initially and progressively increase the weight of the identification of the subject classification process with passing time of use. Separate respiration and movement classification processes are present to account for the possible NaN or zero features in one or other data stream (see section "8.3.1 Separate classifiers for movement and non-movement"); a separate cardiac features classifier can also be included.

9.4.0 Alternative Machine Learning Models

Optionally, other supervised, semi-supervised or unsupervised machine learning models may be implemented. For example, anomaly detection, support vector machine or clustering classification methods may serve in further system implementations.

10.0 Further Methodologies for Discrimination of Multiple User/Subjects

Figure 20:
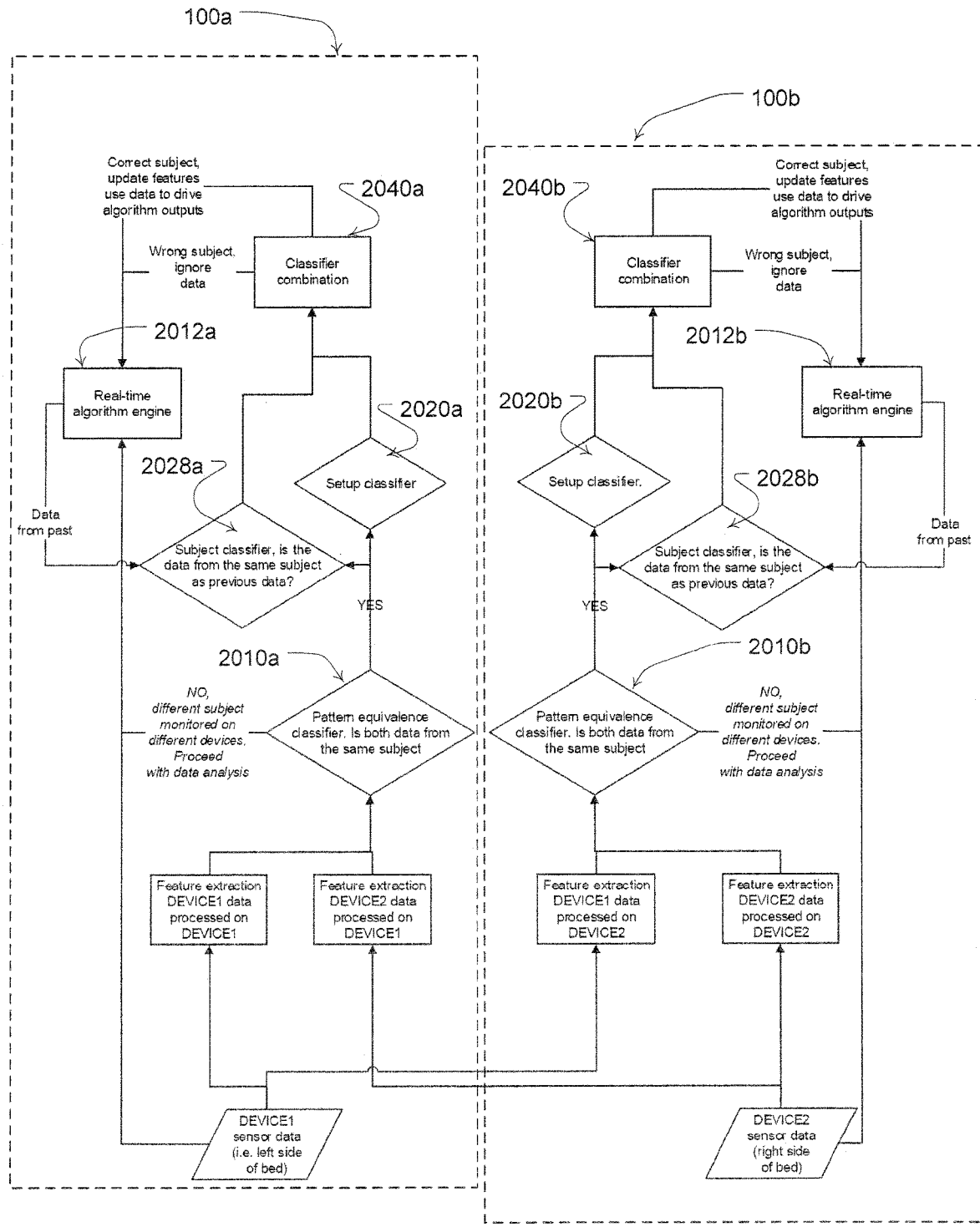
FIG. 20 illustrates processing of an example classification system for identification of two (or more) users in a sleeping (or waking) environment whereby the sensor data are compared to check that a detected user is the expected user at that side of the bed.
Figure 21A:
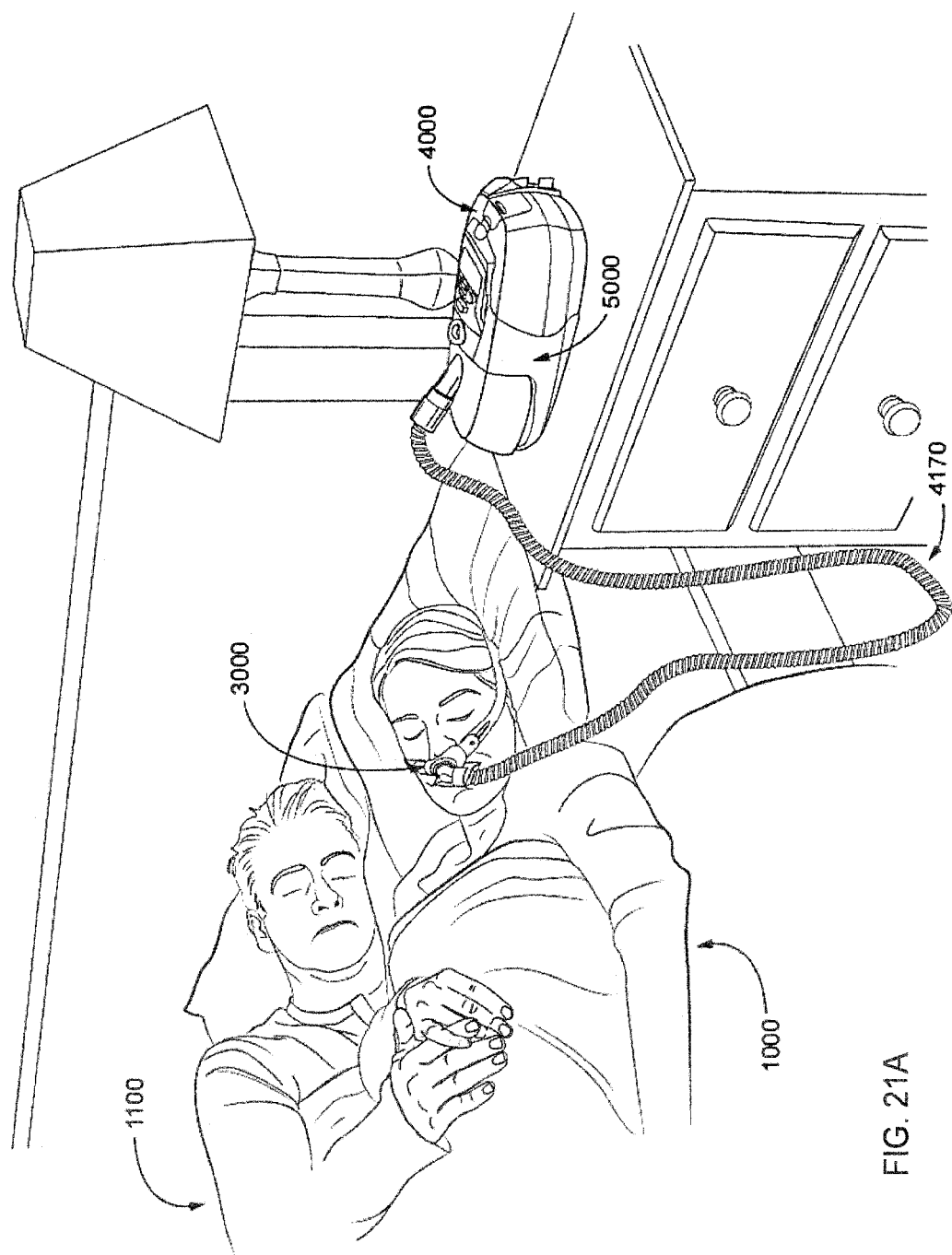
FIG. 21A shows a system in accordance with the present technology. A patient 1000 wearing a patient interface 3000 receives a supply of pressurised air from an RPT device 4000. Air from the RPT device 4000 is humidified in a humidifier 5000, and passes along an air circuit 4170 to the patient 1000. A bed partner 1100 is also shown.
Figure 21B:
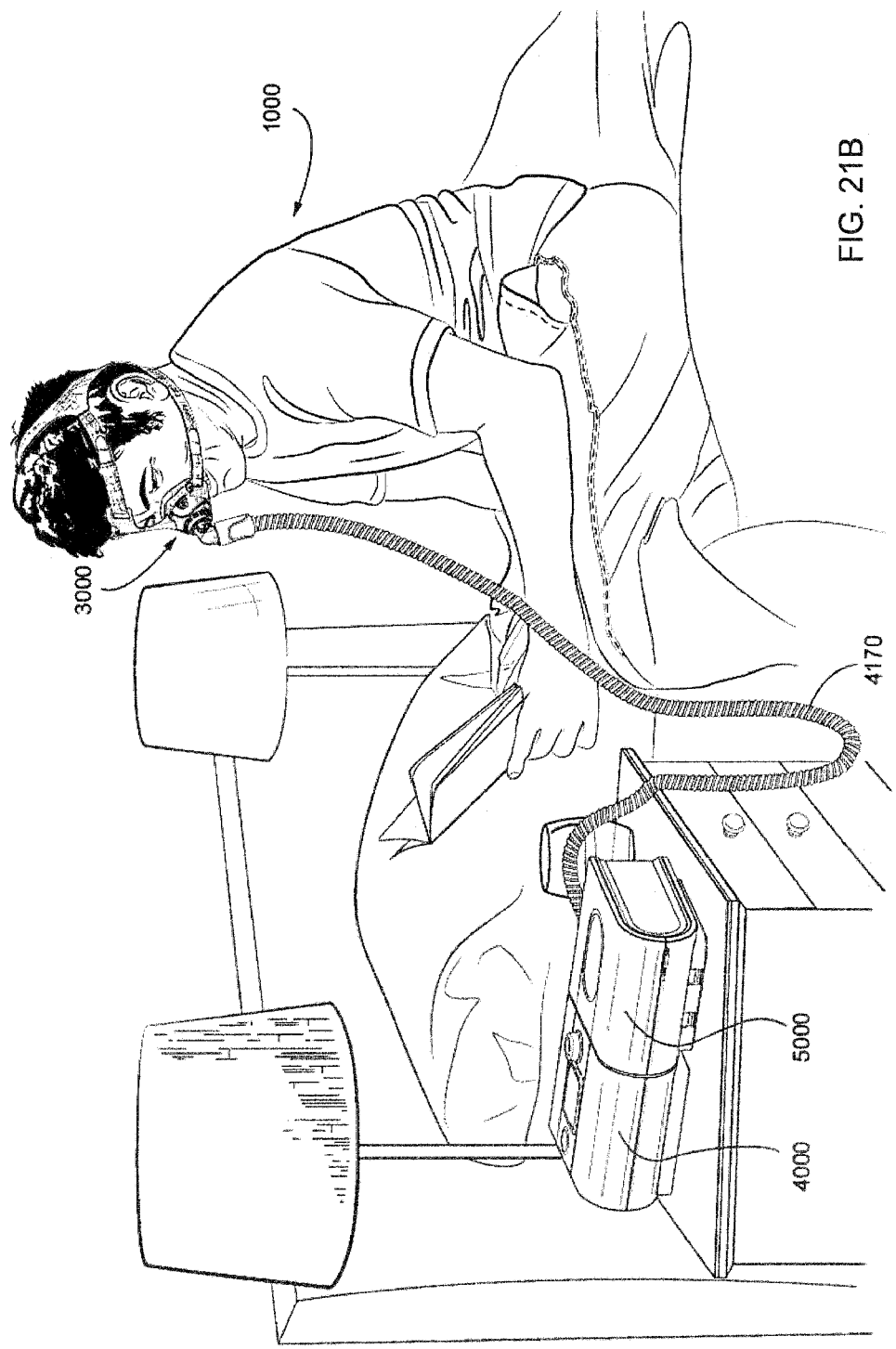
FIG. 21B shows an RPT device 4000 in use on a patient 1000 with a nasal mask type patient interface 3000.
Figure 21C:
FIG. 21C shows an RPT device 4000 in use on a patient 1000 with a full-face mask type patient interface 3000.
Figure 22:
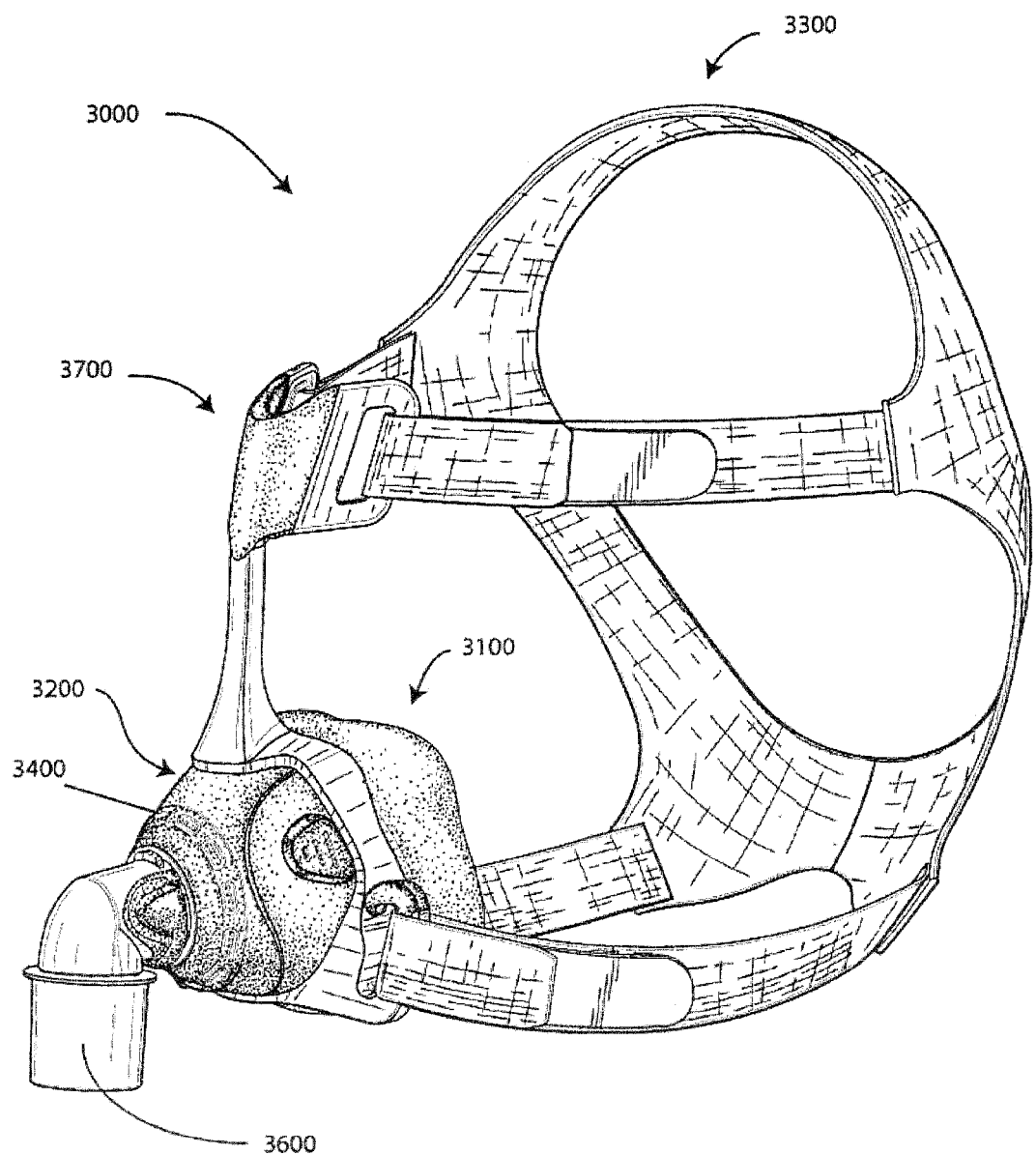
FIG. 22 shows a non-invasive patient interface 3000 in the form of a nasal mask.
Figure 23A:
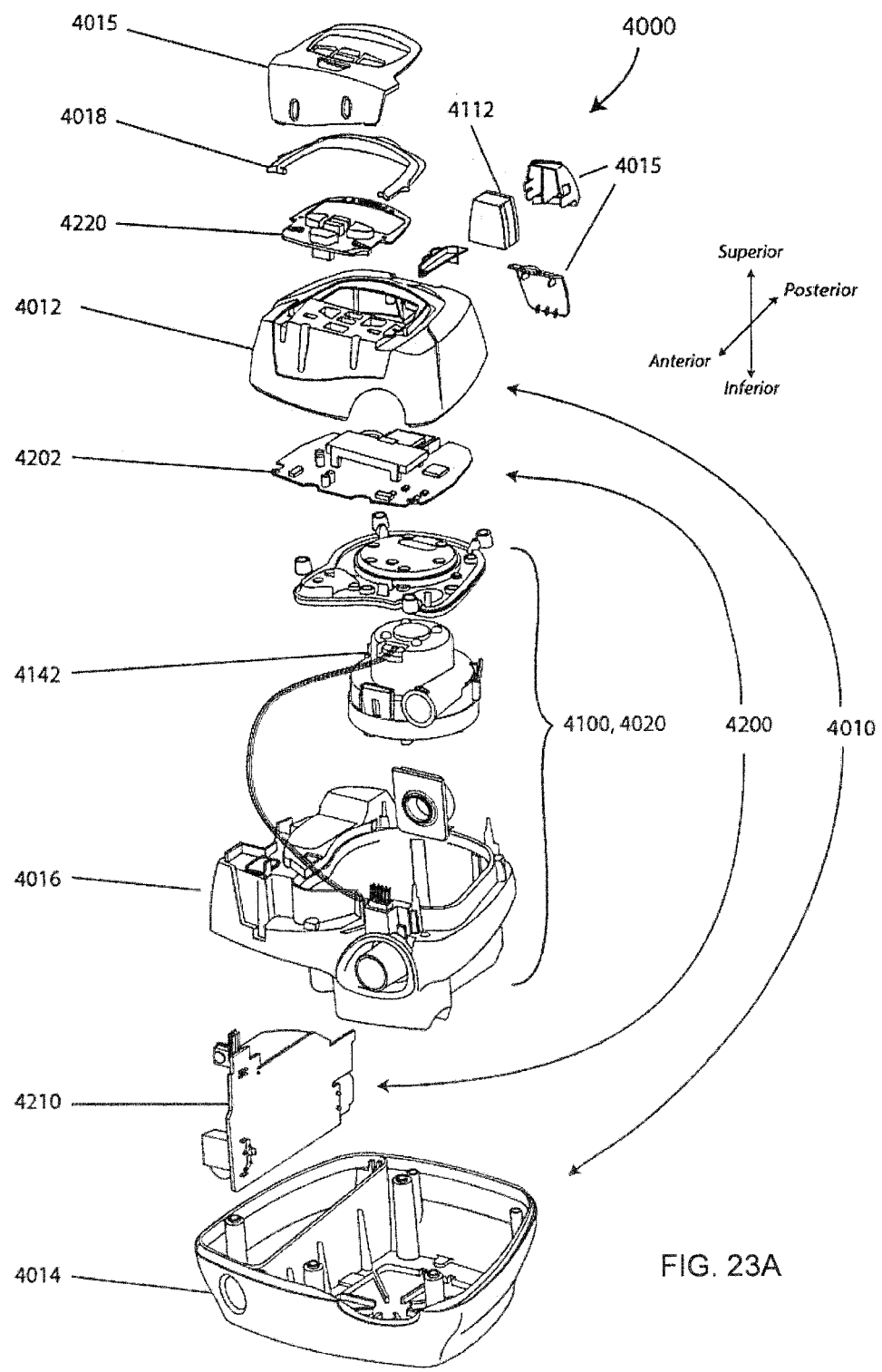
FIG. 23A shows an RPT device 4000 in accordance with one form of the present technology.
Figure 23B:
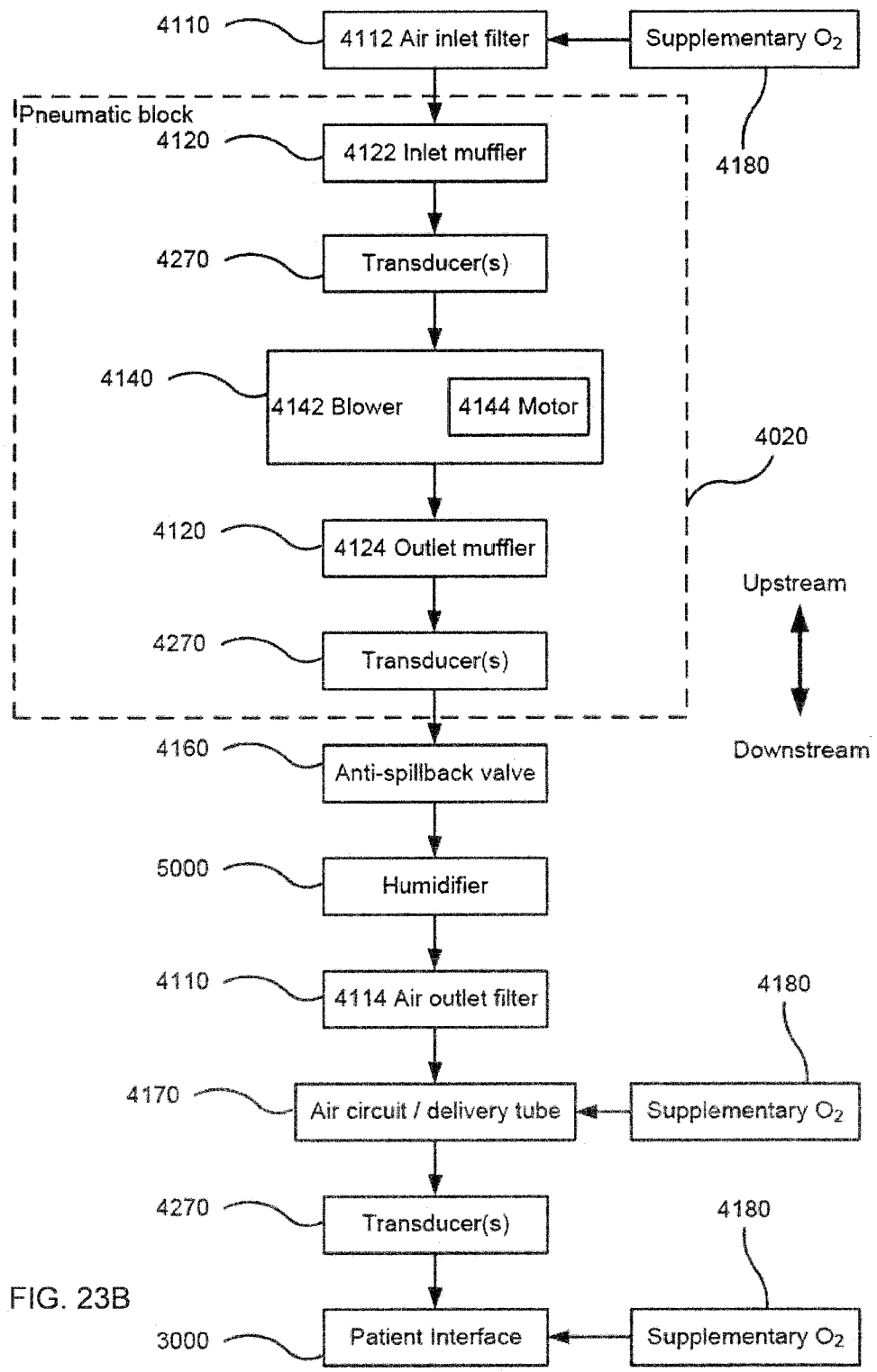
FIG. 23B shows a schematic diagram of the pneumatic circuit of an RPT device 4000 in accordance with one form of the present technology. The directions of upstream and downstream are indicated.
Figure 23C:
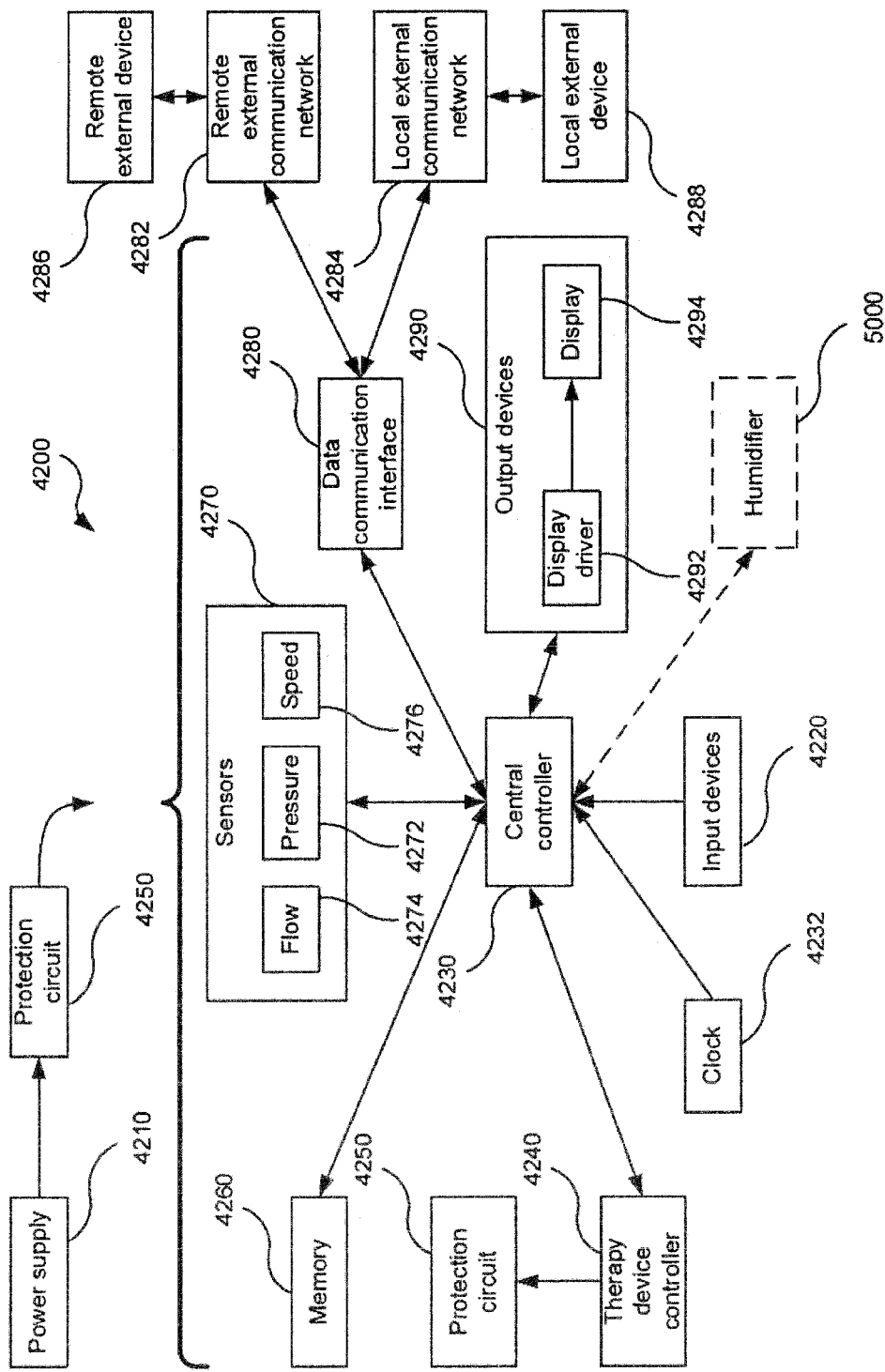
FIG. 23C shows a schematic diagram of the electrical components of an RPT device 4000 in accordance with one aspect of the present technology.
Figure 23D:
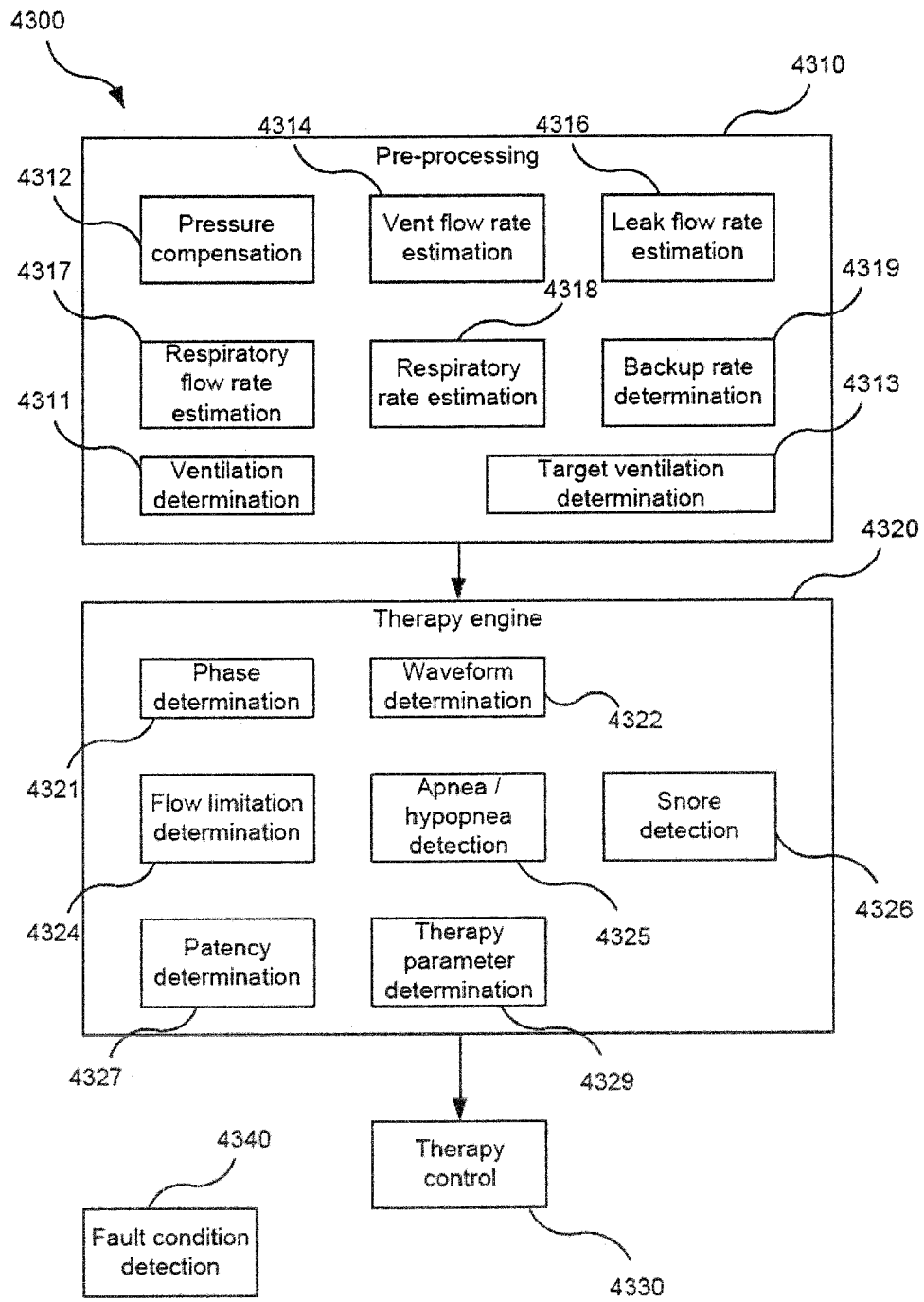
FIG. 23D shows a schematic diagram of the algorithms 4300 implemented in an RPT device 4000 in accordance with an aspect of the present technology.
Figure 23E:
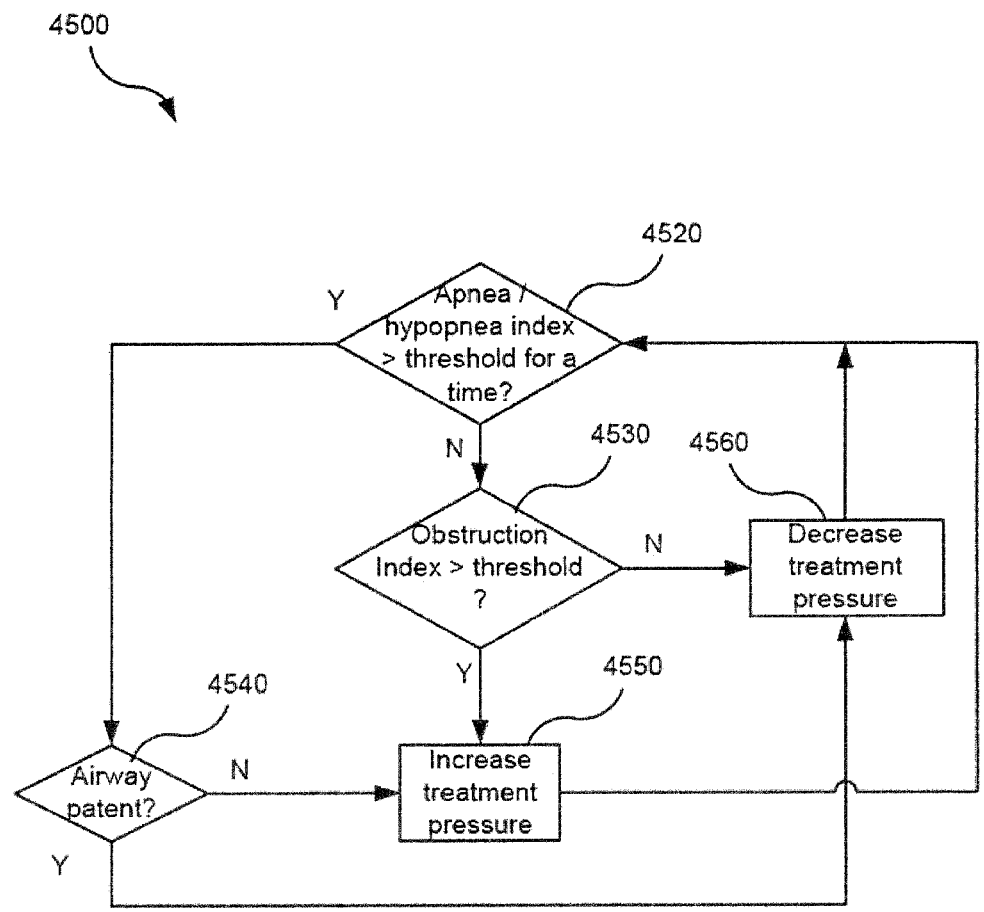
FIG. 23E is a flow chart illustrating a method 4500 carried out by the therapy engine module 4320 of FIG. 9D in accordance with one aspect of the present technology.

FIG. 20 illustrates processes that may be implemented in a system for discrimination of N subjects being monitored by N devices, such as in a case where multiple devices communicate with each other and/or in a case where a centralized processing device, e.g., server, processes data from the sensors. In FIG. 20, only two sensor devices 100-A and 100-B are shown.

For example, each sensor device can access or process data received from other sensor devices in a common vicinity and apply a staged classification process. For example each of sensor devices 1 and 2 in FIG. 20 may initially assess whether the other device has detected or is detecting the same at 2010*a*, 2010*b*, such as by comparing sensor data or features extracted from sensor data from both sensors. The "feature extraction" item refers to how data from device 2 will be processed on both device 1 (within the dotted area called 100*a*), as well as on device 2 (within the dotted area called 100*b*). Similarly for data from device 1, which will be processed on both devices. This allows comparison between data collected by both devices, and a decision to be made whether they were monitoring the same person, or two individuals. If they were monitoring the same person, data with the superior signal quality could be used, and classification would be used to determine which user it was. If the devices were monitoring two individuals, then this diagram assumes that it was the main user, and proceeds with data analysis.

If this is not the case, analysis on the device that detected a pattern may proceed as normal at 2012*a*, 2012*b*. That is, each device may then proceed with a monitoring session of each different user independently by collecting/evaluating sensed data (e.g., respiratory characteristics, cardiac characteristics, sleep characteristics, etc.) of each user.

However, if multiple devices detected the same pattern (that is, the same person is being detected by both sensors), parallel classifiers (e.g., two or more) may be processed on each device. Each device may then implement classifiers for confirming/identifying if the detected subject is a previously monitored user such as by implementing a process comparable to that described in FIG. 19. For example, the sensed data may be applied to a setup classification process 2020*a*, 2020*b* and/or subject specific classification process 2028*a*, 2028*b* aimed at subject recognition (such as with historical data). The classification combiner 2040*a*, 2040*b* may then decide if the data concerns a previously monitored subject. If it is a recognized user, sensor monitoring then proceeds at 2012*a*, 2012*b* to continue to monitor, such as in a cumulative manner with respect to previous sessions, the identified user. If it is not a recognized user, sensor data may be disregarded or the sensor may proceed to monitor the new user at 2012*a*, 2012*b*, in a non-cumulative fashion with respect to any sensor/monitoring data from prior sessions attributable to another user.

A potential advantage of this approach is that it can be applied to multiple people (e.g., two people with two sensors in a room), and is customized to certain people (e.g., two people) in a manner that does not require a biometric analysis against a greater population. In this regard, the discrimination may be a bounded problem relating to a finite group (e.g., household/bed partners or hospital room patients). Also, it enables shared communication of the outputs of multiple sensors to enable system level separation of sleep/respiration/movement/heart rate—even if the two sensors both detect a single bed user when the detection range overlaps. Thus, it can significantly improve the robustness of a deployed system within the context of widely varying shapes and sizes of beds, bed side lockers, people, etc.

It will be understood that even though FIG. 20 illustrates two parallel or coexistent sensor processes, more than two people could be monitored by replicating the flow process block with further devices and sharing of data.

In this regard, various technologies may be implemented for sharing of the sensor data by and between sensor devices. For example, wireless communications (e.g., Wi-Fi Direct (adhoc)) could optionally be implemented between sensors to enable the sensor-to-sensor (point-to-point) communication. Other forms of communications may also be implemented (e.g., wired or other wireless communications).

11.0 Additional Optional Features.

(i) In some cases, the sensors devices may be integrated as a product that can be wirelessly charged (e.g., using a QI wireless charger). Thus, such a chargeable sensor product may have a battery (e.g., Lithium) and a coil to allow charging. Such a sensor product could then be charged during the day when placed proximate to the wireless charger. After charging, it could then be inserted into a holding structure for directing the sensor product for use during a monitoring session (e.g., at night near a user). For example, the sensor may mate with a wall mount, stand or bed mount where they receive the chargeable sensor product. The wireless charger may then be available for use to charge other devices during the night (e.g., a smartphone).

(ii) In some cases, the sensor devices may each include a microphone and/or an integrated camera sensitive to infra-red (e.g., a camera device that does not filter IR or is otherwise optimized to detect infra-red). An infra-red emitter (e.g., one or more IR LEDs with a diffuser/lens) may also be included. The sensor device may then record user movement both via its non-contact sensor(s) and a camera in a dark bedroom (e.g., recorded on the device memory, and/or transmitted via wireless communications). Where events are detected in real-time or at end of night (e.g., SDB episodes, particular types of movement such as PLM/RLS, unusual movements, breathing rate as detected via a non-contact or minimal contact sensor) or other events such as snore, wheeze, cough (e.g., detected via a non-contact microphone/transducer), a processor may link/associate the detected events with segments of video detected by the IR camera taken during a common time frame. The associated/linked segments (and optionally periodic timed frames) can then be accessed together (such as for display on a display device such as a phone or computer) to give the user an easy way to index the video to see significant events of the night. Thus, it can allow a user to, for example, view an SDB event in video. For example, they may see themselves stopping breathing, and taking a subsequent recovery breath. The video, indexed by events, could be seen on a smart device (such as a sensor device with an integrated monitor/display or a smart phone, laptop or computer that communicates with the sensor device) and could for example allow very fast video review of a night's sleep, e.g., by events.

(iii) Such a camera implemented sensor could also be implemented for remote viewing, such as in real time or near real time. For example, the sensor may serve to permit remote visual monitoring of a patient or other user's sleep and other states (e.g., is the monitored subject awake, in deep sleep etc.) Thus, it may serve as a baby monitor/remote health professional monitor such as in a clinic or hospital setting.)

12.0 Therapies

A range of therapies can be used to treat or ameliorate respiratory conditions, such for some versions of the present technology including a treatment device. Furthermore, otherwise healthy individuals may take advantage of such therapies to prevent respiratory disorders from arising.

Nasal Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion by pushing the soft palate and tongue forward and away from the posterior oropharyngeal wall.

Non-invasive ventilation (NIV) therapy provides ventilatory support to a patient through the upper airways to assist the patient in taking a full breath and/or maintaining adequate oxygen levels in the body by doing some or all of the work of breathing. NIV is provided via a non-invasive patient interface. NIV has been used to treat CSR, OHS, COPD, NMD, and Chest Wall disorders.

12.1 Diagnosis and Treatment Systems

In some versions of the technology, therapies may be provided by a treatment system or device that may work in coordination with the previously mentioned identification device/system. Such systems and devices may also be used to diagnose a condition without treating it.

A treatment system may comprise a Respiratory Pressure Therapy Device (RPT device), an air circuit, a humidifier, a patient interface, and data management.

A patient interface may be used to interface respiratory equipment to its user, for example by providing a flow of breathable gas. The flow of breathable gas may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH2O. For other forms of therapy, such as the delivery of oxygen or high flow rate air, the patient interface may not include a seal sufficient to facilitate delivery to the airways of a supply of air at a positive pressure of about 10 cmH2O.

12.2 Respiratory Pressure Therapy (RPT) Devices

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, including one or more of comfort, noise, ease of use, efficacy, size, weight, manufacturability, cost, and reliability.

One known RPT device used for treating sleep disordered breathing is the S9 Sleep Therapy System, manufactured by ResMed, which proves CPAP therapy. Another example of an RPT device is a ventilator. Ventilators such as the ResMed Stellar™ Series of Adult and Paediatric Ventilators may provide invasive and non-invasive non-dependent ventilation therapy for a range of patients for treating a number of conditions such as but not limited to NMD, OHS and COPD.

RPT devices typically comprise a pressure generator, such as a motor-driven blower or a compressed gas reservoir, and are configured to supply pressurised air to the airways of a patient. The outlet of the RPT device is connected via an air circuit to a patient interface such as those described above.

12.1 Optional Example Treatment Devices

As previously mentioned, in one form, the present technology may include an apparatus or device for treating and/or monitoring a respiratory disorder. The apparatus or device may be an RPT device 4000 for supplying pressurised air to the patient 1000 via an air circuit 4170 leading to a patient interface 3000. In the following description, the RPT device may be considered in reference to FIGS. 21-24.

12.2 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, a connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to an airway of the patient so as to facilitate the supply of pressurised air to the airway.

12.3 RPT Device

An RPT device 4000 in accordance with one aspect of the present technology comprises mechanical and pneumatic components 4100, electrical components 4200 and is programmed to execute one or more algorithms 4300. The RPT device 4000 may have an external housing 4010 formed in two parts, an upper portion 4012 and a lower portion 4014. In one form, the external housing 4010 may include one or more panel(s) 4015. The RPT device 4000 may comprise a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying pressurised air (e.g. a blower 4142), an outlet muffler 4124, and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

12.3.1 RPT Device Mechanical & Pneumatic Components

An RPT device 4000 may comprise one or more of the following components in an integral unit. In an alternative form, one or more of the following components may be located as respective separate units.

12.3.1.1 Air Filter(s)

An RPT device 4000 in accordance with one form of the present technology may include an air filter 4110, or a plurality of air filters 4110.

In one form, an air inlet filter 4112 is located at the beginning of the pneumatic path upstream of a pressure generator 4140.

In one form, an air outlet filter 4114, for example an antibacterial filter, is located between an outlet of the pneumatic block 4020 and a patient interface 3000.

12.3.1.2 Muffler(s)

An RPT device 4000 in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

12.3.13 Pressure Generator

In one form of the present technology, a pressure generator 4140 for supplying pressurised air is a controllable blower 4142. For example, the blower 4142 may include a brushless DC motor 4144 with one or more impellers housed in a volute. The pressure generator 4140 may be capable of generating a supply or flow of air, for example at about 120 litres/minute, at a positive pressure in a range from about 4 cmH$_2$O to about 20 cmH$_2$O, or in other forms up to about 30 cmH$_2$O.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

12.3.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 are constructed and arranged to generate data representing respective properties of the air flow, such as a flow rate, a pressure or a temperature, at that point in the pneumatic path.

In one form of the present technology, one or more transducers 4270 are located proximate to the patient interface 3000.

In one form, a signal from a transducer 4270 may be filtered, such as by low-pass, high-pass or band-pass filtering.

12.3.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

12.3.1.6 Air Circuit

An air circuit 4170 in accordance with one aspect of the present technology is a conduit or tube constructed and arranged to allow, in use, a flow of air to travel between two components such as the pneumatic block 4020 and the patient interface 3000.

12.3.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

12.3.2 RPT Device Electrical Components 12.3.2.1 Power Supply

In one form of the present technology power supply 4210 is internal of the external housing 4010 of the RPT device 4000. In another form of the present technology, power supply 4210 is external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000.

12.3.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

12.3.2.3 Central Controller

In one form of the present technology, the central controller 4230 is a processor suitable to control an RPT device 4000 such as an x86 INTEL processor.

A central controller 4230 suitable to control an RPT device 4000 in accordance with another form of the present technology includes a processor based on ARM Cortex-M processor from ARM Holdings. For example, an STM32 series microcontroller from ST MICROELECTRONICS may be used.

Another central controller 4230 suitable to control an RPT device 4000 in accordance with a further alternative form of the present technology includes a member selected from the family ARM9-based 32-bit RISC CPUs. For example, an STR9 series microcontroller from ST MICROELECTRONICS may be used.

In certain alternative forms of the present technology, a 16-bit RISC CPU may be used as the central controller 4230 for the RPT device 4000. For example a processor from the MSP430 family of microcontrollers, manufactured by TEXAS INSTRUMENTS, may be used.

In another form of the present technology, the central controller 4230 is a dedicated electronic circuit. In another form, the central controller 4230 is an application-specific integrated circuit (ASIC). In another form, the central controller 4230 comprises discrete electronic components.

The central controller 4230 is configured to receive input signal(s) from one or more transducers 4270, one or more input devices 4220, and the humidifier 5000.

The central controller 4230 is configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein such as the one or more algorithms 4300 expressed as computer programs stored in a non-transitory computer readable storage medium, such as memory 4260. In some forms of the present technology, as previously discussed, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

While the central controller 4230 may comprise a single controller interacting with various sensors (e.g., transducers 4270), data communications interface 4280, memory 4260, as well as other devices, the functions of controller 4230 may be distributed among more than one controller. Thus, the term "central" as used herein is not meant to limit the architecture to a single controller or processor that controls the other devices. For example, alternative architectures may include a distributed controller architecture involving more than one controller or processor. This may include, for example, a separate local (i.e., within RPT device 4000) or remotely located controller that perform some of the algorithms 4300, or even more than one local or remote memory that stores some of the algorithms. In addition, the algorithms when expressed as computer programs may comprise high level human readable code (e.g., C++, Visual Basic, other object oriented languages, etc.) or low/machine level instructions (Assembler, Verilog, etc.). Depending on the functionality of an algorithm(s), such code or instructions may be burnt in the controller, e.g., an ASIC or DSP, or be a run time executable ported to a DSP or general purpose processor that then becomes specifically programmed to perform the tasks required by the algorithm(s).

12.3.2.4 Clock

The RPT device 4000 may include a clock 4232 that is connected to the central controller 4230.

12.3.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

12.3.2.6 Protection Circuits

An RPT device 4000 in accordance with the present technology may comprise one or more protection circuits 4250.

One form of protection circuit 4250 in accordance with the present technology is an electrical protection circuit.

One form of protection circuit 4250 in accordance with the present technology is a temperature or pressure safety circuit.

12.3.2.7 Memory

In accordance with one form of the present technology the RPT device 4000 includes memory 4260, for example non-volatile memory. In some forms, memory 4260 may include battery powered static RAM. In some forms, memory 4260 may include volatile RAM.

Memory 4260 may be located on PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

12.3.2.8 Transducers

Transducers may be internal of the device 4000, or external of the RPT device 4000. External transducers may be located for example on or form part of the air delivery circuit 4170, e.g. at the patient interface 3000. External transducers may be in the form of non-contact sensors such as a Doppler radar movement sensor that transmit or transfer data to the RPT device 4000.

12.3.2.8.1 Flow Rate

A flow rate transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In one example, a signal representing total flow rate Qt from the flow transducer 4274 is received by the central controller 4230.

12.3.2.8.2 Pressure

A pressure transducer 4272 in accordance with the present technology is located in fluid communication with the pneumatic path. An example of a suitable pressure transducer 4272 is a sensor from the HONEYWELL ASDX series. An alternative suitable pressure transducer is a sensor from the NPA Series from GENERAL ELECTRIC.

In use, a signal from the pressure transducer 4272 is received by the central controller 4230. In one form, the signal from the pressure transducer 4272 is filtered prior to being received by the central controller 4230.

12.3.2.8.3 Motor Speed

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

12.3.2.9 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

In one form, the interface may communicate with a sensor, such as any of the sensors described herein including for example, an RF motion sensor.

12.3.2.10 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

12.3.2.10.1 Display Driver

A display driver 4292 receives as an input the characters, symbols, or images intended for display on the display 4294, and converts them to commands that cause the display 4294 to display those characters, symbols, or images.

12.3.2.10.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

12.3.3 RPT Device Algorithms 12.3.3.1 Pre-Processing Module

A pre-processing module 4310 in accordance with the present technology receives, as an input, raw data from a transducer 4270, for example a flow rate sensor 4274 or a pressure sensor 4272, and performs one or more process steps to calculate one or more output values that will be used as an input to another module, for example a therapy engine module 4320.

In one form of the present technology, the output values include the interface or mask pressure Pm, the respiratory flow rate Qr, and the leak flow rate Ql.

In various forms of the present technology, the pre-processing module 4310 comprises one or more of the following algorithms: pressure compensation 4312, vent flow rate estimation 4314, leak flow rate estimation 4316, respiratory flow rate estimation 4317, ventilation determination 4311, target ventilation determination 4313, respiratory rate estimation 4318, and backup rate determination 4319.

12.3.3.1.1 Pressure Compensation

In one form of the present technology, a pressure compensation algorithm 4312 receives as an input a signal indicative of the pressure in the pneumatic path proximal to an outlet of the pneumatic block 4020. The pressure compensation algorithm 4312 estimates the pressure drop in the air circuit 4170 and provides as an output an estimated pressure, Pm, in the patient interface 3000.

12.3.3.1.2 Vent Flow Rate Estimation

In one form of the present technology, a vent flow rate estimation algorithm 4314 receives as an input an estimated pressure, Pm, in the patient interface 3000 and estimates a vent flow rate of air, Qv, from a vent 3400 in a patient interface 3000.

12.3.3.1.3 Leak Flow Rate Estimation

In one form of the present technology, a leak flow rate estimation algorithm 4316 receives as an input a total flow rate Qt and a vent flow rate Qv, and estimates a leak flow rate Ql. In one form, the leak flow rate estimation algorithm 4316 estimates the leak flow rate Ql by calculating an average of the difference between the total flow rate and the vent flow rate Qv over a period sufficiently long to include several breathing cycles, e.g. about 10 seconds.

In one form, the leak flow estimation algorithm 4316 receives as an input a total flow rate Qt, a vent flow rate Qv, and an estimated pressure, Pm, in the patient interface 3000, and estimates a leak flow rate Ql by calculating a leak conductance, and determining a leak flow rate Ql to be a function of leak conductance and the pressure Pm. Leak conductance may be calculated as the quotient of low-pass filtered non-vent flow rate equal to the difference between total flow rate Qt and vent flow rate Qv, and low-pass filtered square root of pressure Pm, where the low-pass filter time constant has a value sufficiently long to include several breathing cycles, e.g. about 10 seconds. The leak flow rate Ql may be estimated as the product of leak conductance and a function of pressure, Pm.

12.3.3.1.4 Respiratory Flow Rate Estimation

In one form of the present technology, a respiratory flow rate estimation algorithm 4317 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

In other forms of the present technology, the respiratory flow estimation algorithm 4317 provides a value that acts as a proxy for the respiratory flow rate Qr. Possible proxies for respiratory flow rate include:

Respiratory movement of the chest of the patient 1000
Current drawn by the pressure generator 4140
Motor speed of the pressure generator 4140
Trans-thoracic impedance of the patient 1000

The respiratory flow rate proxy value may be provided by a transducer 4270 in the RPT device 4000, e.g. the motor speed sensor 4276, or a sensor external to the RPT device 4000, such a respiratory movement sensor or a trans-thoracic impedance sensor.

12.3.3.1.5 Ventilation Determination

In one form of the present technology, a ventilation determination algorithm 4311 receives an input a respiratory flow rate Qr, and determines a measure Vent indicative of current patient ventilation.

In some implementations, the ventilation determination algorithm 4311 determines a measure of ventilation Vent that is an estimate of actual patient ventilation.

In one such implementation, the measure of ventilation Vent is half the absolute value of respiratory flow, Qr, optionally filtered by low-pass filter such as a second order Bessel low-pass filter with a corner frequency of 0.11 Hz.

In one such implementation, the measure of ventilation Vent is an estimate of gross alveolar ventilation (i.e. non-anatomical-deadspace ventilation). This requires an estimate of anatomical deadspace. One can use the patient's height (or arm-span in cases of severe skeletal deformity) as a good predictor of anatomical deadspace. Gross alveolar ventilation is then equal to a measure of actual patient ventilation, e.g. determined as above, less the product of the estimated anatomical deadspace and the estimated spontaneous respiratory rate Rs.

In other implementations, the ventilation determination algorithm 4311 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where 0<K<1. There is an arbitrarily large number of measures that are exactly proportional to ventilation if the flow rate waveform shape is constant.

In other forms, the ventilation determination algorithm 4311 determines a measure Vent of ventilation that is not based on respiratory flow rate Qr, but is a proxy for the current patient ventilation, such as oxygen saturation ($SaO_2$), or partial pressure of carbon dioxide ($PCO_2$), obtained from suitable sensors attached to the patient 1000.

12.3.3.1.6 Target Ventilation Determination

In one form of the present technology, a central controller 4230 takes as input the measure of current ventilation, Vent, and executes one or more target ventilation determination algorithms 4313 for the determination of a target value Vtgt for the measure of ventilation.

In some forms of the present technology, there is no target ventilation determination algorithm 4313, and the target ventilation Vtgt is predetermined, for example by hard-coding during configuration of the RPT device 4000 or by manual entry through the input device 4220.

In other forms of the present technology, such as adaptive servo-ventilation (ASV) therapy (described below), the target ventilation determination algorithm 4313 computes the target ventilation Vtgt from a value Vtyp indicative of the typical recent ventilation of the patient 1000.

In some forms of adaptive servo-ventilation therapy, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation therapy, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4313, the recent history is of the order of several minutes, but in any case should be longer than the timescale of Cheyne-Stokes waxing and waning cycles. The target ventilation determination algorithm 4313 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

12.3.3.1.7 Respiratory Rate Estimation

In one form of the present technology, a respiratory rate estimation algorithm 4318 receives as an input a respiratory flow rate, Qr, to the patient 1000, and produces an estimate of the spontaneous respiratory rate Rs of the patient.

The respiratory rate estimation algorithm 4318 may estimate the spontaneous respiratory rate Rs over periods when the patient 1000 is breathing spontaneously, i.e. when the RPT device 4000 is not delivering "backup breaths" (described below). In some forms of the present technology, the respiratory rate estimation algorithm 4318 estimates the respiratory rate over periods when servo-assistance (defined as pressure support minus minimum pressure support) is low, in one implementation less than 4 $cmH_2O$, as such periods are more likely to reflect spontaneous respiratory effort.

In some forms of the present technology, the respiratory rate estimation algorithm 4318 estimates the respiratory rate over periods of asleep breathing, since the respiratory rate during these periods may be substantially different from the respiratory rate during wake. Anxiety typically results in a higher respiratory rate than that prevailing during sleep. When patients focus on their own breathing process, their respiratory rates are typically lower than those during normal wakefulness or during sleep. Techniques such as described in Patent Application no. PCT/AU2010/000894, published as WO 2011/006199, the entire disclosure of which is hereby incorporated herein by reference, may be used to identify periods of awake breathing from the respiratory flow rate, Qr.

In some forms of the present technology, the respiratory rate estimation algorithm 4318 estimates the spontaneous respiratory rate Rs as the reciprocal of one of a variety of well-known statistical measures of central tendency of breath duration Ttot during the period of interest. In such measures it is desirable to reject, or at least be robust to, outliers. One such measure, trimmed mean, in which the lower and upper K proportions of the sorted breath durations are discarded and the mean calculated on the remaining breath durations, is robust to outliers. For example, when K is 0.25, this amounts to discarding the upper and lower quartiles of breath duration Trot. The median is another robust measure of central tendency, though this can occasionally give unsatisfactory results when the distribution is strongly bimodal. A simple mean may also be employed as a measure of central tendency, though it is sensitive to outliers. An initial interval filtering stage, in which contiguous time intervals corresponding to implausible respiratory rates (e.g. greater than 45 breaths/minute or less than 6 breaths/minute) are excluded as outliers from the mean calculation, may be employed. Other filtering mechanisms which may be used alone or in combination with interval filtering are to exclude any breaths that are not part of a sequence of N successive spontaneous breaths, where N is some small integer (e.g. 3), and to exclude the early and late breaths of a sequence of successive spontaneous breaths, e.g. to exclude the first and last breaths of a sequence of four breaths. The rationale for the latter mechanism is that the first and the last breaths in particular, and the early and late breaths in general, of a sequence of spontaneous breaths may be atypical; for example, the first spontaneous breath may occur as a result of an arousal, and the last spontaneous breath may be longer because of the decreasing respiratory drive which results in the backup breath which ends the sequence of spontaneous breaths.

In some forms of the present technology, the respiratory rate estimation algorithm 4318 makes an initial estimate of the spontaneous respiratory rate Rs using an initial period of estimation, to enable the subsequent processing in the therapy engine module 4320 to begin, and then continuously updates the estimate of the spontaneous respiratory rate Rs using a period of estimation that is longer than the initial period of estimation, to improve statistical robustness. For example, the initial period of estimation may be 20 minutes of suitable spontaneous breaths, but the period of estimation may then progressively increase up to some maximum duration, for example 8 hours. Rather than a rolling window of this duration being used for this estimation, low-pass filters on breath duration may be used, with progressively longer response times (more precisely, progressively lower corner frequencies) as the session proceeds.

In some forms, a suitably processed short-term (e.g. 10-minute) measure of central tendency, such as trimmed mean, may be input to a suitable low-pass filter to give an estimate Rs which changes on the time scale of hours or longer. This has the advantage that potentially large amounts of breath duration data do not need to be stored and processed, as might occur if a trimmed mean needs to be calculated on a moving window of breath duration data lasting hours or days.

In some forms of the present technology, respiratory rates measured over short periods of time, and in particular over one breath, may also be used instead of breath duration in the above-described measures of central tendency, giving generally similar but not identical results.

12.3.3.1.8 Backup Rate Determination

In one form of the present technology, a backup rate determination algorithm 4319 receives as input a spontaneous respiratory rate estimate Rs provided by the respiratory rate estimation algorithm 4318 and returns a "backup rate" Rb. The backup rate Rb is the rate at which the RPT device 4000 will deliver backup breaths, i.e. continue to provide ventilatory support, to a patient 1000 in the absence of significant spontaneous respiratory effort.

In one form of the pre-processing module 4310, there is no backup rate determination algorithm 4319, and the backup rate Rb is instead provided manually to the RPT device 4000, e.g. via the input device 4220, or hard-coded at the time of configuration of the RPT device 4000.

In one form, known as adaptive backup rate, the backup rate determination algorithm 4319 determines the backup rate Rb as a function of the spontaneous respiratory rate Rs. In one implementation, the function determines the backup rate Rb as the spontaneous respiratory rate Rs minus a constant such as 2 breaths per minute. In another implementation, the function determines the backup rate Rb as the spontaneous respiratory rate Rs multiplied by a constant that is slightly less than unity.

In one form, known as variable backup rate, the backup rate determination algorithm 4319 determines the backup rate Rb as a function of time. The backup rate Rb is initialised to a value known as the spontaneous backup rate (SBR) that is some fraction of a final target backup rate, known as the sustained timed backup rate (STBR). The fraction may be two thirds, or three quarters, or other positive values less than one. The SBR is the reciprocal of the timeout period to a backup breath when the most recent inspiration was a spontaneous (i.e. patent-triggered) breath. The STBR may be predetermined (e.g. by manual entry or hard-coding as described above) or set to some typical respiratory rate such as 15 bpm. Over time elapsed since the previous spontaneous breath, the backup rate Rb is increased from the SBR towards the STBR. The increase may be according to a predetermined profile, such as a series of steps, or a continuous linear profile. The profile is chosen such that the backup rate Rb reaches the STBR after a predetermined interval. The interval may be measured in units of time, such as 30 seconds, or relative to the patient's respiration, such as 5 breaths.

In some forms of variable backup rate, the predetermined interval over which the backup rate Rb increases from the SBR towards the STBR may be a function of the adequacy of current ventilation. In one implementation, suitable for servo-ventilation in which a target value Vtgt exists for the measure of ventilation, the backup rate approaches the STBR faster to the extent that current measure of ventilation Vent is less than the target ventilation Vtgt.

In one form of variable backup rate, known as adaptive variable backup rate, the backup rate determination algorithm 4319 determines the backup rate Rb as a function of the current estimated spontaneous respiratory rate Rs provided by the respiratory rate estimation algorithm 4318, as well as a function of time. As in variable backup rate determination, adaptive variable backup rate determination increases the backup rate Rb from the SBR towards the STBR over a predetermined interval that may be a function of the adequacy of current ventilation. The STBR may be initialised to a standard respiratory rate, such as 15 bpm. Once a reliable estimate of spontaneous respiratory rate Rs is available from the respiratory rate estimation algorithm 4318, the STBR may be set to the current estimated spontaneous respiratory rate Rs multiplied by some constant. The SBR may be set to some fraction of the STBR, as in variable backup rate. In one form, the fraction, for example two thirds, can be set to a lower value, such as 0.55, during the initial period of estimation of the spontaneous respiratory rate Rs, to accommodate occasional long breath durations in patients with relatively low respiratory rates, such as 12 breaths per minute.

In some forms, the constant by which the current estimated spontaneous respiratory rate Rs is multiplied to obtain the STBR may be slightly higher than 1, e.g. 1.1, to provide more aggressive ventilation during apneas, which may be desirable in short apneas. The constant may be somewhat lower than 1, e.g. 0.8, particularly if difficulty in resynchronisation with the patient on the return of patient effort turns out to be a problem in a particular patient. Lower backup rates make resynchronisation easier, by lengthening the expiratory pause, during which resynchronisation commonly occurs.

12.3.3.2 Therapy Engine Module

In one form of the present technology, a therapy engine module 4320 receives as inputs one or more of a pressure, Pm, in a patient interface 3000, a respiratory flow rate of air to a patient, Qr, and an estimate Rs of the spontaneous respiratory rate, and provides as an output one or more therapy parameters. In various forms, the therapy engine module 4320 comprises one or more of the following algorithms: phase determination algorithm 4321, waveform determination algorithm 4322, inspiratory flow limitation determination algorithm 4324, apnea/hypopnea determination algorithm 4325, snore detection algorithm 4326, airway patency determination algorithm 4327, and therapy parameter determination algorithm 4329.

12.3.3.2.1 Phase Determination

In one form of the present technology, a phase determination algorithm 4321 receives as an input a signal indicative of respiratory flow, Qr, and provides as an output a phase Φ of a current breathing cycle of a patient 1000.

In some forms, known as discrete phase determination, the phase output Φ is a discrete variable. One implementation of discrete phase determination provides a bi-valued phase output Φ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output Φ is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold.

Another implementation of discrete phase determination provides a tri-valued phase output Φ with a value of one of inhalation, mid-inspiratory pause, and exhalation.

In other forms, known as continuous phase determination, the phase output Φ is a continuous value, for example varying from 0 to 1 revolutions, or 0 to 2π radians. RPT devices 4000 that perform continuous phase determination may trigger and cycle when the continuous phase reaches 0 and 0.5 revolutions, respectively. In one implementation of continuous phase determination, a continuous value of phase Φ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr.

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.
4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's respiratory rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the inhalation time Ti and the exhalation time Te are first estimated from the respiratory flow rate Qr. The phase Φ is then determined as the half the proportion of the inhalation time Ti that has elapsed since the previous trigger instant, or 0.5 revolutions plus half the proportion of the exhalation time Te that has elapsed since the previous cycle instant (whichever was more recent).

In some forms of the present technology, suitable for pressure support ventilation therapy (described below), the phase determination algorithm 4321 is configured to trigger even when the respiratory flow rate Qr is insignificant, such as during an apnea. As a result, the RPT device 4000 delivers "backup breaths" in the absence of spontaneous respiratory effort from the patient 1000. For such forms, known as spontaneous/timed (S/T) modes, the phase determination algorithm 4321 may make use of the backup rate Rb provided by the backup rate determination algorithm 4319.

A phase determination algorithm 4321 that uses "fuzzy phase" may implement S/T mode using the backup rate Rb by including a "momentum" rule in the fuzzy phase rules. The effect of the momentum rule is to carry the continuous phase forward from exhalation to inhalation at the backup rate Rb if there are no features of respiratory flow rate Qr that would otherwise carry the continuous phase forward through the other rules. In one implementation, the more it is true that the measure of ventilation Vent (described below) is well below a target value Vtgt for ventilation (also described below), the more highly the momentum rule is weighted in the combination. However, as a result of the rapid increase in pressure support in response to mild to moderate hypoventilation (with respect to the target ventilation), the ventilation may be quite close to the target ventilation. It is desirable that the momentum rule is given a low weighting when the ventilation is close to target, to allow the patient to breathe at rates significantly lower than the respiratory rate at other times (when the patient is not in a central apnea) without being unnecessarily pushed to breathe at a higher rate by the ventilator. However, when the momentum rule is given a low weighting when ventilation is above a value which is below but close to the target ventilation, adequate ventilation may easily be achieved at a relatively high pressure support at a rate well below the backup rate. It would be desirable for the backup breaths to be delivered at a higher rate, because this would enable the target ventilation to be delivered at a lower pressure support. This is desirable for a number of reasons, a key one of which is to diminish mask leak.

To summarise, in a fuzzy phase determination algorithm 4321 that implements S/T mode, there is a dilemma in choosing the weighting for the momentum rule incorporating the backup rate Rb: if it is too high, the patient may feel "pushed along" by the backup rate. If it is too low, the pressure support may be excessive. Hence it is desirable to provide methods of implementing S/T mode which do not rely on the momentum rule described above.

A phase determination algorithm 4321 (either discrete, or continuous without a momentum rule) may implement S/T mode using the backup rate Rb in a manner known as timed backup. Timed backup may be implemented as follows: the phase determination algorithm 4321 attempts to detect the start of inhalation due to spontaneous respiratory effort, for example by monitoring the respiratory flow rate Qr as described above. If the start of inhalation due to spontaneous respiratory effort is not detected within a period of time after the last trigger instant whose duration is equal to the reciprocal of the backup rate Rb (an interval known as the backup timing threshold), the phase determination algorithm 4321 sets the phase output (to a value of inhalation (thereby triggering the RPT device 4000). Once the RPT device 4000 is triggered, and a backup breath begins to be delivered, the phase determination algorithm 4321 attempts to detect the start of spontaneous exhalation, for example by monitoring the respiratory flow rate Qr, upon which the phase output Φ is set to a value of exhalation (thereby cycling the RPT device 4000).

If the backup rate Rb is increased over time from the SBR to the STBR, as in a variable backup rate system described above, the backup timing threshold starts out longer and gradually becomes shorter. That is, the RPT device 4000 starts out less vigilant and gradually becomes more vigilant to lack of spontaneous respiratory effort as more backup breaths are delivered. Such an RPT device 4000 is less likely to make a patient feel "pushed along" if they would prefer to breathe at a lower than standard rate, while still delivering backup breaths when they are needed.

If the STBR in a variable backup rate system adapts to the patient's estimated spontaneous respiratory rate Rs, as in an adaptive variable backup rate system described above, the backup breaths will be delivered at a rate that adapts to the patient's own recent spontaneous respiratory efforts.

12.3.3.2.2 Waveform Determination

In one form of the present technology, the therapy control module 4330 controls a pressure generator 4140 to provide a treatment pressure Pt that varies as a function of phase Φ of a breathing cycle of a patient according to a waveform template Π (Φ).

In one form of the present technology, a waveform determination algorithm 4322 provides a waveform template Π (Φ) with values in the range [0, 1] on the domain of phase values Φ provided by the phase determination algorithm 4321 to be used by the therapy parameter determination algorithm 4329.

In one form, suitable for either discrete or continuously-valued phase, the waveform template Π (Φ) is a square-wave template, having a value of 1 for values of phase up to and including 0.5 revolutions, and a value of 0 for values of phase above 0.5 revolutions. In one form, suitable for continuously-valued phase, the waveform template Π (Φ) comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. One example of such a "smooth and comfortable" waveform template is the "shark fin" waveform template, in which the rise is a raised cosine, and the smooth decay is quasi-exponential (so that the limit of Π as Φ approaches one revolution is precisely zero).

In some forms of the present technology, the waveform determination algorithm 4322 selects a waveform template Π (Φ) from a library of waveform templates, dependent on a setting of the RPT device 4000. Each waveform template Π (Φ) in the library may be provided as a lookup table of values Π against phase values Φ. In other forms, the waveform determination algorithm 4322 computes a waveform template Π (Φ) "on the fly" using a predetermined functional form, possibly parametrised by one or more parameters (e.g. time constant of an exponentially curved portion). The parameters of the functional form may be predetermined or dependent on a current state of the patient 1000.

In some forms of the present technology, suitable for discrete bi-valued phase of either inhalation (Φ=0 revolutions) or exhalation (Φ=0.5 revolutions), the waveform determination algorithm 4322 computes a waveform template Π "on the fly" as a function of both discrete phase Φ and time t measured since the most recent trigger instant (transition from exhalation to inhalation). In one such form, the waveform determination algorithm 4322 computes the waveform template (Φ, t) in two portions (inspiratory and expiratory) as follows:

$$\Pi(\Phi, t) = \begin{cases} \Pi_i(t), & \Phi = 0 \\ \Pi_e(t - T_i), & \Phi = 0.5 \end{cases}$$

where $\Pi_i(t)$ and $\Pi_e(t)$ are inspiratory and expiratory portions of the waveform template Π (Φ, t), and Ti is the inhalation time. In one such form, the inspiratory portion $\Pi_i(t)$ of the waveform template is a smooth rise from 0 to 1 parametrised by a rise time, and the expiratory portion $\Pi_e(t)$ of the waveform template is a smooth fall from 1 to 0 parametrised by a fall time.

12.3.3.2.3 Determination of Inspiratory Flow Limitation

In one form of the present technology, a processor executes one or more algorithms 4324 for the detection of inspiratory flow limitation (partial obstruction).

In one form the algorithm 4324 receives as an input a respiratory flow rate signal Qr and provides as an output a metric of the extent to which the inspiratory portion of the breath exhibits inspiratory flow limitation.

In one form of the present technology, the inspiratory portion of each breath is identified based on the phase D estimated at each instant. For example, the inspiratory portion of the breath is the values of respiratory flow for which the phase Φ is less than or equal to 0.5. A number of evenly spaced points (for example, sixty-five), representing points in time, are interpolated by an interpolator along the inspiratory flow-time curve for each breath. The curve described by the points is then scaled by a scaler to have unity length (duration/period) and unity area to remove the effects of changing respiratory rate and depth. The scaled breaths are then compared in a comparator with a pre-stored template representing a normal unobstructed breath. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by central controller 4230 for the preceding several inspiratory events. This is repeated over the same inspiratory events for the second such point, and so on. Thus, for example, sixty five scaled data points are generated by central controller 4230, and represent a moving average of the preceding several inspiratory events, e.g. three events. The moving average of continuously updated values of the (e.g. sixty five) points are hereinafter called the "scaled flow", designated as Qs(t). Alternatively, a single inspiratory event can be utilised rather than a moving average.

From the scaled flow, two shape factors relating to the determination of partial obstruction may be calculated.

Shape factor 1 is the ratio of the mean of the middle (e.g. thirty-two) scaled flow points to the mean overall (e.g. sixty-five) scaled flow points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical user.

Shape factor 2 is calculated as the RMS deviation from unit scaled flow, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can other than those described.

12.3.3.2.4 Determination of Apneas and Hypopneas

In one form of the present technology, a central controller 4230 executes one or more algorithms 4325 for the detection of apneas and/or hypopneas.

In one form, the one or more apnea/hypopnea detection algorithms 4325 receive as an input a respiratory flow rate Qr and provide as an output a flag that indicates that an apnea or a hypopnea has been detected.

In one form, an apnea will be said to have been detected when a function of respiratory flow rate Qr falls below a flow threshold for a predetermined period of time. The function may determine a peak flow, a relatively short-term mean flow, or a flow intermediate of relatively short-term mean and peak flow, for example an RMS flow. The flow threshold may be a relatively long-term measure of flow.

In one form, a hypopnea will be said to have been detected when a function of respiratory flow rate Qr falls below a second flow threshold for a predetermined period of time. The function may determine a peak flow, a relatively short-term mean flow, or a flow intermediate of relatively short-term mean and peak flow, for example an RMS flow. The second flow threshold may be a relatively long-term measure of flow. The second flow threshold is greater than the flow threshold used to detect apneas.

12.3.3.2.5 Detection of Snore

In one form of the present technology, a central controller 4230 executes one or more snore detection algorithms 4326 for the detection of snore.

In one form, the snore detection algorithm 4326 receives as an input a respiratory flow rate signal Qr and provides as an output a metric of the extent to which snoring is present.

The snore detection algorithm 4326 may comprise a step of determining the intensity of the flow rate signal in the range of 30-300 Hz. The snore detection algorithm 4326 may further comprises a step of filtering the respiratory flow rate signal Qr to reduce background noise, e.g. the sound of airflow in the system from the blower 4142.

12.3.3.2.6 Determination of Airway Patency

In one form of the present technology, a central controller 4230 executes one or more algorithms 4327 for the determination of airway patency.

In one form, airway patency algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cmH$_2$O.

In one form, airway patency algorithm 4327 receives as an input a respiratory flow rate signal Qr, and determines the presence or absence of a cardiogenic signal. The absence of a cardiogenic signal is taken to be an indication of a closed airway.

12.3.3.2.7 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi) + P_0 \tag{1}$$

where:
A is an amplitude,
$\Phi$ is the current value of phase;
$\Pi(\Phi)$ is the waveform template value (in the range 0 to 1) at the current value of phase, and
$P_0$ is a base pressure.

If the waveform determination algorithm 4322 provides the waveform template $\Pi(\Phi)$ as a lookup table of values indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen pressure therapy mode in the manner described below.

12.3.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of gas whose mask pressure Pm at the patient interface 3000 is equal to the treatment pressure Pt.

12.3.3.4 Detection of Fault Conditions

In one form of the present technology, a processor executes one or more methods 4340 for the detection of fault conditions. The fault conditions detected by the one or more methods may include at least one of the following:

Power failure (no power, or insufficient power)
Transducer fault detection
Failure to detect the presence of a component
Operating parameters outside recommended ranges (e.g. pressure, flow, temperature, $PaO_2$)
Failure of a test alarm to generate a detectable alarm signal.

Figure 24:
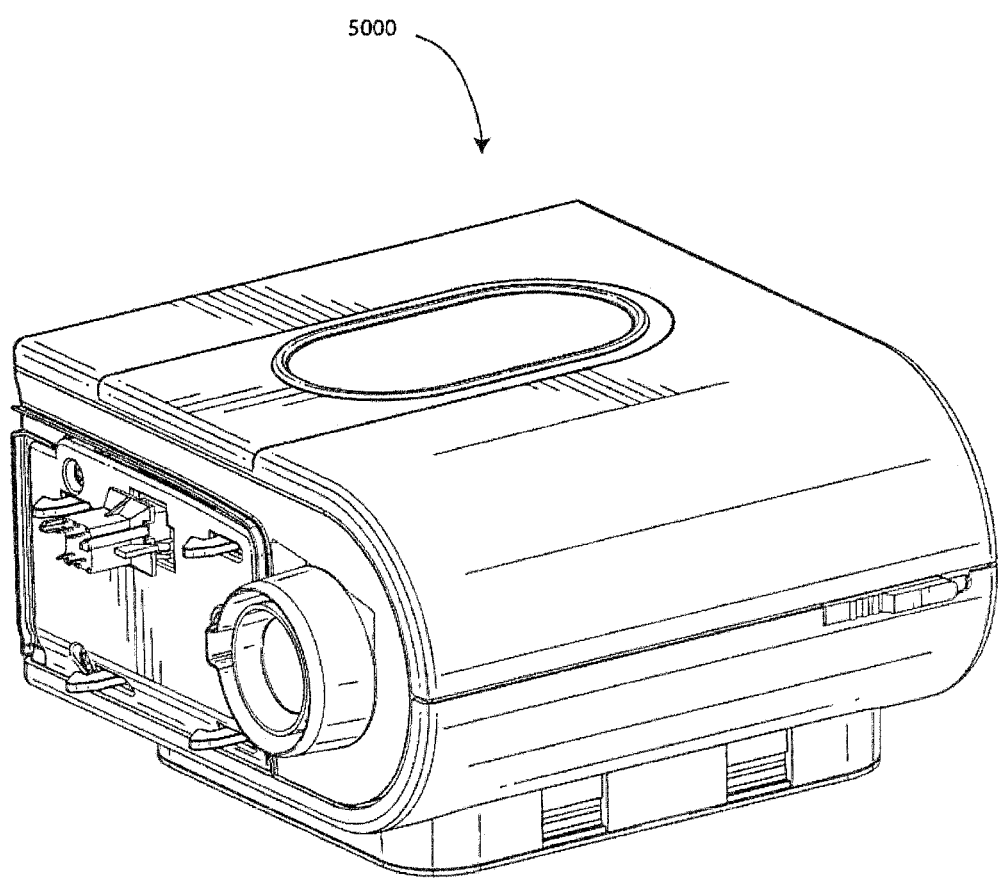
FIG. 24 shows a humidifier 5000.

Upon detection of the fault condition, the corresponding algorithm signals the presence of the fault by one or more of the following:

Initiation of an audible, visual &/or kinetic (e.g. vibrating) alarm
Sending a message to an external device
Logging of the incident 12.4 Humidifier In one form of the present technology there is provided a humidifier 5000 (e.g. as shown in FIG. 24) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

12.5 Glossary

For the purposes of the present disclosure, in certain forms of the present technology, one or more of the following definitions may apply. In other forms of the present technology, alternative definitions may apply.

12.5.1 General

Air: In certain forms of the present technology, air may be taken to mean atmospheric air, and in other forms of the present technology air may be taken to mean some other combination of breathable gases, e.g. atmospheric air enriched with oxygen.

Respiratory Pressure Therapy (RP): The delivery of a supply of air to the airways at a treatment pressure that is typically positive with respect to atmosphere.

Continuous Positive Airway Pressure (CPAP) therapy: Respiratory pressure therapy in which the treatment pressure is approximately constant through a breathing cycle of a patient. In some forms, the pressure at the entrance to the airways will be slightly higher during exhalation, and slightly lower during inhalation. In some forms, the pressure will vary between different breathing cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

12.5.2 Aspects of the Breathing Cycle

Apnea: According to some definitions, an apnea is said to have occurred when respiratory flow rate falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing rate, or respiratory rate (Rs): The rate of spontaneous respiration of a patient, usually measured in breaths per minute.

Duty cycle: The ratio of inhalation time, Ti to total breath duration, Ttot.

Effort (breathing): The work done by a spontaneously breathing person attempting to breathe.

Expiratory portion of a breathing cycle: The period from the start of expiratory flow to the start of inspiratory flow.

Flow limitation: The state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: A reduction in flow, but not a cessation of flow. In one form, a hypopnea may be said to have occurred when there is a reduction in flow below a threshold for a duration. In one form in adults, the following either of the following may be regarded as being hypopneas:

(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow rate (Qpeak): The maximum value of flow during the inspiratory portion of the respiratory flow rate waveform.

Respiratory flow/airflow rate, patient flow/airflow rate (Qr): These synonymous terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inhaled or exhaled during normal breathing, when extra effort is not applied.

Inhalation Time (Ti): The duration of the inspiratory portion of the respiratory flow rate waveform.

Exhalation Time (Te): The duration of the expiratory portion of the respiratory flow rate waveform.

(total) Time, or breath duration (Ttot): The total duration between the start of the inspiratory portion of one respiratory flow rate waveform and the start of the inspiratory portion of the following respiratory flow rate waveform.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of the total amount of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

12.5.3 RPT Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow rate will be given the symbol Q. 'Flow rate' is sometimes shortened to simply 'flow'. Total flow rate, Qt, is the flow of air leaving the RPT device. Vent flow rate, Qv, is the flow of air leaving a vent to allow washout of exhaled gases. Leak flow rate, Ql, is the flow rate of unintentional leak from a patient interface system. Respiratory flow rate, Qr, is the flow of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2O$. The pressure in the patient interface (mask pressure) is given the symbol Pm, while the treatment pressure, which represents a target value to be achieved by the mask pressure Pm at the current instant of time, is given the symbol Pt.

12.5.4 Terms for Ventilators

Adaptive Servo-Ventilator (ASV): A servo-ventilator that has a changeable rather than a fixed target ventilation. The changeable target ventilation may be learned from some characteristic of the patient, for example, a respiratory characteristic of the patient.

Backup rate: A parameter of a ventilator that establishes the respiratory rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation. Servo-assistance: Pressure support minus minimum pressure support.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the inspiratory portion of the breathing cycle by the patient's efforts.

Typical recent ventilation: The typical recent ventilation Vtyp is the value around which recent measures of ventilation over some predetermined timescale tend to cluster, that is, a measure of the central tendency of the measures of ventilation over recent history.

Ventilator: A mechanical device that provides pressure support to a patient to perform some or all of the work of breathing.

12.6 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

It will further be understood that any reference herein to subject matter known in the field does not, unless the contrary indication appears, constitute an admission that such subject matter is commonly known by those skilled in the art to which the present technology relates.

PARTS LIST detection apparatus 100
patient 1000
bed partner 1100
feature extraction unit 1922
classification process 1928
classifier combiner process 1940
patient interface 3000
structure 3100
plenum chamber 3200
structure 3300
vent 3400
connection port 3600
forehead support 3700
RPT device 4000
external housing 4010
upper portion 4012
portion 4014
panel 4015
chassis 4016
handle 4018
pneumatic block 4020
pneumatic component 4100
air filter 4110
air inlet filter 4112
air outlet filter 4114
muffler 4120
inlet muffler 4122
outlet muffler 4124
pressure generator 4140
blower 4142
motor 4144
back valve 4160
air delivery circuit 4170
supplemental oxygen 4180
electrical component 4200
PCBA 4202
power supply 4210
input device 4220
central controller 4230
clock 4232
therapy device controller 4240
protection circuit 4250
memory 4260
transducer 4270
pressure sensor 4272
flow rate sensor 4274
motor speed sensor 4276
data communication interface 4280
remote external communication network 4282
local external communication network 4284
remote external device 4286
local external device 4288
output device 4290
display driver 4292
display 4294
algorithm 4300
processing module 4310
ventilation determination algorithm 4311
pressure compensation algorithm 4312
target ventilation determination algorithm 4313
target ventilation determination 4313
vent flow rate estimation algorithm 4314
leak flow rate estimation algorithm 4316
respiratory flow rate estimation algorithm 4317
respiratory rate estimation algorithm 4318
backup rate determination algorithm 4319
therapy engine module 4320
phase determination algorithm 4321
waveform determination algorithm 4322 inspiratory flow limitation determination
  algorithm 4324
apnea/hypopnea determination algorithm 4325
snore detection algorithm 4326
airway patency determination algorithm 4327
therapy parameter determination algorithm 4329
therapy control module 4330
method 4340
method 4500
humidifier 5000
setup classification process 2020a
setup classification process 2020b
specific classification process 2028a
specific classification process 2028b
classification combiner 2040a
classification combiner 2040b

The invention claimed is:

1. A physiological parameter monitoring system adapted to identify a person for monitoring of the identified person's physiological parameters, the system including:
   one or more sensors for monitoring one or more persons' physiological parameters, and
   one or more processors configured to process signals from the one or more sensors to identify a person, the processing comprising an evaluation of parameters comprising one or more respiratory parameters, cardiac parameters, or movement parameters,
   wherein the evaluation of parameters comprises analysis of detected respiration depth,
   the one or more processors being further configured to, in response to the evaluation, store locally, or to forward for remote storage, the monitored physiological parameters in association with the person identified from the evaluation,
   wherein the one or more processors is configured to operate an enrolment process for initialization of biometric characteristics for identifying the person, wherein the enrolment process comprises scanning of data from a user's sleep session to identify fiducial points in the data and calculate classification features for generation of a biometric signature for the user; and
   wherein the evaluation of parameters further comprises an assessment of the generated biometric signature.

2. The system of claim 1, wherein the monitoring comprises detection of physiological characteristics of the person during sleep, wherein the processing comprises one or more of (a) detection of sleep stages of the person, (b) detection of deep sleep of the person, and (c) detection of REM sleep of the person.

3. The system of claim 1 wherein the monitoring comprises detection of physiological characteristics during awake time of the person.

4. The system of claim 1 wherein the one or more sensors comprises any one or more of:
   a radio frequency non-contact sensor;
   a biomotion sensor; and
   a wearable sensor.

5. The system of claim 1 wherein the evaluation of the one or more processors comprises detection and analysis of any one or more characteristics comprising behavioural characteristics.

6. The system of claim 1 wherein the one or more sensors comprise at least two sensors, and wherein the at least two sensors are configured to minimize interference between the at least two of the one or more sensors.

7. The system of claim 1 wherein the one or more sensors minimize interference by modifying control parameters for range gating pulse timing, emitted power levels of pulses, detection frequency of pulses and/or adjusting positioning of a steerable antenna.

8. The system of claim 7 wherein the one or more sensors are configured to communicate via a wired or wireless link.

9. The system of claim 1 wherein characteristic biometric parameters are applied to dynamically adjust performance of at least one of the one or more sensors in order to optimize physiological recognition of independent human sources, and to reject other sources.

10. The system of claim 1 further comprising a control processor in communication with the one or more sensors, the control processor configured to communicate with the one or more sensors to adjust one or more detection control parameters of the one or more sensors based on an identification of the person, other people, or an animal by the one or more sensors.

11. The system of claim 10 wherein the detection control parameters of the one or more sensors comprises one or more of range gating, centre frequency, and power level.

12. The system of claim 1 further comprising a control processor in communication with the one or more sensors, the control processor configured to activate a further sensor system based on an identification of the person, other people, or an animal by the one or more sensors.

13. The system of claim 12 wherein the further sensor system comprises a camera.

14. The system of claim 1 wherein a processor is configured to log detected biometric characteristics based on the identification of the person to be a previously monitored person.

15. The system of claim 1 wherein a processor is configured to refrain from logging detected biometric characteristics based on the identification of the person to be a not previously monitored person.

16. The system of claim 1 wherein a processor is configured to initialize biometric characteristic detection for a particular person.

17. The system of claim 16 wherein the processor is configured to compare newly detected biometric characteristics to initialized biometric characteristics to identify the particular person.

18. The system of claim 16 wherein the evaluation further comprises a comparison between newly detected biometric characteristics and initialized biometric characteristics.

19. The system of claim 1 wherein the evaluation comprises classification of parameters determined from the signals, the parameters comprising one or more of:
   a spectral peak ratio;
   a set up Optimiser flag vector;
   a peak trough ratio;
   a filtered respiration rate;
   a breathing variability measure;
   an in-band power of a sensor signal;
   a range of a sensor signal;
   a final respiration rate;
   a ratio of maximum to minimum amplitude of a breathing cycle;
   a high band power for a sensor signal;
   a mean respiration rate;
   a periodic leg movement activity detection;
   a detection of turnover; and
   a post-processed movement.

20. The system of claim 1 wherein the evaluation comprises classification of parameters determined from the signals, the parameters comprising one or more of a cardiac parameter, a galvanic skin response parameter, an exercise intensity parameter, a respiration parameter, a blood pressure parameter, a coughing parameter, a snoring parameter, a sleep parameter.

21. The system of claim 19 wherein the evaluation comprises a comparison of the determined parameters with historic parameters.

22. The system of claim 19 wherein the evaluation further comprises calculating mean and/or standard deviation values for a period of time from the determined parameters.

23. The system of claim 1 wherein one or more processors of the system is configured to evaluate received data detected by one or more sensors from another monitoring system.

24. The system of claim 23 wherein the evaluation of the received data comprises a determination of sensing equivalence between a plurality of health monitoring devices.

25. The system of claim 1 wherein a monitoring device comprises a setup classifier and a subject classifier, each configured to evaluate parameters from the signals to identify a person.

26. The system of claim 25 wherein the subject classifier is further configured to evaluate historic parameters to identify a person.

27. The system of claim 1 wherein a health monitoring device further comprises a camera sensitive to infra-red and an infra-red emitter.

28. The system of claim 27 wherein one or more processors of the health monitoring device are configured to detect an event from the signals and associate the event with a particular portion of a video taken with the camera including the event.

29. The system of claim 27 wherein the health monitoring device further comprises a battery and a coil for wireless charging of the battery.

30. The system of claim 1 wherein the one or more processors is configured to control the one or more sensors to change sensor detection power, sensor frequency, sensor range gating or other control parameters for sensing, upon detection of biometric characteristics indicative of an animal.

31. The system of claim 1 wherein the one or more processors is configured to access setting parameters for any one or more of light, sound and/or environmental appliances based on identification of a specific person associated with the setting parameters.

32. The system of claim 31 wherein the one or more processors is configured to trigger setting of any one or more of light, sound and/or environmental appliances with setting parameters associated with detected biometrics of the specific person identified.

33. The system of claim 1 further comprising a central controller in communication with a collection of said sensors, said central controller configured to provide confirmation of location of identified persons within a structure.

34. The system of claim 1 wherein the one or more sensors comprises a night light.

35. The system of claim 1 wherein the one or more sensors comprises a pass through outlet.

36. The system of claim 1 wherein the one or more sensors comprises an AC plug for powering a sensor and an AC power pass through outlet.

37. The system of claim 1 wherein the one or more sensors comprises an USB plug for powering a sensor and a USB pass through connection adapter.

38. The system of claim 1 wherein the one or more sensors comprises a network interface for wireless or wired network communications.

39. The system of claim 1 wherein the one or more processors is configured to set operation of a respiratory treatment apparatus based on the person identified.

40. The system of claim 39 wherein the set operation permits or denies therapy with the respiratory treatment apparatus.

41. The system of claim 39 wherein the set operation changes therapy of the respiratory treatment apparatus.

42. The system of claim 39 wherein the one or more processors is configured to re-train for identification of the person if biometric characteristics evaluated in the identification are treated by the respiratory treatment apparatus.

43. The system of claim 1 wherein the one or more processors is configured to adjust operation of the one or more sensors upon determination of sensor signal quality.

44. The system of claim 1 wherein the one or more processors is configured to rely on different biometric characteristics to identify the person depending on a quality assessment of detected biometric characteristics.

45. The system of claim 1, wherein the enrollment process further comprises a guided breathing session or spontaneous breathing session.

46. The system of claim 1 wherein the one or more processors is configured to reject a biometric characteristic involved in identifying the person when frequency interference is detected.

47. The system of claim 1 wherein the one or more processors is configured to set operation of an alarm based on the person identified.

48. The system of claim 1 wherein the one or more processors is configured to identify a main user from one or more other users.

49. The system of claim 1, wherein the system is configured to track parameters of one or more users over time to build up classification features based on at least one of the one or more respiratory parameters, cardiac parameters, or movement parameters.

50. The system of claim 49, wherein at least one of the one or more respiratory parameters, cardiac parameters, or movement parameters includes at least one of the following respiration parameters: range, breath to breath variation, shape and inspiration verses expiration ratio.

51. The system of claim 1 wherein the one or more processors is configured to classify a user's identity from parameters determined in a classification process.

52. The system of claim 51 wherein the classification process comprises any one or more of a neural network, a hidden layer Markov model, logistic regression processing, linear kernel support vector machine, radial kernel support vector machine and Principal Component Analysis on the parameters prior to classification.

53. The system of claim 51 wherein the classification process includes real time parameters and offline parameters.

54. The system of claim 51 wherein the classification process includes multiple classifiers and late integration of their output to produce an output posterior probability.

55. The system of claim 1, comprising multiple sensors arranged for detecting a same or different persons, wherein the system is arranged to automatically adjust parameters of the multiple sensors, the parameters including at least one of: range, power, frequency, detection direction and radiation pattern.

56. A non-transitory processor-readable medium, having stored thereon processor-executable instructions which, when executed by a processor, cause the processor to identify a person for monitoring physiological parameters of one or more persons, the processor-executable instructions comprising:

instructions to access the one or more persons' physiological parameters sensed from one or more sensors, instructions to process signals from the one or more sensors to identify a person, by evaluating parameters derived from the signals comprising one or more respiratory parameters, cardiac parameters, or movement parameters, wherein the evaluating of parameters comprises analysis of detected respiration depth; and instructions to monitor the physiological parameters based on the identification of the person from the evaluating of the parameters whereby logging monitored parameters from another person as monitored parameters of the person identified is avoided, instructions to operate an enrolment process for initialization of biometric characteristics for identifying the person, wherein the enrolment process comprises a scan of data from a user's sleep session to identify fiducial points in the data and calculate classification features for generation of a biometric signature for the user; and wherein the evaluating of the parameters further comprises an assessment of the generated biometric signature.

57. The non-transitory processor-readable medium of claim 56 wherein the evaluation of parameters further comprises analysis of detected degree of in bed movement.

58. The system of claim 1 wherein the evaluation of parameters further comprises analysis of detected degree of in bed movement.

* * * * *